United States Patent
Chan et al.

(10) Patent No.: US 7,423,052 B2
(45) Date of Patent: Sep. 9, 2008

(54) PIPERIDINE COMPOUNDS FOR USE AS OREXIN RECEPTOR ANTAGOINST

(75) Inventors: Wai Ngor Chan, Harlow (GB); Amanda Johns, Harlow (GB); Christopher Norbert Johnson, Harlow (GB); Riccardo Novelli, Harlow (GB); Roderick Alan Porter, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 503 days.

(21) Appl. No.: 10/481,083

(22) PCT Filed: Jun. 25, 2002

(86) PCT No.: PCT/EP02/07007

§ 371 (c)(1), (2), (4) Date: Dec. 7, 2003

(87) PCT Pub. No.: WO03/002559

PCT Pub. Date: Jan. 9, 2003

(65) Prior Publication Data

US 2004/0215014 A1    Oct. 28, 2004

(30) Foreign Application Priority Data

Jun. 28, 2001 (GB) ................. 0115862.5
Dec. 19, 2001 (GB) ................. 0130347.8

(51) Int. Cl.
| A61K 31/4525 | (2006.01) |
| A61K 31/454 | (2006.01) |
| A61K 31/4535 | (2006.01) |
| C07D 401/14 | (2006.01) |
| C07D 405/14 | (2006.01) |
| C07D 409/14 | (2006.01) |
| C07D 413/14 | (2006.01) |

(52) U.S. Cl. ............ 514/320; 514/326; 546/196; 546/209; 546/210; 546/211; 546/212

(58) Field of Classification Search ............ 546/207, 546/184, 196, 209, 210, 211, 212; 548/400; 514/319, 324, 326, 320

See application file for complete search history.

(56) References Cited

U.S. PATENT DOCUMENTS

| 5,547,978 A | 8/1996 | Christensen et al. ....... 514/422 |
| 6,150,356 A | 11/2000 | Lloyd et al. ............... 514/218 |
| 6,235,755 B1 | 5/2001 | El Tayer et al. ........... 514/315 |
| 6,326,379 B1 | 12/2001 | Macor et al. .............. 514/303 |
| 6,410,529 B1 | 6/2002 | Chan et al. .............. 514/233.5 |
| 6,423,723 B1 | 7/2002 | El Tayer et al. ........... 514/299 |
| 6,511,977 B1 | 1/2003 | Lloyd et al. .............. 514/233.8 |
| 6,596,730 B1 | 7/2003 | Coulton et al. ............ 514/300 |
| 6,638,980 B1 | 10/2003 | Su et al. ..................... 215/620 |
| 6,649,656 B1 | 11/2003 | Tsuchiya et al. ............ 514/535 |
| 6,653,338 B2 | 11/2003 | El Tayer et al. .............. 514/411 |
| 6,677,354 B2 | 1/2004 | Branch et al. ............... 514/318 |
| 6,706,720 B2 * | 3/2004 | Atwal et al. ............... 514/259.3 |
| 6,784,189 B2 | 8/2004 | Lloyd et al. ................. 514/312 |
| 6,881,753 B2 | 4/2005 | Lloyd et al. ................. 514/604 |
| 6,890,932 B2 | 5/2005 | Tsuchiya et al. ............ 514/277 |
| 6,943,160 B2 | 9/2005 | Branch et al. ............. 514/235.2 |
| 6,967,196 B1 | 11/2005 | Smith et al. ................. 514/210 |
| 7,157,451 B2 | 1/2007 | Atwal et al. ........... 514/217.06 |
| 2004/0143115 A1 | 7/2004 | Branch et al. ............... 540/607 |
| 2004/0180887 A1 | 9/2004 | Branch et al. ............. 514/232.5 |
| 2004/0192673 A1 | 9/2004 | Gaillard et al. ......... 514/217.04 |
| 2004/0215014 A1 | 10/2004 | Chan et al. ................. 540/596 |
| 2006/0040937 A1 | 2/2006 | Branch et al. ............ 514/235.5 |

FOREIGN PATENT DOCUMENTS

| EP | 1 162 196 | 12/2001 |
| WO | WO 99/58533 | 11/1999 |
| WO | WO 00/37458 | 6/2000 |
| WO | WO 00/47576 | 8/2000 |
| WO | WO 01/44228 | 6/2001 |

OTHER PUBLICATIONS

Smart et al., "Orexins and the treatment of obesity," European Journal of Pharmacology 440 (2002) 199-212.*
Lang et al., "Structure-Activity Studies, etc.," J. Med. Chem. 2004, 47, 1153-1160.*
Kilduff et al., "The hypocretin/orexin, etc.," Trends Neurosi. 2000, 23, 359-365.*
Taheri et al., "The Role of Hyrpocretins,etc.," Annu. Rev. Neurosci., 2002, 25:283-313.*
Cai et al., "Antagonists of the orexin receptors", Expert Opin. Ther. Patents (2006) 16(5), 631-646.*
Rubini et al., "Synthesis of , etc.," Tetrahedron 42 (21), 6039-6045, 1986.*
Patani et al., "Bioisoterism: A Rational, etc.," Chem. Rev. 1996, 96, 3147-3148 and 3170.*
Marshall, et al., "Absolute Configuration of alpha-Methyldopamine Formed Metabolically from alpha-Methyldopa in Man." *J. Med. Chem.*, 16(3): 266-270 (1973).
Langmead et al. Br. J. Pharmacol., 141: 340-346 (2004).
Porter et al. Bioorg. & Med. Chem. Lett., 11: 1907-1910 (2001).
Duxon et al. Psychopharmacology, 153: 203-209 (2001).
White et al. Peptides, 26: 2331-2338 (2005).
Ishii et al. Behav. Brain Res., 160: 11-24 (2005).
Ishii et al. Behav. Brain Res., 157: 331-341 (2005).
Ishii et al. Physiol. & Behav., 81: 129-140 (2004).
Smith et al. Neurosci. Lett., 341: 256-258 (2003).
Haynes et al. Regulatory Peptides, 104: 153-159 (2002).
Bingham et al. Pain, 92: 81-90 (2001).
Rodgers et al. Eur. J. Neurosci., 13: 1444-1452 (2001).
Smart et al. Br. J. Pharmacol., 132: 1179-1182 (2001).
Jones et al. Psychopharmacology, 153: 210-218 (2001).
Haynes et al. Regulatory Peptides, 96: 45-51 (2000).
Boutrel et al. *PNAS*, 102(52): 19168-19173 (2005).

(Continued)

*Primary Examiner*—Patricia L Morris
(74) *Attorney, Agent, or Firm*—Kathryn L. Sieburth; Mary E. McCarthy; Charles M. Kinzig

(57) ABSTRACT

A invention relates to N aroyl cyclic amine derivatives and their use as pharmaceuticals, specifically as orexin receptor antagonists.

15 Claims, No Drawings

OTHER PUBLICATIONS

Borgland et al. *Neuron*, 49: 589-601 (2006).
Harris et al. *Nature*, 437: 556-559 (2005).
Brisbare-Roch et al. *Nature Medicine*, 13(2): 150-155 (2007).
Hagan et al. *Proc. Natl. Acad. Sci. USA.*, 96: 10911-10916 (1999).
Piper et al. *Eur. J. Neurosci.*, 12: 726-730 (2000).
Patani et al. *Chem. Rev.*, 96: 3147-3176 (1996).
Office Action, U.S. Appl. No. 10/481,133, filed Apr. 26, 2004.
King. Bioisoteres, Conformational etc., Med. Chem. Principle and Practice (1994) 206-209.
Rogers et al. *Neuropeptides*, 36(5): 303-325 (2002).
Mori et al. *Chem. Pharm. Bull.*, 32(10): 3840-47 (1984).
Defoin et al., *Helv. Chim. Acta*, 75(1): 109-123 (1992).
Baker et al. *Chem. Abstract*, 52: 2194 (1958).
Shaw et al. *Chem. Abstracts*, 90: 137628 (1979).
Ehrhardt et al. *Chem. Abstracts*, 109: 149536 (1988).
Collins et al. *J. Med. Chem.*, 41(12): 5037-5054 (1998).
Sohda et al. *Chem. & Pharm. Bull., Pharm. Soc. of Japan*, 30(10): 3580-3600 (1982).
Dieter et al. *J. Am. Chem. Soc.*, 109(7): 2040-2046 (1987).
Bal et al. *Polish J. Chem., Polish Chem. Soc.*, 55: 1681-1684 (1981).
Bal et al. *Polish J. Chem., Polish Chem. Soc.*, 55(10): 2171-2175 (1981).
Wanner et al. *Arch. Pharm.*, 326(10): 799-802 (1993).
Suzuki et al. *Heterocycles*, 50(1): 89-94 (1999).
Database Crossfire Beilstein 'Online! Database Accession No. 4519278 (BRN), XP002211820 & Tetrahedron Lett., 28(17): 1949-1952 (1987).
Database Crossfire Beilstein 'Online! Database Accession No. 7095929 (BRN), XP002211821 & J. Chem. Soc. Perkin 1, (10):2477-2486 (1982).
Database Crossfire Beilstein 'Online! Database Accession No. 339072 (BRN), XP002211822 & Rocz. Chem, 29: 1029-1039 (1955).
Database Crossfire Beilstein 'Online! Database Accession No. 1491413 (BRN), XP002211823 & Chem. Pharm. Bull, 16(10): 2074-2077 (1968).
Database Crossfire Beilstein 'Online! Database Accession No. 1600999 (BRN), XP002211824 & J. Org. Chem, 29: 2860 (1964).
Johns et al. *Chem. Abstracts*, 133: 177112 (2000).

* cited by examiner

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu Asn His
        35

PIPERIDINE COMPOUNDS FOR USE AS OREXIN RECEPTOR ANTAGOINST

This invention relates to N-aroyl cyclic amine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; a typical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; nausea and vomiting; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegencrative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see Cell, 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides N-aroyl cyclic amine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders. Additionally these compounds may be of use in the treatment of stroke, particularly isohemic or haemorrhagic stroke, and/or blocking the emetic response i.e. the compounds are useful in the treatment of nausea and vomiting.

International Patent Applications WO99/09024, WO99/58533, WO00/47577 and WO00/47580 disclose phenyl urea derivatives and WO00/47576 discloses quinolinyl cinnamide derivatives as orexin receptor antagonists.

According to the invention there is provided a compound of formula (I):

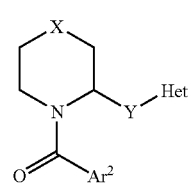

wherein:

X represents a bond, oxygen, $NR^3$ or a group $(CH_2)_n$, wherein n represents 1, 2 or 3, Y represents $CH_2$, CO, CHOH, or $—CH_2CH(OH)—$;

Het is an optionally substituted 5- or 6-membered monocyclic heteroaryl group containing up to 4 heteroatoms selected from N, O and S, substituted by $R^2$;

$Ar^2$ represents an optionally substituted phenyl or a 5- or 6-membered heteroaryl group containing up to 3 heteroatoms selected from N, O and S, wherein the phenyl or heteroaryl group is substituted by $R^1$ and further optional substituents; or $Ar^2$ represents an optionally substituted bicyclic aromatic or bicyclic heteroaromatic group containing up to 3 heteroatoms selected from N, O and S;

$R^1$ represents hydrogen, an optionally substituted $(C_{1-4})$ alkoxy, halo, cyano, optionally substituted $(C_{1-6})$ alkyl, optionally substituted phenyl, or an optionally substituted 5- or 6-membered heterocyclyl group containing up to 4 heteroatoms selected from N, O and S;

$R^2$ is an optionally substituted aryl or an optionally substituted mono or bicyclic heteroaryl group containing up to 3 heteroatoms selected from N, O and S;

$R^3$ is selected from hydrogen or $(C_{1-4})$alkyl;

or a pharmaceutically acceptable salt thereof.

A further aspect of the invention is the compound (RS)-1-dibenzofuran-4-yl-1-{2-[5-(3-fluoro-phenyl)[1,3,4]oxadiazol-2-ylmethyl]-piperidin-1-yl}-methanone or a pharmaceutically acceptable salt thereof.

Preferably where $Ar^2$ represents phenyl or a 5- or 6-membered heteroaryl group containing up to 3 heteroatoms selected from N, O and S, the $R^1$ group is situated adjacent to the point of attachment to the amide carbonyl.

Het may have up to 5, preferably 1, 2 or 3 optional substituents.

When Het is an optionally substituted 5- or 6-membered monocyclic heteroaryl group containing up to 4 heteroatoms selected from N, O and S, it may be oxazolyl, imidazolyl, thiazolyl, thiadiazolyl, oxadiazolyl, triazolyl, pyrazolyl, furanyl, tetrazolyl, pyrimidinyl, pyrazinyl, pyridazinyl or pyridinyl. Additionally Het may be isoxazolyl, isothiazolyl and triazinyl.

Prefered examples for Het are oxazolyl, imidazolyl, thiazolyl, triazolyl, oxadiazolyl and pyrazolyl. Additional prefered examples are furanyl and tetrazolyl.

When $Ar^2$ is a 5- or 6-membered heteroaryl group containing up to 3 heteroatoms selected from N, O and S, it may be furanyl, thienyl, pyrrolyl, oxazolyl, thiazolyl, imidazolyl, oxadiazolyl, thiadiazolyl, triazolyl, triazinyl, pyridazinyl, pyridinyl, pyrimidinyl, isothiazolyl, isoxazolyl, pyrazinyl, or pyrazolyl.

Alternatively, examples of $Ar^2$ are thiazolyl, pyrazolyl, triazolyl, pyridazinyl, oxazolyl, pyridinyl, pyrimidinyl, isoxazolyl and thienyl.

More specifically, examples of $Ar^2$ are thiazolyl, pyrazolyl, triazolyl, pyridazinyl, oxazolyl, pyridinyl, pyrimidinyl, and thienyl.

When $R^1$ is an optionally substituted 5- or 6-membered heterocyclyl group containing up to 4 heteroatoms selected from N, O and S, it may be furanyl, thienyl, pyrrolyl, oxazolyl, thiazolyl, imidazolyl, oxadiazolyl, thiadiazolyl, pyridinyl, triazolyl, triazinyl, pyridazinyl, pyrimidinyl, isothiazolyl, isoxazolyl, pyrazinyl or pyrazolyl. Alternatively $R^1$ can be piperidinyl, morpholinyl, thiomorpholinyl and piperazinyl. Additionally $R^1$ can be tetrazolyl.

Preferably $R^1$ is an optionally substituted 5- or 6-membered heteroaryl group containing up to 3 heteroatoms selected from N, O and S.

Examples of where $Ar^2$ represents an optionally substituted bicyclic aromatic or bicyclic heteroaromatic include naphthyl, quinolinyl, napththyridinyl, benzofuranyl, benzimidazolyl, quinoxalinyl or quinazolinyl. Additionally $Ar^2$ can be benzothienyl, benzotriazolyl, benzoxazolyl or indazolyl. Furthermore $Ar^2$ can be isoquinolinyl.

When $R^2$ is a mono or bicyclic heteroaryl group containing up to 3 heteroatoms selected from N, O and S, it can be, for example, benzofuranyl, pyrimidinyl, pyridinyl, pyridazinyl or furanyl.

Preferably $Ar^2$ represents optionally substituted phenyl, pyridinyl, thiazolyl, pyrazolyl, pyridazinyl, thienyl, benzofuranyl, naphthyl or triazolyl.

Alternatively $Ar^2$ represents optionally substituted phenyl, pyridinyl, thiazolyl, pyrazolyl, pyridazinyl, thienyl, benzofuranyl, naphthyl or 1,2,3-triazolyl.

X is preferably a bond, oxygen, or $(CH_2)_n$ wherein n is 1 or 2.

Y is preferably $CH_2$.

Alternatively $R^1$ represents hydrogen, an optionally substituted $(C_{1-4})$alkoxy, halo, optionally substituted $(C_{1-6})$alkyl, optionally substituted phenyl, or an optionally substituted 5- or 6-membered heteroaryl group containing up to 3 heteroatoms selected fromn N, O and S Furthermore $R^1$ can represent an optionally substituted $(C_{1-4})$alkoxy, halo, optionally substituted $(C_{1-6})$alkyl, optionally substituted phenyl, or an optionally substituted 5- or 6-membered heteroaryl group containing up to 3 heteroatoms selected from N, O and S Preferably $R^1$ is selected from an optionally substituted phenyl, pyridinyl, pyrazolyl, pyrimidazinyl, or oxadiazolyl group.

Preferably $R^2$ is attached to the atom in the monocyclic heteroaryl ring one removed from point of attachment of Het to the linker as shown in compound (I) of scheme 2a.

When used herein the term amide carbonyl means the —C(O)N bond wherein the N forms part of the cyclic amide ring Even more preferably $R^1$ represents an optionally substituted phenyl, or oxadiazolyl group.

Preferably $R^2$ is an optionally substituted phenyl.

More preferably Het is oxadiazolyl, oxazolyl, imidazolyl, furanyl, thiazolyl or triazolyl, even more preferably Het is oxadiazolyl, oxazolyl, imidazolyl or furanyl.

Optional substituents for the groups Het, $Ar^2$, $R^1$ and $R^2$ include halogen, hydroxy, oxo, cyano, nitro, $(C_{1-4})$alkyl, $(C_{1-4})$alkoxy, hydroxy$(C_{1-4})$alkyl, hydroxy$(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$allyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, $(C_{1-4})$arylcarboxamido$(C_{1-4})$alkyl, aroyl, aroyl$(C_{1-4})$alkyl, or aryl$(C_{1-4})$alkanoyl group; a group $R^aR^bN$-, $R^aOCO(CH_2)_r$, $R^aCON(R^a)(CH_2)_r$, $R^aR^bNCO(CH_2)_r$, $R^aR^bNSO_2(CH_2)_r$ or $R^aSO_2NR^b(CH_2)_r$ where each of $R^a$ and $R^b$ independently represents a hydrogen atom or a $(C_{1-4})$alkyl group or where appropriate $R^aR^b$ forms part of a $(C_{3-6})$azacyloalkane or $(C_{3-6})$(2-oxo)azacycloalkane ring and r represents zero or an integer from 1 to 4. Additional substituents are $(C_{1-4})$acyl, aryl, aryl$(C_{1-4})$alkyl, $(C_{1-4})$alkylamino$(C_{1-4})$alkyl, $R^aR^bN(CH_2)n$-, $R^aR^bN(CH_2)nO$—, wherein n represents an interger from 1 to 4. Additionally when the substituent is $R^aR^bN(CH_2)n$- or $R^aR^bN(CH)nO$, $R^a$ with at least one $CH_2$ of the $(CH_2)n$ portion of the group form a $(C_{3-6})$azacycloalkane and $R^b$ represents hydrogen, a $(C_{1-4})$alkyl group or with the nitrogen to which it is attached forms a second $(C_{3-6})$azacycloalkane fused to the first $(C_{3-6})$azacycloalkane.

Preferred optional substituents for $Ar^2$ are halogen, cyano, $(C)_4$)alkyl, hydroxy$(C_{1-4})$alkyl, $(C_{1-4})$alkoxy$(C_{1-4})$alkyl, $R^aR^bN(CH_2)n$, or $R^aR^bN$. Additionally prefered optional substituents are $(C_{1-4})$alkoxy, phenyl or nitro.

Preferred optional substituents for Het are halogen, cyano, or $(C_{1-4})$alkanoyl. Further optional substituents are hydroxy $(C_{1-4})$alkyl, $(C_{1-4})$alkyl, or $CF_3$.

Preferred optional substituents for $R^1$ are halogen, $(C_{1-4})$ alkoxy$(C_{1-4})$alkyl, $R^aR^bN$, $R^aR^bN(CH_2)n$ and $R^aR^bN(CH_2)nO$. Additional optional substituents are $(C_{1-4})$alkoxy, $(C_{1-4})$alkanoyl or $C_{1-4}$)alkyl.

Preferred optional substituents for $R^1$ are cyano, $(C_{1-4})$ alkyl, $(C_{1-4})$alkoxy and halogen.

In addition Het may be optionally substituted by a phenyl ring optionally substituted by a halogen, cyano, $C_{1-4}$aakyl, $C_{1-4}$alkanoyl or $C_{1-4}$alkylsulfonyl group; or by a 5- or 6-membered heterocyclic ring, such as a furanyl, pyridinyl, oxazolyl and pyrimidinyl. Additionally Het may be optionally substituted by a phenyl ring optionally substituted by $(C_{1-4})$alkoxy.

Preferred optional substituents for $Ar^2$ include halogen, cyano, and $(C_{1-4})$alkyl.

In the groups Het and $Ar^2$, substituents positioned ortho to one another may be linked to forms a ring.

Illustrative compounds of formula (I) can be selected from:

| | |
|---|---|
| 1 | (RS)-1-[5-(4-Fluoro-phenyl)-2-methyl-thiazol-4-yl]-1-[2-(5-phenyl-[1,3,4]oxadiazol-2-ylmethyl)-piperidin-1-yl]-methanone; |
| 2 | (RS)-1-[5-(4-Fluoro-phenyl)-2-methyl-2H-[1,2,3]triazol-4-yl]-1-[2-(5-phenyl-[1,3,4]oxadiazol-2-ylmethyl)-piperidin-1-yl]-methanone; |
| 3 | (RS)-1-[2-(3-Methyl-[1,2,4]oxadiazol-5-yl)-phenyl]-1-[2-(5-phenyl-[1,3,4]oxadiazol-2-ylmethyl)-piperidin-1-yl]-methanone |
| 4 | (RS)-1-Naphthalen-1-yl-1-[2-(5-phenyl-[1,3,4]oxadiazol-2-ylmethyl)-piperidin-1-yl]-methanone |
| 5 | (RS)-1-[2-(4-Fluoro-phenyl)-5-methyl-2H-pyrazol-3-yl]-1-[2-(5-phenyl-[1,3,4]oxadiazol-2-ylmethyl)-piperidin-1-yl]-methanone |
| 6 | (RS)-1-[4-(4-Fluoro-phenyl)-1-methyl-1H-pyrazol-3-yl]-1-[2-(5-phenyl-[1,3,4]oxadiazol-2-ylmethyl)-piperidin-1-yl]-methanone |
| 7 | (RS)-1-[4-(4-Fluoro-phenyl)-2-methyl-2H-pyrazol-3-yl]-1-[2-(5-phenyl-[1,3,4]oxadiazol-2-ylmethyl)-piperidin-1-yl]-methanone |
| 8 | (RS)-1-[4-(4-Fluoro-phenyl)-1H-pyrazol-3-yl]-1-[2-(5-phenyl-[1,3,4]oxadiazol-2-ylmethyl)-piperidin-1-yl]-methanone |
| 9 | (RS)-1-{2-[5-(3-Fluoro-phenyl)-[1,3,4]oxadiazol-2-ylmethyl]-piperidin-1-yl}-1-[2-(3-methyl-[1,2,4]oxadiazol-5-yl)-phenyl]-methanone |
| 10 | (RS)-1-[5-(4-Fluoro-phenyl)-2-methyl-thiazol-4-yl]-1-{2-[5-(3-fluoro-phenyl)-[1,3,4]oxadiazol-2-ylmethyl]-piperidin-1-yl}-methanone |
| 11 | (RS)-1-{2-[5-(3-Chloro-phenyl)-[1,3,4]oxadiazol-2-ylmethyl]-piperidin-1-yl}-1-[5-(4-fluoro-phenyl)-2-methyl-thiazol-4-yl]-methanone |
| 12 | (RS)-1-{2-[5-(3-Chloro-phenyl)-[1,3,4]oxadiazol-2-ylmethyl]-piperidin-1-yl}-1-[2-(3-methyl-[1,2,4]oxadiazol-5-yl)-phenyl]-methanone |
| 13 | (RS)-1-[5-(4-Fluoro-phenyl)-2-methyl-thiazol-4-yl]-1-[2-(5-pyridin-2-yl-[1,3,4]oxadiazol-2-ylmethyl)-piperidin-1-yl]-methanone |
| 14 | (RS)-1-[5-(4-Fluoro-phenyl)-2-methyl-thiazol-4-yl]-1-{2-[5-(4-fluoro-phenyl)-[1,3,4]oxadiazol-2-ylmethyl]-piperidin-1-yl}-methanone |
| 15 | (RS)-1-{2-[5-(4-Chloro-phenyl)-[1,3,4]oxadiazol-2-ylmethyl]-piperidin-1-yl}-1-[5-(4-fluoro-phenyl)-2-methyl-thiazol-4-yl]-methanone |
| 16 | (RS)-1-{2-[5-(2-Chloro-phenyl)-[1,3,4]oxadiazol-2-ylmethyl]-piperidin-1-yl}-1-[5-(4-fluoro-phenyl)-2-methyl-thiazol-4-yl]-methanone |
| 17 | (RS)-1-{2-[5-(2-Chloro-phenyl)-[1,3,4]oxadiazol-2-ylmethyl]-piperidin-1-yl}-1-[2-(3-methyl-[1,2,4]oxadiazol-5-yl)-phenyl]-methanone |
| 18 | (RS)-1-{2-[5-(2,3-Dichloro-phenyl)-[1,3,4]oxadiazol-2-ylmethyl]-piperidin-1-yl}-1-[5-(4-fluoro-phenyl)-2-methyl-thiazol-4-yl]-methanone |
| 19 | (RS)-1-[5-(4-Fluoro-phenyl)-2-methyl-thiazol-4-yl]-1-{2-[5-(2-fluoro-phenyl)-[1,3,4]oxadiazol-2-ylmethyl]-piperidin-1-yl}-methanone |
| 20 | (RS)-1-[2-(5-Benzofuran-4-yl-[1,3,4]oxadiazol-2-ylmethyl)-piperidin-1-yl]-1-[5-(4-fluoro-phenyl)-2-methyl-thiazol-4-yl]-methanone |
| 21 | (RS)-1-[4-(4-Fluoro-phenyl)-1-methyl-1H-pyrazol-3-yl]-1-{2-[5-(2-fluoro-phenyl)-[1,3,4]oxadiazol-2-ylmethyl]-piperidin-1-yl}-methanone |
| 22 | (RS)-1-[5-(4-Fluoro-phenyl)-2-methyl-2H-[1,2,3]triazol-4-yl]-1-{2-[5-(2-fluoro-phenyl)-[1,3,4]oxadiazol-2-ylmethyl]-piperidin-1-yl}-methanone |
| 23 | (RS)-1-{2-[5-(2-Fluoro-phenyl)-[1,3,4]oxadiazol-2-ylmethyl]-piperidin-1-yl}-1-naphthalen-1-yl-methanone |
| 24 | (RS)-1-{2-[5-(2,3-Difluoro-phenyl)-[1,3,4]oxadiazol-2-ylmethyl]-piperidin-1-yl}-1-[5-(4-fluoro-phenyl)-2-methyl-thiazol-4-yl]-methanone |
| 25 | (RS)-1-[4-(4-Fluoro-phenyl)-1-methyl-1H-pyrazol-3-yl]-1-[2-(5-phenyl-[1,3,4]oxadiazol-2-ylmethyl)-piperidin-1-yl]-methanone |
| 26 | (RS)-1-{2-[5-(2,5-Difluoro-phenyl)-[1,3,4]oxadiazol-2-ylmethyl]-piperidin-1-yl}-1-[5-(4-fluoro-phenyl)-2-methyl-thiazol-4-yl]-methanone |
| 27 | (RS)-1-{2-[5-(2,5-Difluoro-phenyl)-[1,3,4]oxadiazol-2-ylmethyl]-piperidin-1-yl}-1-[4-(4-fluoro-phenyl)-1H-pyrazol-3-yl]-methanone |
| 28 | (RS)-1-{2-[5-(2,5-Difluoro-phenyl)-[1,3,4]oxadiazol-2-ylmethyl]-piperidin-1-yl}-1-[4-(4-fluoro-phenyl)-1-methyl-1H-pyrazol-3-yl]-methanone |
| 29 | (RS)-1-{2-[5-(3,5-Difluoro-phenyl)-[1,3,4]oxadiazol-2-ylmethyl]-piperidin-1-yl}-1-[5-(4-fluoro-phenyl)-2-methyl-thiazol-4-yl]-methanone |
| 30 | (RS)-1-{2-[5-(3,5-Difluoro-phenyl)-[1,3,4]oxadiazol-2-ylmethyl]-piperidin-1-yl}-1-[5-(4-fluoro-phenyl)-thiazol-4-yl]-methanone |
| 31 | (RS)-1-{2-[5-(3,5-Difluoro-phenyl)-[1,3,4]oxadiazol-2-ylmethyl]-piperidin-1-yl}-1-[4-(4-fluoro-phenyl)-1H-pyrazol-3-yl]-methanone |

-continued

| | |
|---|---|
| 32 | (RS)-1-{2-[5-(3,5-Difluoro-phenyl)-[1,3,4]oxadiazol-2-ylmethyl-piperidin-1-yl}-1-[4-(4-fluoro-phenyl)-1-methyl-1H-pyrazol-3-yl]-methanone |
| 33 | (RS)-1-[5-(4-Fluoro-phenyl)-2-methyl-thiazol-4-yl]-1-{2-[5-(6-methyl-pyridin-2-yl)-[1,3,4]oxadiazol-2-ylmethyl]-piperidin-1-yl}-methanone |
| 34 | (RS)-1-[4-(4-Fluoro-phenyl)-1H-pyrazol-3-yl]-1-{2-[5-(6-methyl-pyridin-2-yl)-[1,3,4]oxadiazol-2-ylmethyl]-piperidin-1-yl}-methanone |
| 35 | (RS)-1-[4-(4-Fluoro-phenyl)-1-methyl-1H-pyrazol-3-yl]-1-{2-[5-(6-methyl-pyridin-2-yl)-[1,3,4]oxadiazol-2-ylmethyl]-piperidin-1-yl}-methanone |
| 36 | (RS)-1-{2-[5-(3-Fluoro-phenyl)-[1,3,4]oxadiazol-2-ylmethyl]-piperidin-1-yl}-1-[5-(4-fluoro-phenyl)-thiazol-4-yl]-methanone |
| 37 | (RS)-1-[5-(4-Fluoro-phenyl)-2-methyl-thiazol-4-yl]-1-[2-(5-furan-2-yl-[1,3,4]oxadiazol-2-ylmethyl)-piperidin-1-yl]-methanone |
| 38 | (RS)-1-[4-(4-Fluoro-phenyl)-1H-pyrazol-3-yl]-1-[2-(5-furan-2-yl-[1,3,4]oxadiazol-2-ylmethyl)-piperidin-1-yl]-methanone |
| 39 | (RS)-1-[4-(4-Fluoro-phenyl)-1-methyl-1H-pyrazol-3-yl]-1-[2-(5-furan-2-yl-[1,3,4]oxadiazol-2-ylmethyl)-piperidin-1-yl]-methanone |
| 40 | (RS)-1-[5-(4-Fluoro-phenyl)-2-methyl-2H-[1,2,3]triazol-4-yl]-1-[2-(5-furan-2-yl-[1,3,4]oxadiazol-2-ylmethyl)-piperidin-1-yl]-methanone |
| 41 | (RS)-1-{2-[5-(3-Fluoro-phenyl)-[1,3,4]oxadiazol-2-ylmethyl]-piperidin-1-yl}-1-[5-(4-fluoro-phenyl)-thiazol-4-yl]-methanone |
| 42 | (RS)-1-[5-(3-Fluoro-phenyl)-2-methyl-thiazol-4-yl]-1-{2-[5-(3-fluoro-phenyl)-[1,3,4]oxadiazol-2-ylmethyl]-piperidin-1-yl}-methanone |
| 43 | (RS)-1-[5-(2-Fluoro-phenyl)-2-methyl-thiazol-4-yl]-1-{2-[5-(3-fluoro-phenyl)-[1,3,4]oxadiazol-2-ylmethyl]-piperidin-1-yl}-methanone |
| 44 | (RS)-1-[5-(4-Fluoro-phenyl)-thiazol-4-yl]-1-[2-(5-phenyl-[1,3,4]oxadiazol-2-ylmethyl)-piperidin-1-yl]-methanone |
| 45 | (RS)-1-[5-(3-Fluoro-phenyl)-2-methyl-thiazol-4-yl]-1-[2-(5-phenyl-[1,3,4]oxadiazol-2-ylmethyl)-piperidin-1-yl]-methanone |
| 46 | (RS)-1-[5-(2-Fluoro-phenyl)-2-methyl-thiazol-4-yl]-1-[2-(5-phenyl-[1,3,4]oxadiazol-2-ylmethyl)-piperidin-1-yl]-methanone |
| 47 | (RS)-1-[5-(3-Fluoro-phenyl)-2-methyl-thiazol-4-yl]-1-{2-[5-(6-methyl-pyridin-2-yl)-[1,3,4]oxadiazol-2-ylmethyl]-piperidin-1-yl}-methanone |
| 48 | (RS)-1-[5-(2-Fluoro-phenyl)-2-methyl-thiazol-4-yl]-1-{2-[5-(6-methyl-pyridin-2-yl)-[1,3,4]oxadiazol-2-ylmethyl]-piperidin-1-yl}-methanone |
| 49 | (RS)-1-{2-[5-(2,3-Difluoro-phenyl)-[1,3,4]oxadiazol-2-ylmethyl]-piperidin-1-yl}-1-[4-(4-fluoro-phenyl)-1H-pyrazol-3-yl]-methanone |
| 50 | (RS)-1-{2-[5-(2,3-Difluoro-phenyl)-[1,3,4]oxadiazol-2-ylmethyl]-piperidin-1-yl}-1-[4-(4-fluoro-phenyl)-1-methyl-1H-pyrazol-3-yl]-methanone |
| 51 | 1-[5-(4-Fluoro-phenyl)-2-methyl-thiazol-4-yl]-1-[(S)-2-(5-phenyl-[1,3,4]oxadiazol-2-ylmethyl)-pyrrolidin-1-yl]-methanone |
| 52 | (RS)-1-[5-(3-Fluoro-phenyl)-2-methyl-thiazol-4-yl]-1-[(S)-2-(5-phenyl-[1,3,4]oxadiazol-2-ylmethyl)-pyrrolidin-1-yl]-methanone |
| 53 | (RS)-1-[5-(2-Fluoro-phenyl)-2-methyl-thiazol-4-yl]-1-[(S)-2-(5-phenyl-[1,3,4]oxadiazol-2-ylmethyl)-pyrrolidin-1-yl]-methanone |
| 54 | (RS)-1-[5-(4-Fluoro-phenyl)-2-methyl-thiazol-4-yl]-1-{2-[4-(4-fluoro-phenyl)-oxazol-2-ylmethyl]-piperidin-1-yl}-methanone |
| 55 | (RS)-1-[5-(4-Fluoro-phenyl)-2-methyl-thiazol-4-yl]-1-{2-[4-(2-methoxy-phenyl)-oxazol-2-ylmethyl]-piperidin-1-yl}-methanone |
| 56 | (RS)-1-[5-(4-Fluoro-phenyl)-2-methyl-thiazol-4-yl]-1-{2-[4-(3-fluoro-phenyl)-oxazol-2-ylmethyl]-piperidin-1-yl}-methanone |
| 57 | (RS)-1-[5-(4-Fluoro-phenyl)-2-methyl-thiazol-4-yl]-1-{2-[4-(2-fluoro-phenyl)-oxazol-2-ylmethyl]-piperidin-1-yl}-methanone |
| 58 | (RS)-1-[5-(4-Fluoro-phenyl)-2-methyl-thiazol-4-yl]-1-[2-(5-methyl-4-phenyl-oxazol-2-ylmethyl)-piperidin-1-yl]-methanone |
| 59 | (RS)-2-(5-(4-Fluorophenyl)-furan-2-ylmethyl)-1-((5-(4-fluorophenyl)-2-methyl-thiazol-4-yl)carbonyl-piperidine |
| 60 | (RS)-1-[2-(4-Fluoro-phenyl)-5-methyl-2H-pyrazol-3-yl]-1-[2-(4-phenyl-oxazol-2-ylmethyl)-piperidin-1-yl]-methanone |
| 61 | (RS)-1-[5-(4-Fluoro-phenyl)-2-methyl-2H-[1,2,3]triazol-4-yl]-1-[2-(4-phenyl-oxazol-2-ylmethyl)-piperidin-1-yl]-methanone |
| 62 | (RS)-1-Naphthalen-1-yl-1-[2-(4-phenyl-oxazol-2-ylmethyl)-piperidin-1-yl]-methanone |
| 63 | (RS)-1-(5-Bromo-2-methoxy-phenyl)-1-[2-(4-phenyl-oxazol-2-ylmethyl)-piperidin-1-yl]-methanone |
| 64 | (RS)-1-[5-(4-Fluoro-phenyl)-2-methyl-thiazol-4-yl]-1-[2-(5-phenyl-1H-imidazol-2-ylmethyl)-piperidin-1-yl]-methanone |
| 65 | (RS)-1-[5-(4-Fluoro-phenyl)-2-methyl-thiazol-4-yl]-1-{2-[3-(4-fluoro-phenyl)-[1,2,4]oxadiazol-5-ylmethyl]-piperidin-1-yl}-methanone |
| 66 | (RS)-1-[5-(4-Fluoro-phenyl)-2-methyl-thiazol-4-yl]-1-[3-(5-phenyl-[1,3,4]oxadiazol-2-ylmethyl)-morpholin-4-yl]-methanone |
| 67 | (RS)-1-[5-(4-Fluoro-phenyl)-2-methyl-thiazol-4-yl]-1-[3-(4-phenyl-oxazol-2-ylmethyl)-morpholin-4-yl]-methanone |
| 68 | (RS)-1-[5-(4-Fluoro-phenyl)-2-methyl-thiazol-4-yl]-1-[3-(4-phenyl-1H-imidazol-2-ylmethyl)-morpholin-4-yl]-methanone |
| 69 | (RS)-1-[5-(4-Fluoro-phenyl)-2-methyl-thiazol-4-yl]-1-{2-[5-(4-fluoro-phenyl)-oxazol-2-ylmethyl]-piperidin-1-yl}-methanone |
| 70 | (RS)-1-[5-(4-Fluoro-phenyl)-2-methyl-thiazol-4-yl]-1-[2-(4-phenyl-oxazol-2-ylmethyl)-piperidin-1-yl]-methanone |
| 71 | (RS)-1-{2-[5-(4-Fluoro-phenyl)-oxazol-2-ylmethyl]-piperidin-1-yl}-1-naphthalen-1-yl-methanone |

-continued

| | |
|---|---|
| 72 | (RS)-1-(3,5-Dimethoxy-phenyl)-1-{2-[5-(4-fluoro-phenyl)-oxazol-2-ylmethyl]-piperidin-1-yl}-methanone |
| 73 | (RS)-1-[2-(4-Fluoro-phenyl)-5-methyl-2H-pyrazol-3-yl]-1-{2-[5-(4-fluoro-phenyl)-oxazol-2-ylmethyl]-piperidin-1-yl}-methanone |
| 74 | (RS)-1-[5-(4-Fluoro-phenyl)-2-methyl-2H-[1,2,3]triazol-4-yl]-1-{2-[5-(4-fluoro-phenyl)-oxazol-2-ylmethyl]-piperidin-1-yl}-methanone |
| 75 | (RS)-1-[4-(4-Fluoro-phenyl)-1-methyl-1H-pyrazol-3-yl]-1-{2-[5-(4-fluoro-phenyl)-oxazol-2-ylmethyl]-piperidin-1-yl}-methanone |
| 76 | (RS)-1-{2-[5-(4-Fluoro-phenyl)-oxazol-2-ylmethyl]-piperidin-1-yl}-1-[5-(4-fluoro-phenyl)-thiazol-4-yl]-methanone |
| 77 | (RS)-1-[5-(4-Fluoro-phenyl)-2-methyl-thiazol-4-yl]-1-[2-(5-phenyl-oxazol-2-ylmethyl)-piperidin-1-yl]-methanone |
| 78 | (RS)-1-[2-(3-Methyl-[1,2,4]oxadiazol-5-yl)-phenyl]-1-[2-(5-phenyl-oxazol-2-ylmethyl)-piperidin-1-yl]-methanone |
| 79 | (RS)-1-(2-Iodo-phenyl)-1-[2-(5-phenyl-oxazol-2-ylmethyl)-piperidin-1-yl]-methanone |
| 181 | (RS)-1-{2-[5-(2,3-Difluoro-phenyl)-[1,3,4]oxadiazol-2-ylmethyl]-piperidin-1-yl}-1-[5-(4-fluoro-phenyl)-2-methyl-2H-[1,2,3]triazol-4-yl]-methanone | and pharmaceutically acceptable salts thereof.

Additional compounds of formula (I) can be selected from:

| | |
|---|---|
| 80 | 1-{(S)-2-[5-(4-Fluoro-phenyl)-1H-imidazol-2-ylmethyl]-pyrrolidin-1-yl}-1-[5-(4-fluoro-phenyl)-2-methyl-thiazol-4-yl]-methanone |
| 81 | 1-{(S)-2-[5-(4-Fluoro-phenyl)-1H-imidazol-2-ylmethyl]-pyrrolidin-1-yl}-1-[4-(4-fluoro-phenyl)-1-methyl-1H-pyrazol-3-yl]-methanone |
| 82 | 1-{(S)-2-[5-(4-Fluoro-phenyl)-1H-imidazol-2-ylmethyl]-pyrrolidin-1-yl}-1-[4-(4-fluoro-phenyl)-1H-pyrazol-3-yl]-methanone |
| 83 | (RS)-1-{2-[5-(4-Fluoro-phenyl)-1H-imidazol-2-ylmethyl]-piperidin-1-yl}-1-[5-(4-fluoro-phenyl)-2-methyl-thiazol-4-yl]-methanone |
| 84 | (RS)-1-{2-[5-(4-Fluoro-phenyl)-1H-imidazol-2-ylmethyl]-piperidin-1-yl}-1-[4-(4-fluoro-phenyl)-1-methyl-1H-pyrazol-3-yl]-methanone |
| 85 | (RS)-1-{2-[5-(4-Fluoro-phenyl)-1H-imidazol-2-ylmethyl]-piperidin-1-yl}-1-[4-(4-fluoro-phenyl)-1H-pyrazol-3-yl]-methanone |
| 86 | (RS)-1-{2-[5-(4-Fluoro-phenyl)-1H-imidazol-2-ylmethyl]-piperidin-1-yl}-1-(2-methoxy-pyridin-3-yl)-methanone |
| 87 | (RS)-1-{2-[5-(4-Fluoro-phenyl)-1H-imidazol-2-ylmethyl]-piperidin-1-yl}-1-isoquinolin-3-yl-methanone |
| 88 | (RS)-1-{2-[5-(4-Fluoro-phenyl)-1H-imidazol-2-ylmethyl]-piperidin-1-yl}-1-[1,8]naphthyridin-2-yl-methanone |
| 89 | (RS)-1-[1-(2-Dimethylamino-ethyl)-4-(4-fluoro-phenyl)-1H-pyrazol-3-yl]-1-{2-[4-(4-fluoro-phenyl)-1H-imidazol-2-ylmethyl]-piperidin-1-yl}-methanone |
| 90 | (RS)-1-[5-(4-Fluoro-phenyl)-2-hydroxymethyl-thiazol-4-yl]-1-{2-[5-(4-fluoro-phenyl)-1H-imidazol-2-ylmethyl]-piperidin-1-yl}-methanone |
| 91 | (RS)-1-{2-[4-(4-Fluoro-phenyl)-1H-imidazol-2-ylmethyl[-piperidin-1-yl}-1-[5-(4-fluoro-phenyl)-2-methyl-2H-[1,2,3]triazol-4-yl]-methanone |
| 92 | (RS)-1-{2-[4-(4-Fluoro-phenyl)-1H-imidazol-2-ylmethyl]-piperidin-1-yl}-1-[2-(3-methyl-[1,2,4]oxadiazol-5-yl)-phenyl]-methanone |
| 93 | (RS)-1-[5-(4-Fluoro-phenyl)-2-methyl-thiazol-4-yl]-1-{2-[5-(2-methoxyphenyl)-1H-imidazol-2-ylmethyl]-piperidin-1-yl}-methanone |
| 94 | (RS)-1-[5-(4-Fluoro-phenyl)-2-methyl-thiazol-4-yl]-1-{2-[5-(2-fluorophenyl)-1H-imidazol-2-ylmethyl]-piperidin-1-yl}-methanone |
| 95 | (RS)-1-[5-(4-Fluoro-phenyl)-2-methyl-thiazol-4-yl]-1-{2-[5-(2-bromophenyl)-1H-imidazol-2-ylmethyl]-piperidin-1-yl}-methanone |
| 96 | (RS)-2-[2-(1-{1-[5-(4-Fluoro-phenyl)-2-methyl-thiazol-4-yl]-methanoyl}-piperidin-2-ylmethyl)-3H-imidazol-4-yl]-benzonitrile |
| 97 | (RS)-1-{2-[4-Bromo-5-(4-fluoro-phenyl)-1H-imidazol-2-ylmethyl]-piperidin-1-yl}-1-[5-(4-fluoro-phenyl)-2-methyl-thiazol-4-yl]-methanone |
| 98 | (RS)-5-(4-Fluoro-phenyl)-2-(1-{1-[5-(4-fluoro-phenyl)-2-methyl-thiazol-4-yl]-methanoyl}-piperidin-2-ylmethyl)-3H-imidazole-4-carbonitrile |
| 102 | (RS)-1-(2-Ethoxy-phenyl)-1-[2-(4-phenyl-oxazol-2-ylmethyl)-piperidin-1-yl]-methanone |
| 103 | (RS)-1-[5-(4-Fluoro-phenyl)-2-hydroxymethyl-thiazol-4-yl]-1-[2-(4-phenyl-oxazol-2-ylmethyl)-piperidin-1-yl]-methanone |
| 104 | (RS)-1-[5-(4-Fluoro-phenyl)-2-hydroxymethyl-thiazol-4-yl]-1-[2-(5-phenyl-1H-imidazol-2-ylmethyl)-piperidin-1-yl]-methanone |
| 105 | (RS)-1-[5-(4-Fluoro-phenyl)-2-methyl-thiazol-4-yl]-1-{2-[5-(4-fluoro-phenyl)-4H-[1,2,4]triazol-3-ylmethyl]-piperidin-1-yl}-methanone |
| 106 | (RS)-1-{2-[5-(4-Fluoro-phenyl)-4H-[1,2,4]triazol-3-ylmethyl]-piperidin-1-yl}-1-isoquinolin-3-yl-methanone |
| 107 | (RS)-1-{2-[3-(3-Dimethylamino-propoxy)-phenyl]-thiophen-3-yl}-1-{2-[4-(4-fluoro-phenyl)-1H-imidazol-2-ylmethyl]-piperidin-1-yl}-methanone |
| 108 | (RS)-1-[5-(4-Fluoro-phenyl)-2-methyl-thiazol-4-yl]-1-{2-[5-(3-methoxy-phenyl)-1H-imidazol-2-ylmethyl]-piperidin-1-yl}-methanone |

-continued

| | |
|---|---|
| 109 | (RS)-1-[4-(4-Fluoro-phenyl)-1-methyl-1H-pyrazol-3-yl]-1-{2-[5-(3-methoxy-phenyl)-1H-imidazol-2-ylmethyl]-piperidin-1-yl}-methanone |
| 110 | (RS)-1-{2-[5-(3-Chloro-phenyl)-1H-imidazol-2-ylmethyl]-piperidin-1-yl}-1-[5-(4-fluoro-phenyl)-2-methyl-thiazol-4-yl]-methanone |
| 111 | (RS)-1-{2-[5-(3-Chloro-phenyl)-1H-imidazol-2-ylmethyl]-piperidin-1-yl}-1-[4-(4-fluoro-phenyl)-1-methyl-1H-pyrazol-3-yl]-methanone |
| 112 | (RS)-3-[2-(1-{1-[5-(4-Fluoro-phenyl)-2-methyl-thiazol-4-yl]-methanoyl}-piperidin-2-ylmethyl)-3H-imidazol-4-yl]-benzonitrile |
| 113 | (RS)-3-[2-(1-{1-[4-(4-Fluoro-phenyl)-1-methyl-1H-pyrazol-3-yl]-methanoyl}-piperidin-2-ylmethyl)-3H-imidazol-4-yl]-benzonitrile |
| 114 | (RS)-1-[5-(2-Fluoro-phenyl)-2-methyl-thiazol-4-yl]-1-[2-(5-phenyl-1H-imidazol-2-ylmethyl)-piperidin-1-yl]-methanone |
| 115 | (RS)-1-[5-(3-Fluoro-phenyl)-2-methyl-thiazol-4-yl]-1-[2-(5-phenyl-1H-imidazol-2-ylmethyl)-piperidin-1-yl]-methanone |
| 116 | (RS)-1-(2-Methyl-5-phenyl-thiazol-4-yl)-1-[2-(5-phenyl-1H-imidazol-2-ylmethyl)-piperidin-1-yl]-methanone |
| 117 | (RS)-1-{5-[3-(3-Dimethylamino-propoxy)-phenyl]-2-methyl-thiazol-4-yl}-1-[2-(5-phenyl-1H-imidazol-2-ylmethyl)-piperidin-1-yl]-methanone |
| 118 | (RS)-1-{5-[3-(4-Dimethylamino-butoxy)-phenyl]-2-methyl-thiazol-4-yl}-1-[2-(5-phenyl-1H-imidazol-2-ylmethyl)-piperidin-1-yl]-methanone |
| 119 | (RS)-1-{5-[3-(2-Dimethylamino-ethoxy)-phenyl]-2-methyl-thiazol-4-yl}-1-[2-(5-phenyl-1H-imidazol-2-ylmethyl)-piperidin-1-yl]-methanone |
| 120 | (RS)-1-[5-(4-Fluoro-phenyl)-2-methyl-thiazol-4-yl]-1-{2-[5-(4-fluoro-phenyl)-tetrazol-2-ylmethyl]-piperidin-1-yl}-methanone |
| 121 | (RS)-1-{2-[5-(4-Fluoro-phenyl)-tetrazol-2-ylmethyl]-piperidin-1-yl}-1-[5-(4-fluoro-phenyl)-thiazol-4-yl]-methanone |
| 122 | (RS)-1-[4-(4-Fluoro-phenyl)-1H-pyrazol-3-yl]-1-{2-[5-(4-fluoro-phenyl)-tetrazol-2-ylmethyl]-piperidin-1-yl}-methanone |
| 123 | (RS)-1-[4-(4-Fluoro-phenyl)-1-methyl-1H-pyrazol-3-yl]-1-{2-[5-(4-fluoro-phenyl)-tetrazol-2-ylmethyl]-piperidin-1-yl}-methanone |
| 124 | (RS)-1-[4-(4-Fluoro-phenyl)-2-methyl-2H-pyrazol-3-yl]-1-{2-[5-(4-fluoro-phenyl)-tetrazol-2-ylmethyl]-piperidin-1-yl}-methanone |
| 144 | (RS)-1-[5-(4-Fluoro-phenyl)-2-methyl-thiazol-4-yl]-1-[2-(4-phenyl-imidazol-1-ylmethyl)-piperidin-1-yl]-methanone |
| 145 | (RS)-1-[5-(4-Fluoro-phenyl)-thiazol-4-yl]-1-[2-(4-phenyl-imidazol-1-ylmethyl)-piperidin-1-yl]-methanone |
| 146 | (RS)-1-[4-(4-Fluoro-phenyl)-1-methyl-1H-pyrazol-3-yl]-1-[2-(4-phenyl-imidazol-1-ylmethyl)-piperidin-1-yl]-methanone |
| 147 | (RS)-1-[5-(4-Fluoro-phenyl)-2-methyl-thiazol-4-yl]-1-{2-[3-(4-fluoro-phenyl)-pyrazol-1-ylmethyl]-piperidin-1-yl}-methanone |
| 148 | (RS)-1-(5-Bromo-2-methoxy-phenyl)-1-{2-[3-(4-fluoro-phenyl)-pyrazol-1-ylmethyl]-piperidin-1-yl}-methanone |
| 149 | (RS)-1-[5-(4-Fluoro-phenyl)-2-methyl-2H-[1,2,3]triazol-4-yl]-1-{2-[3-(4-fluoro-phenyl)-pyrazol-1-ylmethyl]-piperidin-1-yl}-methanone |
| 150 | (RS)-1-[5-(4-Fluoro-phenyl)-2-methyl-oxazol-4-yl]-1-{2-[3-(4-fluoro-phenyl)-pyrazol-1-ylmethyl]-piperidin-1-yl}-methanone |
| 151 | (RS)-1-{2-[3-(4-Fluoro-phenyl)-pyrazol-1-ylmethyl]-piperidin-1-yl}-1-[2-(3-methyl-[1,2,4]oxadiazol-5-yl)-phenyl]-methanone |
| 152 | (RS)-1-[5-(4-Fluoro-phenyl)-2-methyl-thiazol-4-yl]-1-[2-(4-phenyl-thiazol-2-ylmethyl)-piperidin-1-yl]-methanone |
| 153 | (R)-1-[5-(4-Fluoro-phenyl)-2-methyl-thiazol-4-yl]-1-[3-(4-phenyl-oxazol-2-ylmethyl)-morpholin-4-yl]-methanone and (S)-(R)-1-[5-(4-Fluoro-phenyl)-2-methyl-thiazol-4-yl]-1-[3-(4-phenyl-oxazol-2-ylmethyl)-morpholin-4-yl]-methanone |
| 154 | (RS)-1-{2-[5-(2,5-Dimethyl-2H-pyrazol-3-yl)-[1,3,4]oxadiazol-2-ylmethyl]-piperidin-1-yl}-1-[5-(4-fluoro-phenyl)-2-methyl-thiazol-4-yl]-methanone |
| 155 | (RS)-1-[2-(4,5-Diphenyl-1H-imidazol-2-ylmethyl)-piperidin-1-yl]-1-[5-(4-fluoro-phenyl)-2-methyl-thiazol-4-yl]-methanone |
| 156 | (RS)-1-{2-[4-(4-Fluoro-phenyl)-1-methyl-1H-imidazol-2-ylmethyl]-piperidin-1-yl}-1-[5-(4-fluoro-phenyl)-2-methyl-thiazol-4-yl]-methanone |
| 157 | (RS)-1-[2-(5-Benzofuran-2-yl-[1,3,4]oxadiazol-2-ylmethyl)-piperidin-1-yl]-1-[5-(3-fluoro-phenyl)-2-methyl-thiazol-4-yl]-methanone |
| 158 | (RS)-1-[5-(4-Fluoro-phenyl)-2-methyl-thiazol-4-yl]-1-[2-(4-pyridin-2-yl-oxazol-2-ylmethyl)-piperidin-1-yl]-methanone |
| 159 | (RS)-1-{2-[5-(3,4-Difluoro-phenyl)-1H-imidazol-2-ylmethyl]-piperidin-1-yl}-1-[5-(4-fluoro-phenyl)-2-methyl-thiazol-4-yl]-methanone |
| 160 | (RS)-1-{2-[5-(3-Fluoro-phenyl)-1H-imidazol-2-ylmethyl]-piperidin-1-yl}-1-[5-(4-fluoro-phenyl)-2-methyl-thiazol-4-yl]-methanone |
| 161 | (RS)-1-[5-(4-Fluorophenyl)-2-methylthiazol-4-yl]-1-{2-[5-(4-fluorophenyl)-1H-pyrazol-3-ylmethyl]-piperidin-1-yl}-methanone |
| 162 | (RS)-1-{2-[4-(4-Fluorophenyl)-1H-imidazol-2-ylmethyl]-piperazin-1-yl}-1-[5-(4-fluorophenyl)-2-methylthiazol-4-yl]-methanone |
| 163 | 1-[5-(4-Fluorophenyl)-2-methyl-thiazol-4-yl]-1-{2-[4-(4-fluorophenyl)-oxazol-2-ylmethyl]-piperazin-1-yl}-methanone | and pharmaceutically acceptable salts thereof.

Further compounds of formula (I) can be selected from:

| | |
|---|---|
| 99 | (RS)-1-[4-(4-Fluoro-phenyl)-1-methyl-1H-pyrazol-3-yl]-1-{2-[4-(4-fluoro-phenyl)-oxazol-2-ylmethyl]-piperidin-1-yl}-methanone |
| 100 | (RS)-1-{2-[4-(4-Fluoro-phenyl)-oxazol-2-ylmethyl]-piperidin-1-yl}-1-[4-(4-fluoro-phenyl)-1H-pyrazol-3-yl]-methanone |
| 101 | (RS)-1-{2-[4-(4-Fluoro-phenyl)-oxazol-2-ylmethyl]-piperidin-1-yl}-1-quinolin-2-yl-methanone |
| 125 | (RS)-1-{2-[5-(3-Fluoro-phenyl)-[1,3,4]oxadiazol-2-ylmethyl]-piperidin-1-yl}-1-(3-thiophen-2-yl-phenyl)-methanone |
| 126 | (RS)-1-{2-[5-(3-Fluoro-phenyl)-[1,3,4]oxadiazol-2-ylmethyl]-piperidin-1-yl}-1-(3-thiophen-3-yl-phenyl)-methanone |
| 127 | (RS)-1-{2-[5-(3-Fluoro-phenyl)-[1,3,4]oxadiazol-2-ylmethyl]-piperidin-1-yl}-1-(2-pyrazol-1-yl-phenyl)-methanone |
| 128 | (RS)-2'-(1-{2-[5-(3-Fluoro-phenyl)-[1,3,4]oxadiazol-2-ylmethyl]-piperidin-1-yl}-methanoyl)-biphenyl-4-carbonitrile |
| 129 | (RS)-1-{2-[5-(3-Fluoro-phenyl)-[1,3,4]oxadiazol-2-ylmethyl]-piperidin-1-yl}-1-(4-methoxy-biphenyl-3-yl)-methanone |
| 130 | (RS)-1-{2-[5-(3-Fluoro-phenyl)-[1,3,4]oxadiazol-2-ylmethyl]-piperidin-1-yl}-1-(2-pyrrol-1-yl-phenyl)-methanone |
| 131 | (RS)-1-Dibenzofuran-4-yl-1-{2-[5-(3-fluoro-phenyl)-[1,3,4]oxadiazol-2-ylmethyl]-piperidin-1-yl}-methanone |
| 132 | (RS)-1-{2-[5-(3-Fluoro-phenyl)-[1,3,4]oxadiazol-2-ylmethyl]-piperidin-1-yl}-1-(2-methoxy-4-methyl-phenyl)-methanone |
| 133 | (RS)-1-(2-Ethoxy-4-methyl-phenyl)-1-{2-[5-(3-fluoro-phenyl)-[1,3,4]oxadiazol-2-ylmethyl]-piperidin-1-yl}-methanone |
| 134 | (RS)-1-(3,5-Dichloro-2-methoxy-phenyl)-1-{2-[5-(3-fluoro-phenyl)-[1,3,4]oxadiazol-2-ylmethyl]-piperidin-1-yl}-methanone |
| 135 | (RS)-1-{2-[5-(3-Fluoro-phenyl)-[1,3,4]oxadiazol-2-ylmethyl]-piperidin-1-yl}-1-(1-methoxy-naphthalen-2-yl)-methanone |
| 136 | (RS)-4-Ethoxy-2-ethyl-5-(1-{2-[5-(3-fluoro-phenyl)-[1,3,4]oxadiazol-2-ylmethyl]-piperidin-1-yl}-methanoyl)-benzonitrile |
| 137 | (RS)-4-Ethoxy-5-(1-{2-[5-(3-fluoro-phenyl)-[1,3,4]oxadiazol-2-ylmethyl]-piperidin-1-yl}-methanoyl)-2-methyl-benzonitrile |
| 138 | (RS)-1-{2-[5-(3-Fluoro-phenyl)-[1,3,4]oxadiazol-2-ylmethyl]-piperidin-1-yl}-(4'-methoxy-4-nitro-biphenyl-2-yl)-methanone |
| 139 | (RS)-1-{2-[5-(3-Fluoro-phenyl)-[1,3,4]oxadiazol-2-ylmethyl]-piperidin-1-yl}-1-(2'-methyl-4-nitro-biphenyl-2-yl)-methanone |
| 140 | (RS)-1-{2-[5-(3-Fluoro-phenyl)-[1,3,4]oxadiazol-2-ylmethyl]-piperidin-1-yl}-1-(4-nitro-biphenyl-2-yl)-methanone |
| 141 | (RS)-1-Benzofuran-7-yl-1-{2-[5-(3-fluoro-phenyl)-[1,3,4]oxadiazol-2-ylmethyl]-piperidin-1-yl}-methanone |
| 142 | (RS)-1-(5-Bromo-4-ethyl-2-methoxy-phenyl)-1-{2-[5-(3-fluoro-phenyl)-[1,3,4]oxadiazol-2-ylmethyl]-piperidin-1-yl}-methanone |
| 143 | (RS)-1-[1-Ethyl-4-(4-fluoro-phenyl)-1H-pyrazol-3-yl]-1-[2-(5-phenyl-[1,3,4]oxadiazol-2-ylmethyl)-piperidin-1-yl]-methanone |
| 164 | (RS)-1-[3-(5-Bromo-4-phenyl-oxazol-2-ylmethyl)-morpholin-4-yl]-1-[5-(4-fluoro-phenyl)-2-methyl-thiazol-4-yl]-methanone |
| 165 | (RS)-1-[2-(5-Chloro-4-phenyl-oxazol-2-ylmethyl)-piperidin-1-yl]-1-[5-(4-fluoro-phenyl)-2-methyl-thiazol-4-yl]-methanone |
| 166 | 1-[5-(4-Fluoro-phenyl)-2-methyl-thiazol-4-yl]-1-[(S)-2-(5-phenyl-4H-[1,2,4]triazol-3-ylmethyl)-pyrrolidin-1-yl]-methanone |
| 167 | (RS)-1-[2-(5-Bromo-4-phenyl-oxazol-2-ylmethyl)-piperidin-1-yl]-1-[5-(4-fluoro-phenyl)-2-methyl-thiazol-4-yl]-methanone |
| 168 | (RS)-1-(2-Methyl-5-phenyl-thiazol-4-yl)-1-[2-(4-phenyl-oxazol-2-ylmethyl)-piperidin-1-yl]-methanone |
| 169 | (RS)-1-[1-(2-Dimethylamino-ethyl)-4-(4-fluoro-phenyl)-1H-pyrazol-3-yl]-1-[2-(4-phenyl-oxazol-2-ylmethyl)-piperidin-1-yl]-methanone |
| 170 | (RS)-2-(1-{1-[5-(4-Fluoro-phenyl)-2-methyl-thiazol-4-yl]-methanoyl}-piperidin-2-ylmethyl)-4-phenyl-oxazole-5-carbonitrile |
| 171 | (RS)-1-[2-(5-Bromo-4-phenyl-oxazol-2-ylmethyl)-piperidin-1-yl]-1-(2-methyl-5-phenyl-thiazol-4-yl)-methanone |
| 172 | 1-[5-(4-Fluoro-phenyl)-2-methyl-thiazol-4-yl]-1-[(S)-2-(4-phenyl-oxazol-2-ylmethyl)-pyrrolidin-1-yl]-methanone |
| 173 | 1-[(S)-2-(5-Bromo-4-phenyl-oxazol-2-ylmethyl)-pyrrolidin-1-yl]-1-[5-(4-fluoro-phenyl)-2-methyl-thiazol-4-yl]-methanone |
| 174 | (RS)-1-[5-(4-Chloro-phenyl)-2-methyl-thiazol-4-yl]-1-[2-(4-phenyl-oxazol-2-ylmethyl)-piperidin-1-yl]-methanone |
| 175 | (RS)-1-[4-(4-Fluoro-phenyl)-1-methyl-1H-pyrazol-3-yl]-1-[2-(4-phenyl-thiazol-2-ylmethyl)-piperidin-1-yl]-methanone |
| 176 | (RS)-1-{2-[4-(2-Bromo-phenyl)-oxazol-2-ylmethyl]-piperidin-1-yl}-1-[5-(4-fluoro-phenyl)-2-methyl-thiazol-4-yl]-methanone |
| 177 | (RS)-2-[2-(1-{1-[5-(4-Fluoro-phenyl)-2-methyl-thiazol-4-yl]-methanoyl}-piperidin-2-ylmethyl)-oxazol-4-yl]-benzonitrile |
| 178 | (RS)-1-[5-(4-Fluoro-phenyl)-2-methyl-thiazol-4-yl]-1-{2-[4-(2-fluoro-phenyl)-thiazol-2-ylmethyl]-piperidin-1-yl}-methanone |
| 179 | (RS)-1-[5-(4-Fluoro-phenyl)-2-methyl-thiazol-4-yl]-1-{2-[4-(3-fluoro-phenyl)-thiazol-2-ylmethyl]-piperidin-1-yl}-methanone |
| 180 | (RS)-1-{2-[4-(3-Fluoro-phenyl)-thiazol-2-ylmethyl]-piperidin-1-yl}-1-(2-methyl-5-phenyl-thiazol-4-yl)-methanone | and pharmaceutically acceptable salts thereof.

When a halogen atom is present in the compound of formula (I) it may be fluorine, chlorine, bromine or iodine, preferably fluorine.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

When used herein the term aryl means a 5- to 6-membered aromatic ring, for example phenyl, or a 7 to 12 membered bicyclic ring system where at least one of the rings is aromatic, for example naphthyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoismers, including mixtures thereof. The different isomeric forms may be separated or resolved one from the other by conventional methods, or any given isomer may be example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail some synthetic routes to compounds of the invention

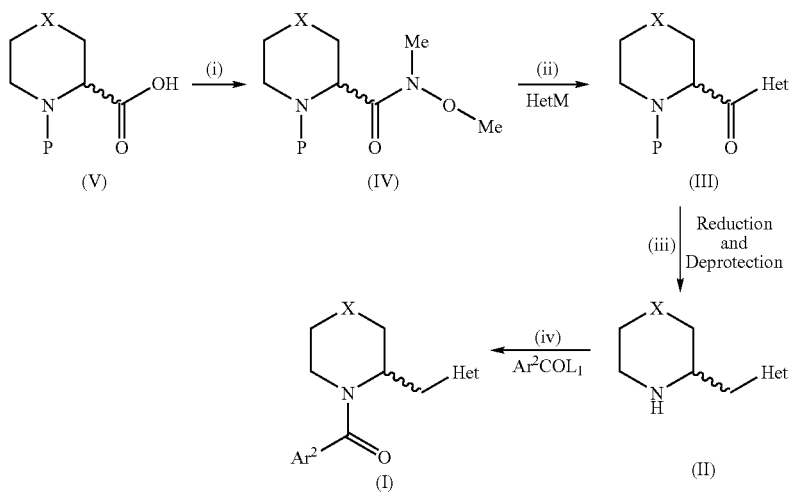

Scheme 1 obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for wherein X, Het and $Ar^2$ are as defined for compounds of formula (I), P is a protecting group and M is a metal, for example, lithium.

Examples of suitable leaving groups $L^1$ include halogen, OC(=O)alkyl and OC(=O)O-alkyl. The transformation (II) to (I) may be carried out in an inert solvent such as dichloromethane, in the presence of a base such as triethylamine. Alternatively this step may be carried out when $L^1$ represents hydroxy, in which case reaction with (II) takes place in an inert solvent such as dichloromethane in the presence of a diimide coupling reagent such as 1-ethyl-3-(3-dimethylaminopropyl)carbodiimide hydrochloride, and an activator such as 1-hydroxybenzotriazole.

Examples of protecting groups P include t-butyloxycarbonyl, trifluoroacetyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

Compounds of formula (V) are known in the literature or can be prepared by known methods.

Compounds of formula (I) when Het is a 5-aryl-1,3,4-oxadiazole can be prepared by the process described in scheme 2a, or 2b, where X, Ar² and R² are as defined for compounds of formula (I).

Compounds of formula (I) when Het is substituted 3-(1,2,4-oxadiazole) can be prepared by the process described in scheme 3 where X, Ar² and R² are as defined for compounds of formula (I).

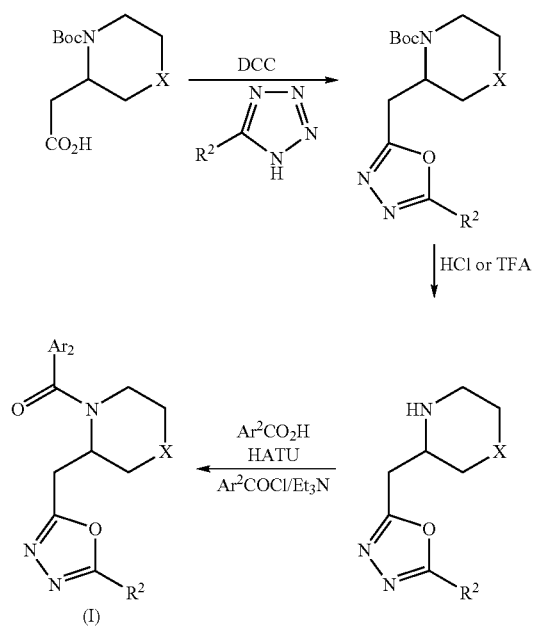

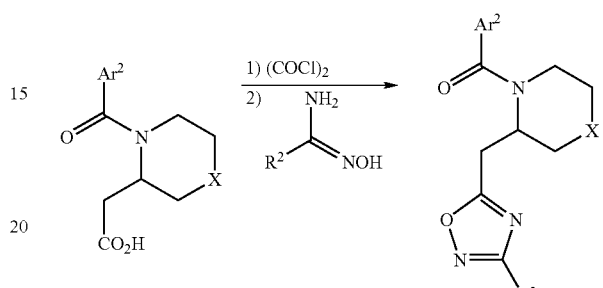

Compounds of formula (I) when Het is a 2-(4-aryloxazole) can be prepared by the process described in Scheme 4 where X, Ar² and R² are as defined for compounds of formula (I).

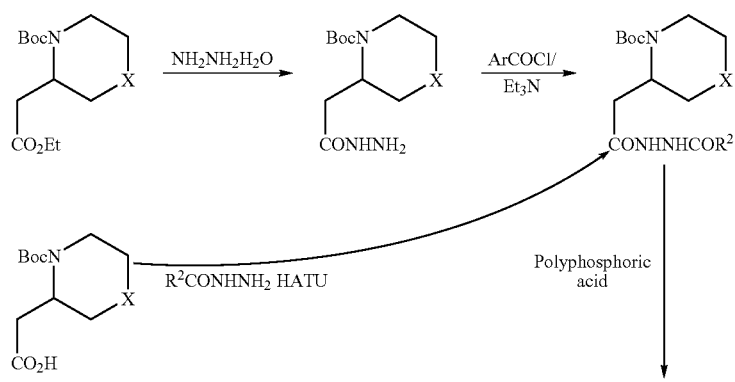

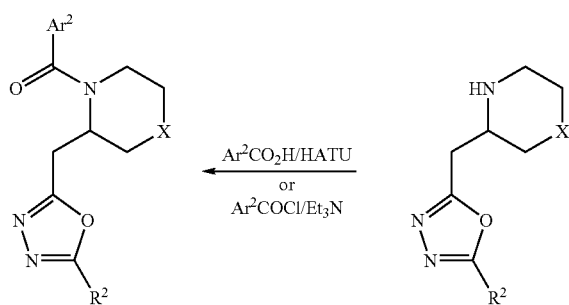

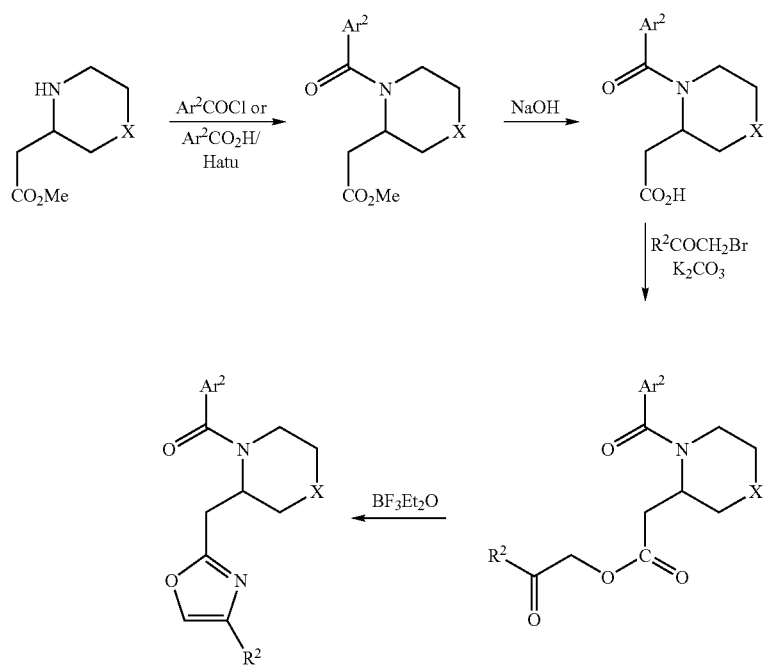

Compounds of formula (I) when Het is a 2-5-aryloxazole) can be prepared by the process described in Scheme 5 where X, Ar² and R² are as defined for compounds of formula (I).

Compounds of formula (I) where Het is a 2-(4-substituted imidazole) can be prepared by the process described in scheme 6 where X, Ar² and R² are as defined for compounds of formula (I).

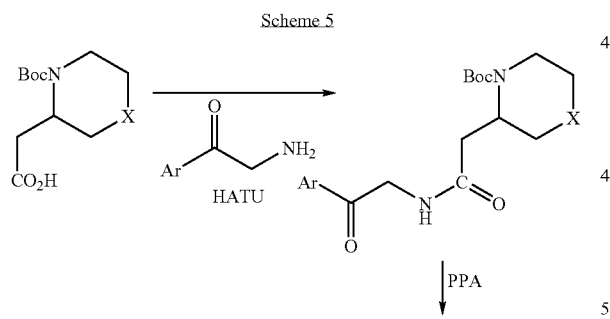

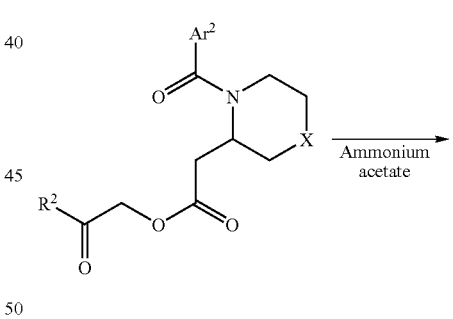

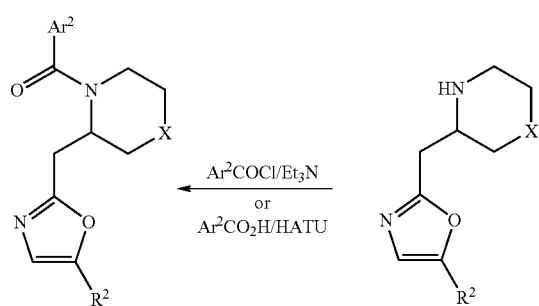

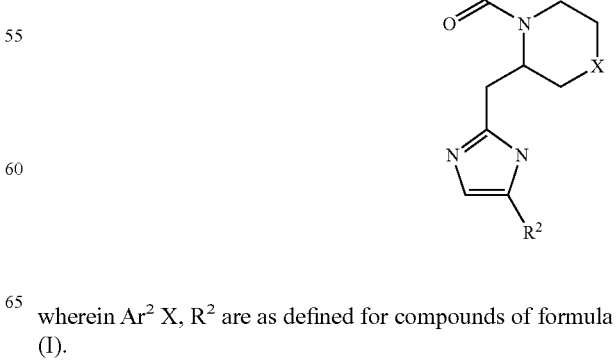

wherein Ar² X, R² are as defined for compounds of formula (I).

Scheme 7

Compounds of formula (I) wherein the Het group is linked to the cyclic ring through a nitrogen in the Het group, can be prepared by the process defined in scheme 7 wherein X, Ar² and R² are as defined for compounds of formula (I).

Compounds of formula (I) where Het is a 2-(4-arylthiazole) can be prepared by the process described in Scheme 9 where X, Ar² and R² are as defined for compounds of formula (I).

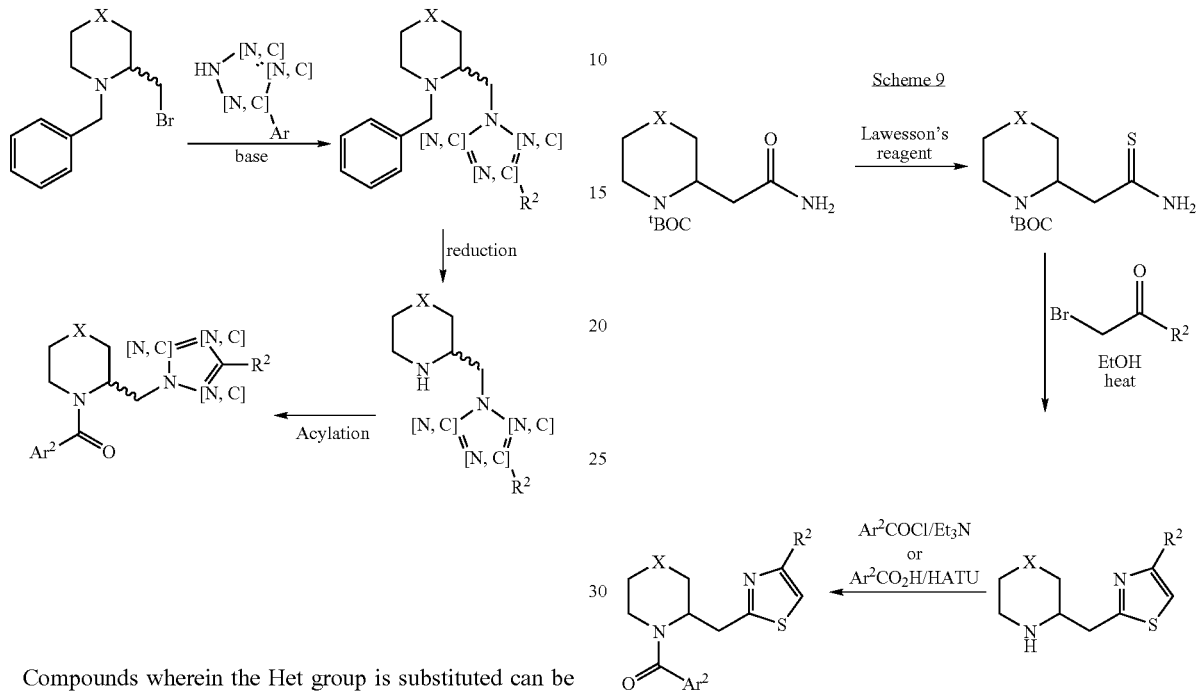

Compounds wherein the Het group is substituted can be prepared by the process defined in scheme 8 wherein Ar², X and R² are as defined for compounds of formula (I).

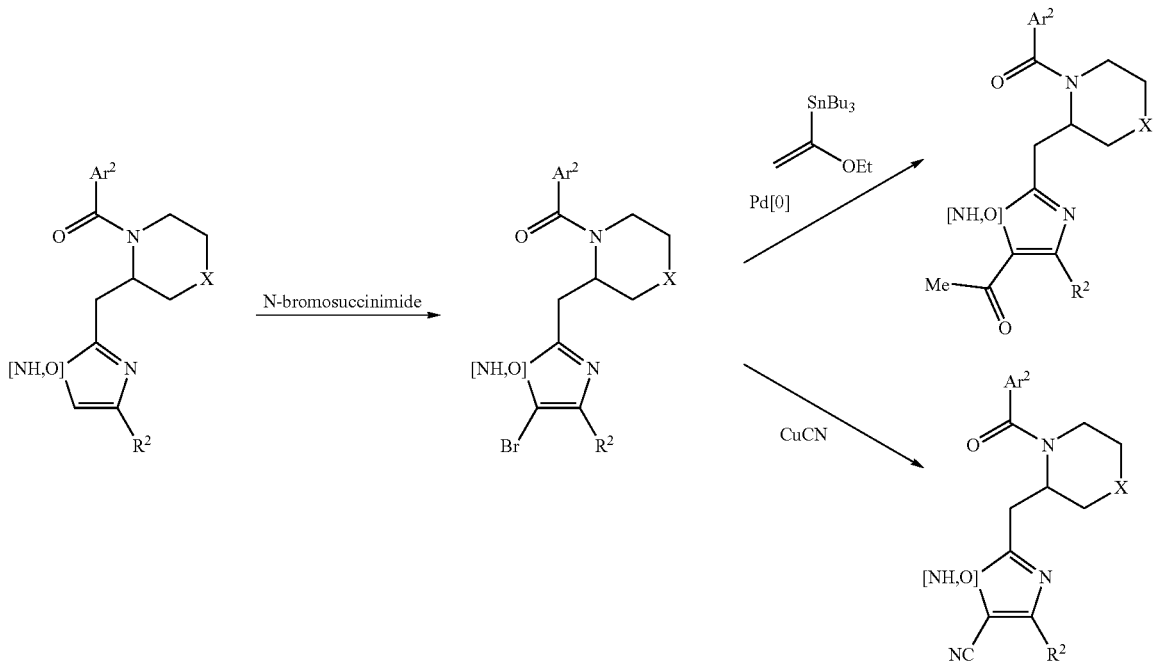

Compounds of formula (I) where Het is a 3-(5-aryltriazole) can be prepared by the process described in Scheme 10 where X, Ar² and R² are as defined for compounds of formula (I).

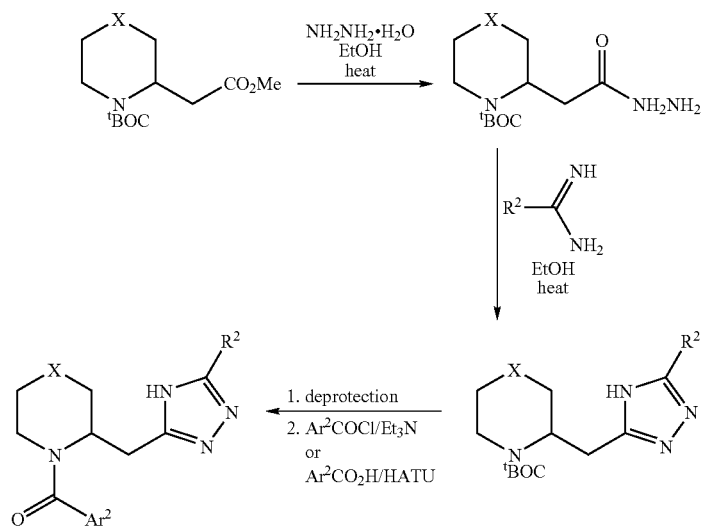

Scheme 10

All starting materials used in the above schemes are commercially available or prepared by known literature methods.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism. The compounds of formula (I) or pharmaceutically acceptable derivatives thereof are also useful in the treatment of stroke, particularly ischemic and haemorrhagic. Furthermore the compounds of formula (I) or pharmaceutically acceptable derivatives thereof are useful in blocking the emetic response i.e. nausea and vomiting.

The compounds of formula (I) and their pharmaceutically acceptable derivatives are particularly useful for the treatment of obesity, including obesity associated with Type 2 diabetes, and sleep disorders, Additionally the compounds are useful in the the treatment of stroke and blocking the emetic response, i.e. nausea and vomiting.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; a typical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence:

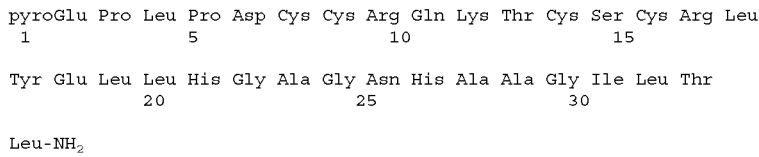

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, Drosophila or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1-D57 illustrate the preparation of intermediates to compounds of the invention.

In the Examples $^1$H NMR's were measured at 250 MHz in CDCl$_3$ unless otherwise stated.

The following abbreviations are used herein;
PyBop means benzotriazol-1-yloxytris(pyrrolidino)phosphonium hexafluorophosphate
THF means tetrahyrdofuran
EDC.HCL means 1-(3-dimethylaminopropryl)3-ethylcarbodiimide hydrochloride.
DMF means N,N-dimethylformamide
HATU means O-(7-azabenzotriazol-1-yl)-N,N,N',N'-tetramethyluronium hexafluorophospliate The following Examples illustrate the preparation of pharmacologically active compounds of the invention. The Descriptions D1-D123 illustrate the preparation of intermediates to compounds of the invention.

Description 1 (RS)-2-(5-Phenyl-[1,3,4]oxadiazol-2-ylmethyl)-piperidine-1-carboxylic acid tert butyl ester A mixture of 2carboxymethyl-piperidine-1-carboxylic acid tert butyl ester (1.22 g), (Peschke, Bernd; Ankersen, Michael; Hansen, Birgit Sehested; Hansen, Thomas Kruse; Johansen, Nils Langeland; Lau, Jesper; Madsen, Kjeld; Petersen, Hans; Thogersen, Henning; Watson, Brett. *Eur. J. Med. Chem.* (1999), 34(5), 363-380), dicyclohexylcarbodiimide (1.05 g) and 5-phenyltetrazole (0.73 g) in toluene (25 ml) was heated at 100° C. for 3 h. The reaction mixture was cooled to room temperature, diluted with diethyl ether and solvent decanted from the precipitated gum. The gum was column chromatographed (silica gel, 0-50% ethyl acetate in pentane eluant) to give the title compound (1.1 g).

Mass Spectrum (API$^+$): Found 344 (MH$^+$). C$_{19}$H$_{25}$N$_3$O$_3$ requires 343.

$^1$H NMR δ: (CDCl$_3$) 1.31 (9H, s), 1.43-1.69(6H,m), 2.95 (1H, t), 3.09 (1H, dd), 3.30(1H, dd), 4.11 (1H, br. s), 4.79 (1H, br. s.), 7.51 (3H, m) and 8.05 (2H, m).

Description 2 (RS)-2-(5-Phenyl-[1,3,4]oxadiazol-2-ylmethyl)-piperidine

A solution of (RS)-2-(5-phenyl-[1,3,4]oxadiazol-2-ylmethyl)-piperidine-1-carboxylic acid tert butyl ester (0.175 g) in dichloromethane (4 ml) was cooled (ice bath) and treated with trifluoroacetic acid (1 ml). The mixture was stirred for 1 h, added to saturated potassium carbonate and the product extracted into dichloromethane. The organic phase was dried (MgSO$_4$) and solvent removed at reduced pressure to give the title compound (0.115 g)

Mass Spectrum (API$^+$): Found 244 (MH$^+$). C$_{14}$H$_{16}$F$_3$N$_3$O requires 243.

$^1$H NMR δ: (CDCl$_3$) 1.18-1.85 (6H, m), 2.68 (1H, m), 2.97 (2H, m), 3.10(2H, m), 7.55 (3H, m) and 8.05 (2H, m).

Description 3 (RS)-2-[5-(3-Fluoro-phenyl)-[1,3,4]oxadiazol-2-ylmethyl]-piperidine-1-carboxylic acid tert butyl ester The title compound ((1.28 g) was prepared from 2-carboxymethyl-piperidine-1-carboxylic acid tert butyl ester (1.48 g), 5-(3-fluorophenyl)tetrazole (1.0 g) and dicyclohexylcarbodiimide (1.25 g) according to the method of description 1.

Mass Spectrum (API$^+$): Found 362 (MH$^+$). C$_{19}$H$_{24}$FN$_3$O$_3$ requires 361.

Description 4 (RS)-2-[5-(3-Fluoro-phenyl-[1,3,4]oxadiazol-2-ylmethyl]-piperidine The title compound (0.81 g) was prepared from the compound of description 3 (1.27 g) according to the method of description 2.

Mass Spectrum (API$^+$): Found 262 (MH$^+$). C$_{14}$H$_{16}$FN$_3$O$_3$ requires 261.

$^1$H NMR δ: (CDCl$_3$) 1.38-1.84 (6H, m), 2.71 (1H, m), 3.02 (2H, m), 3.14(2H, m), 7.22 (1H, dd), 7.48 (1H, m), 7.73 (1H, dd) and 7.83 (1H, dd).

Description 5 (RS)-2-[5-(3-Chloro-phenyl)-[1,3,4]oxadiazol-2-ylmethyl]-piperidine-1-carboxylic acid tert butyl ester The title compound (1.21 g) was prepared from 2-carboxymethyl-piperidine-1-carboxylic acid tert butyl ester (1.35 g), 5-(3-chlorophenyl)tetrazole (1.0 g) and dicyclohexylcarbodiimide (1.15 g) according to the method of description 1.

Mass Spectrum (API$^+$): Found 378 (MH$^+$). C$_{19}$H$_{24}$ClN$_3$O$_3$ requires 377.

Description 6 (RS)-2-[5-(3-Chloro-phenyl-[1,3,4]oxadiazol-2-ylmethyl]-piperidine The title compound (0.89 g) was prepared from the compound of description 5 (1.21 g) according to the method of description 2.

Mass Spectrum (API$^+$): Found 278 (MH$^+$). C$_{14}$H$_{16}$ClN$_3$O requires 277.

$^1$H NMR δ: (CDCl$_3$) 1.43-1.90 (6H, m), 2.79 (1H, m), 3.05-3.18 (2H, m), 3.27 (2H, m), 7.40-7.52 (2H, m), 7.91 (1H, dd) and 8.00 (1H, d).

Description 7 (RS)$_2$-(5-Pyridin-2-yl-[1,3,4]oxadiazol-2-ylmethyl)-piperidine-1-carboxylic acid tert butyl ester The title compound (1.39 g) was prepared from 2-carboxymethyl-piperidine-1-carboxylic acid tert butyl ester (1.65 g), 5-(pyridin-2-yl)tetrazole (1.0 g) and dicyclohexylcarbodiimide (1.43 g) according to the method of description 1.

Mass Spectrum (API$^+$): Found 345 (MH$^+$). C$_{18}$H$_{24}$N$_4$O$_3$ requires 344.

Description 8 (RS)-2-(5-Piperidin-2-ylmethyl-[1,3,4]oxadiazol-2-yl)-pynidine The title compound (0.89 g) was prepared from the compound of description 7 (1.39 g) according to the method of description 2.

Mass Spectrum (API$^+$): Found 245 (MH$^+$). $C_{13}H_{16}N_4O$ requires 244.

$^1$H NMR δ: (CDCl$_3$) 1.49-1.90 (6H, m), 2.72-2.82 (2H, m), 3.07-3.29 (4H, m), 7.44-7.49 (1H, m), 7.85-7.92 (1H, m), 8.22 (1H, dd) and 8.76 (1H, dd).

Description 9 (RS)-2-[5-(4-Fluoro-phenyl)-[1,3,4] oxadiazol-2-ylmethyl]-piperidine-1-carboxylic acid tert butyl ester The title compound (1.34 g) was prepared from 2-carboxymethyl-piperidine-1-carboxylic acid tert butyl ester (1.22 g), 5-(4-fluorophenyl)tetrazole (0.82 g) and dicyclohexylcarbodiimide (1.05 g) according to the method of description 1.

Mass Spectrum (API$^+$): Found 362 (MH$^+$). $C_{19}H_{24}FN_3O_3$ requires 361.

Description 10 (RS)-2-[5-(4-Fluoro-phenyl-[1,3,4]oxadiazol-2-ylmethyl]-piperidine The title compound (7.32 g) was prepared from the compound of description 9 (1.2 g) according to the method of description 2.

Mass spectrum (API$^+$): Found 262 (MH$^+$). $C_{14}H_{16}FN_3O$ requires 261.

$^1$H NMR δ: (CDCl$_3$) 1.25-1.84 (6H, m), 2.68 (1H, m), 21.86 (2H, m), 3.07 (2H, m), 7.12-7.27 (3H, m) and 8.04 (2H, m).

Description 11 (RS)-2-[5-(4-Chloro-phenyl)-[1,3,4]oxadiazol-2-ylmethyl]-piperidine-1-carboxylic acid tert butyl ester The title compound (1.65 g) was prepared from 2-carboxymethyl-piperidine-1-carboxylic acid tert butyl ester (1.26 g), 5-(4-chlorophenyl)tetrazole (1.08 g) and dicyclohexylcarbodiimide (1.15 g) according to the method of description 1.

Mass Spectrum (API$^+$); Found 378, 380 (MH$^+$). $C_{19}H_{24}ClN_3O_3$ requires 377, 379.

Description 12 (RS)-2-[5-(4-Chloro-phenyl-[1,3,4]oxadiazol-2-ylmethyl]-piperidine The title compound (0.89 g) was prepared from the compound of description (11 (1.21 g) according to the method of description 2.

Mass spectrum (API$^+$): found 278, 280 (MH$^+$). $C_{14}H_{16}ClN_3O$ requires 277, 279.

$^1$H NMR δ: (CDCl$_3$) 1.43-1.90 (6H, m), 2.79 (1H, m), 3.05–3.18 (2H, m ), 3.27 (2H, m), 7.40-7.52 (2H, m), 7.91 (1H, dd) and 8.00 9 1H, d).

Description 13 (RS)-2-[5-(2-Chloro-phenyl)-[1,3,4]oxadiazol-2-ylmethyl]-piperidine-1-carboxylic acid tert butyl ester The title compound (1.65 g) was prepared from 2-carboxymethyl-piperidine-1-carboxylic acid tert butyl ester (1.35 g), 5-(2-chlorophenyl)tetrazole (1.0 g) and dicyclohexylcarbodiimide (1.16 g) according to the method of description 1.

Mass Spectrum (API$^+$): Found 378, 380 (MH$^+$). $C_{19}H_{24}ClN_3O_3$ requires 377, 379.

Description 14 (RS)-2-[5-(2-Chloro-phenyl)-[1,3,4]oxadiazol-02-ylmethyl]-piperidine The title compound (1.10 g) was prepared from the compound of description 13 (1.48 g) according to the method of description 2.

Mass Spectrum (API$^+$): Found 278, 280 (MH$^+$). $C_{14}H_{16}ClN_3O$ requires 277, 279.

$^1$H NMR δ: (CDCl$_3$) 1.11-1.85 (6H, m), 2.69 (1H, m), 3.00 (2H, m), 3.10 (2H, m), 7.38 (1H, t), 7.46 (1H, t), 7.54 (1H, dd) and 7.97 (1H, dd).

Description 15 (RS)-2-[5-0(2,3-dichloro-phenyl)-1,3,4] oxadiazol-2-ylmethyl]-piperidine-1-carboxylic acid tert butyl ester The title compound (0.70 g) was prepared from 2-carboxymethyl-piperidine-1-carboxylic acid tert butyl ester (1.13 g), 5-(2,3-dichlorophenyl)tetrazole (1.0 g) and dicyclohexylcarbodiimide (0.98 g) according to the method of description 1.

Mass Spectrum (API$^+$): Found 412, 414 (MH$^+$). $C_{19}H_{23}Cl_2N_3O_3$ requires 411, 413.

Description 16 (RS-2-[5-(2,3-Dichloro-phenyl-[1,3,4]oxadiazol-2-ylmethyl]-piperidine The title compound (0.47 g) was prepared from the compound of description 15 (0.62 g) according to the method of description 2.

Mass Spectrum (API$^+$): Found 312, 314 (MH$^+$). $C_{14}H_{15}Cl_2N_3O$ requires 311, 313.

$^1$H NMR δ: (CDCl$_3$) 1.26-1.82 (6H, m), 2.69 (1H, m), 3.01 (2H, m), 3.10 (2H, m), 7.33 (1H, t), 7.66 (1H, dd) and 7.86 (1H, dd).

Description 17 (RS)-2-Hydrazinocarbonylmethyl-piperidine-1-carboxylic acid tert butyl ester 2-Methoxycarbonylmethyl-piperidine-1-carboxylic acid tert butyl ester (8.14 g) in ethanol (150 ml) was treated with hydrazine hydrate (19 ml) and the mixture boiled for 16 h. Solvent was removed at reduced pressure and the residue azeotroped with toluene to give the title compound (8.34 g)

$^1$HNMR δ: (CDCl$_3$) 1.47 (9H, s), 1.62 (6H, m), 2.34-2.42 (2H, m), 2.59-2.85 (3H, m), 3.85 (1H, br. s.), 3.97 (1H, br. s.) and 4.62 (1H, br. s).

Description 18 (RS)-2-(2-{N'-[-1-(2-Fluoro-phenyl)-methanoyl]-hydrazino}-2-oxo-ethyl) -piperidine-1-carboxylic acid tert butyl ester To a solution of the compound of description 17 (1.0 g) in pyridine (10 ml), 2-fluorobenzoyl chloride (0.62 g) was added. The mixture was stirred for 2 h, diluted with water and the milky solution extracted with ethyl acetate (×2). The combined organic phase was washed with brine, dried (MgSO$_4$) and solvent removed at reduced pressure. The residue was triturated with pentane to give after drying under reduced pressure at 35° C., the title compound (1.4 g).

Mass Spectrum (API$^+$): Found 380 (MH$^+$). $C_{19}H_{26}FN_3O_4$ requires 379.

Description 19(RS)-2-[5-(2-Fluoro-phenyl-[9,3,4] oxadiazol-2-ylmethyl]-piperidine The benzoyl hydrazide of description 18 (0.2 g) was added to polyphosphoric acid (2 g) at 45° C., the reaction temperature was increased to 150° C. and heating continued for 2 b. The reaction mixture was poured onto potassium carbonate in crushed iced and the mixture extracted with dichloromethane (×3). The combined organic extracts were washed with brine, dried (MgSO$_4$) and solvent removed it reduced pressure to give the title compound (0.08 g) as a yellow oil.

Mass Spectrum (API$^+$): Found 262 (MH$^+$). $C_{14}H_{16}FN_3O_3$ requires 261.

Description 20 (RS)-(2-{N'-(1-Benzofuran-4-yl-methanoyl)-hydrazino]-2-oxo-ethyl}-piperidine-1-carboxylic acid tert butyl ester A mixture of benzofuran-4-carboxylic acid (0.90 g), diisopropylethylamine (3.2 ml) and [O-(7-azabenzotriazol-1-yl)-1,1,3,3-tetramethyluronium hexafluorophosphate] (2.09 g) in dimethylformamide (20 ml) was stirred for 15 min and then treated with the benzoyl hydrazide of description 17 (1.43 g). The mixture was stirred for 16 h, diluted with water and extracted with diethyl ether. The ether extract was washed with water (×3), dried (MgSO$_4$) and solvent removed at reduced pressure. The residue was suspended in a mixture of diethyl ether/dichloromethane (30 ml, 2:1) to give the title compound (1.29 g) as a colourless solid.

Mass Spectrum (API$^+$): Found 402 (MH$^+$). $C_{21}H_{27}N_3O_5$ requires 401

Description 21 (RS)-2-(5-Benzofuran-4-yl-[1,3,4]oxadiazol-2-ylmethyl)-piperidine The title compound (0.1 g) was prepared from the compound of description 20 (0.2 g) according to the method of description 19. The obtained compound was used without further purification.

Mass Spectrum (API$^+$): Found 284 (MH$^+$). $C_{16}H_{17}N_3O_2$ requires 283

Description 22 (RS)-2-(2-{N'-[1-(2,3-Difluoro-phenyl)-methanoyl]-hydrazino}-2-oxo-ethyl)-piperidine-1-carboxylic acid tert butyl ester The title compound (1.15 g) was prepared from the compound of description 17 (1.0 g) and 2,3-difluorobenzoyl chloride (0.49 ml) according to the method of description 18.

Mass Spectrum (API$^+$): Found 398 (MH$^+$). $C_{19}H_{25}F_2N_3O_4$ requires 397

Description 23 (RS)-2-[5-(2,3-Difluoro-phenyl-[1,3,4]oxadiazol-2-ylmethyl]-piperidine The title compound (0.70 g) was prepared from the compound of description 22 (1.1 g) according to the method of description 19. The compound was used without further purification.

Mass Spectrum (API$^+$): Found 280 (MH$^+$). $C_{14}H_{15}F_2N_3O$ requires 279.

Description 24 (RS)-2-(2-{N'-[1-(2,5-Difluoro-phenyl)-methanoyl]-hydrazino}-2-oxo-ethyl)-piperidine-1-carboxylic acid tert butyl ester The title compound (1.50 g) was prepared from the compound of description 17 (1.0 g) and 2,5-difluorobenzoyl chloride (0.49 ml) according to the method of description 18.

Mass Spectrum (API$^+$): Found 398 (MH$^+$). $C_{19}H_{25}F_2N_3O_4$ requires 39

Description 25 (RS)-2-[5-(2,5-Difluoro-phenyl-[1,3,4]oxadiazol-2-ylmethyl]-piperidine The title compound (0.83 g) was prepared from the compound of description 24 (1.5 g) according to the method of description 19.

Mass Spectrum (API$^+$); Found 280 (MH$^+$). $C_{14}H_{15}F_2N_3O$ requires 279.

$^1$H NMR δ: (CDCl$_3$) 1.28-1.82 (6H, m), 2.63-2.74 (1H, m), 2.97-3.11 (4H, m), 7.20-7.31 (3H, m).

Description 26 (RS)-2-(2-{N'-[1-(3,5-Difluoro-phenyl)-methanoyl]-hydrazino}-2-oxo-ethyl)-piperidine-1-carboxylic acid tert butyl ester The title compound (0.79 g) was prepared from the compound of description 17 (1.0 g) and 3,5-difluorobenzoic acid (0.62) according to the method of description 20.

Mass Spectrum (API$^+$): Found 398 (MH$^+$). $C_{19}H_{25}F_2N_3O_4$ requires 397

$^1$H NMR δ: (CDCl$_3$) 1.45 (9H, s), 1.66 (6H, s), 2.52-2.87 (311, m), 3.98 (1H, d), 4.72 (1H, m), 6.96 (1H, m) and 7.34 (2H, m).

Description 27 (RS)-2-[5-(3,5-Difluoro-phenyl-[1,3,4]oxadiazol-2-ylmethyl]-piperidine The title compound (0.44 g) was prepared from the compound of description 26 (0.79 g) according to the method of description 19. The compound was used without further purification.

Mass Spectrum (API$^+$): Found 280 (MH$^+$). $C_{14}H_{15}F_2N_3O$ requires 279.

Description 28 (RS)-2-(2-{N'-[1-(6Methyl-pyridin-2-yl)-methanoyl]-hydrazino}-2-oxo-ethyl)-piperidine-1-carboxylic acid tert butyl ester The title compound (1.18 g) was prepared from the compound of description 17 (1.50 g) and 6-methylpicolinic acid (0.79 g) according to the method of description 20.

Mass Spectrum (API$^+$): Found 377 (MH$^+$). $C_{19}H_{28}N_4O_4$ requires 376

Description 29 (RS)-2-Methyl-6-(5-piperidin-2-ylmethyl-[1,3,4]oxadiazol-2-yl)-pyridine The title compound (0.60 g) was prepared from the compound of description 28 (1.17 g) according to the method of description 19. The compound was used without further purification.

Mass Spectrum (API$^+$): Found 259 (MH$^+$). $C_{14}H_{18}N_4O$ requires 258.

Description 30 (RS)-2-{2-[N'-(1-Furan-2-yl-methanoyl)-hydrazino]-2-oxo-ethyl}-piperidine-1-carboxylic acid tert butyl ester 2-Carboxymethyl-piperidine-1-carboxylic acid tert butyl ester (2.0 g) was added to [O-(7-azabenzotriazol-1-yl)-1,1,3,3-tetramethyluronium hexafluorophosphate] (3.13 g) in dimethylformamide (10 ml) containing diisopropylethylamine (3.2 g) and the mixture stirred for 15 min. 2-Furoic acid hydrazide (1.04 g) was then added and stirring continued for 16 h. The reaction mixture was diluted with water and extracted with diethyl ether. The combined ether extracts were washed with water, dried and solvent removed at reduced pressure the residue was column chromatographed (silica gel, 20-50% ethyl acetate/hexane) to give the title compound (2.05 g).

Mass Spectrum (API$^+$): Found 352 (MH$^+$). $C_{17}H_{25}N_3O_5$ requires 351.

Description 31 (RS)-2-(5-Furan-2-yl-[1,3,4]oxadiazol-2-ylmethyl)-piperidine

The title compound (0.40 g) was prepared from the compound of description 30 (1.0 g) according to the method of description 19. The compound was used without further purification.

Mass Spectrum (API$^+$): Found 234 (MH$^+$). $C_{12}H_{15}N_3O_2$ requires 233.

$^1$HNMR δ: (CDCl$_3$) 1.09-1.71 (6H, m), 2.42-2.56 (3H, m), 2.89 (2H, m), 6.79 (1H, m), 7.30 (1H, m) and 8.03 (1H, m)

Description 32 (S)-2-(5-Phehyl-[1,3,4]oxadiazol-2-ylmethyl)-pyrrolidine-1-carboxylic acid tert butyl ester The title compound was prepared from (S)-2-carboxymethyl-pyrrolidine-1-carboxylic acid tert butyl ester (2.50) and 5-phenyltetrazole (1.59 g) according to the method of description 1.

Mass Spectrum (API$^+$): Found 330 (MH$^+$). $C_{18}H_{23}N_3O_3$ requires 329.

$^1$H NMR δ: (CDCl$_3$) 1.49 (9H, s), 1.81-1.88 (2H, m), 2.17-2.25 (2H, m), 2.40 and 3.09 (1H, m), 3.35-3.73 (3H, m), 4.28, 5.12 (1H, m), 7.50 (3H, m) and 8.03 (2H, m).

Description 33 2-Phenyl-5-(S)-1-pyrrolidin-2-ylmethyl-[1,3,4]oxadiazole

The title compound (1.85 g) was prepared from the compound of description 32 (2.45 g) according to the method of description 2.

Mass Spectrum (API$^+$): Found 230 (MH$^+$). $C_{13}H_{15}N_3O$ requires 229.

$^1$HNMR δ: (CDCl$_3$) 1.58-1.69 (2H, m), 1.76-1.97 (2H, m), 2.04-2.36 (1H, m), 2.99-3.23 (4H, m), 3.69-3.80 (1H, m), 7.45-7.57 (3H, m) and 8.01-8.05 (2H, m).

Description 34 (1-{1-[5-(4-Fluoro-phenyl)-2-methyl-thiazol-4yl]-methanoyl}-piperidin-2-yl)-acetic acid methyl ester The title compound (2.1 g) was prepared from piperidin-2-yl-acetic acid methyl ester (3.4 g) and 2methyl-5-(4-fluorophenyl)-thiazole-4-carboxylic acid (2.20 g) according to the method of description 20.

Mass Spectrum (API$^+$): Found 377 (MH$^+$). $C_{19}H_{21}FN_2O_3S$ requires 376.

Description 35 (RS)-(1-{1-[5-(4-Fluoro-phenyl)-2-methyl-thiazol-4-yl]-methanoyl}-piperidin-2-yl)-acetic acid The compound of description 34 (3.4 g) in methanol (75 ml) was treated with water (25 ml) containing sodium hydroxide (0.74 g). The mixture was stirred for 16 h, solvent removed at reduced pressure, the residue dissolved in water and washed with diethyl ether. The aqueous phase was acidified with 5N hydrochloric acid and extracted with ethyl acetate. The organic phase was dried (MgSO$_4$) and solvent removed at reduced pressure. The residue was triturated with pentane and dried in vacuo to give the title compound (20.95 g)

Mass Spectrum (API$^+$): Found 363 (MH$^+$). $C_{18}H_{19}FN_2O_3S$ requires 362

Description 36 (RS)-(1-{1-[5-(4-Fluoro-phenyl)-2-methyl-thiazol-4-yl]-methanoyl}-piperidin-2-yl)-acetic acid 2-(4-fluoro-phenyl)-2-oxo-ethyl ester The acid of description 35 (0.4 g) was dissolved in dimethylformamide (10 ml) containing potassium carbonate (0.179 g) and 2-bromo-4'-fluoroacetophenone (0.24 g) and the mixture stirred for 16 h. Water (20 ml) was added and the mixture extracted with ethyl acetate. The organic phase was washed with water, dried (MgSO$_4$) and solvent removed at reduced pressure to give the title compound (0.51 g).

Mass Spectrum (API$^+$): Found 499 (MH$^+$). $C_{26}H_{24}F_2N_2O_4S$ requires 498

$^1$HNMR δ: (CDCl$_3$) (doubling of signals due to restricted rotation) 1.41-1.88 (6H, m), 2.49-2.92, 3.37 (411, m), 2.68, 2.69 (3H, s), 4.15, 4.67 (1H, m), 5.13-5.31 (2H, m), 7.05 (2H, m). 7.17 (2H, m), 7.44-7.54 (2H, m) and 7.88-7.98 (2H, m).

Description 37 (RS)-(1-{1-[5-(4-Fluoro-pheuyl)-2-methyl-thiazol-4-yl]-methanoyl}-piperidin-2-yl)-acetic acid 2-(2-methoxyphenyl)-2-oxo-ethyl ester The title compound (0.51 g) was prepared from the acid of description 35 (0.40 g) and 2-bromo-4'-methoxyacetophenone (0.25 g) according to the method of description 36.

Mass Spectrum (API$^+$): Found 511 (MH$^+$). $C_{27}H_{27}FN_2O_5S$ requires 510.

Description 38 (RS)-(1-{1-[5-(4-Fluoro-phenyl)-2-methyl-thiazol-4-yl]-methanoyl}-piperidin-2-yl)-acetic acid 2-(3-fluoro-phenyl)-2-oxo-ethyl ester The title compound (0.32 g) was prepared from the acid of description 35 (0.40 g) and 2-bromo-3'-fluoroacetophenone (0.24 g) according to the method of description 36.

Mass Spectrum (API$^+$): Found 499 (MH$^+$). $C_{26}H_{24}F_2N_2O_4S$ requires 498

Description 39 (RS)-(1-{1-[5-(4-Fluoro-phenyl)-2-methyl-thiazol-4-yl]-methanoyl}-piperidin-2-yl)-acetic acid 2-(2-fluoro-phenyl)-2-oxo-ethyl ester The title compound (0.32 g) was prepared from the acid of description 35 (0.40 g) and 2-bromo-2'-fluoroacetophenone (0.24 g) according to the method of description 36.

Mass Spectrum (API$^+$): Found 499 (MH$^+$). $C_{26}H_{24}F_2N_2O_4S$ requires 498

Description 40 (1-{1-[5-(4-Fluoro-phenyl)-2-methyl-thiazol-4-yl]-methanoyl}-piperidin-2-yl)-acetic acid 1-methyl-2-oxo-2-phenyl-ethyl ester The title compound (0.452 g) was prepared from the acid of description 35 (0.40 g) and 2-bromopropiophenone (0.234 g) according to the method of description 36.

Mass Spectrum (API$^+$): Found 495 (MH$^+$). $C_{27}H_{27}FN_2O_4S$ requires 494

Description 41: (RS)-1tert-butyloxycarbonyl)-2-(N-methoxy-N-methylcarbamoyl)piperidine To (RS)-1-(tert-butyloxycarbonyl)-2-piperidine carboxylic acid (5.32 g, 23.2 mmol) in dichloromethane (20 ml) was added sequentially N,O-dimethyl hydroxylamine hydrochloride (2.68 g, 27.5 mmol), triethylamine (12 ml, 86.0 mmol) and py-BOP (13.2 g, 25.4 mmol). The resultant mixture was stirred at ambient temperature for 6 h, then diluted with dichloromethane (350 ml) and poured into 1M HCl (50 ml).

The organic phase was separated and washed with saturated aqueous sodium hydrogen carbonate (3×50 ml) and brine (50 ml) and then evaporated in vacuo, The residue was chromatographed on silica gel eluting with 20% ethyl acetate in hexane to give the title compound as a colourless oil (3.09 g, 49%).

Mass spectrum (API$^+$): 273 (MH$^+$). $C_{13}H_{24}N_2O_4$ requires 272.

Description 42: (RS)-1-(tert-butyloxycarbonyl)-2-((5-(4fluorophenyl)-furan-2-yl)carbonyl)piperidine To a stirred solution of 2-(4-fluorophenyl)-furan (1.8 g, 11.1 mmol) in THF (100 ml) at −35° C. was added n-butyl lithium (2.5M in THF) (4.54 ml, 11.4 mmol) over 3 min. The resultant mixture was stirred for 10 min. at −35° C. and then (RS)-1-(tert-butyloxycarbonyl)-2-(N-methoxy-N-methyl-carbamoyl)piperidine (3.09 g, 11.4 mmol) in THF (10 ml) was added over 1 min. The resultant solution was stirred for 15 min. at −35° C. and then poured into saturated ammonium chloride (120 ml) and extracted with ethyl acetate (3×50 ml). The combined organics were washed with saturated aqueous sodium hydrogen carbonate (50 ml) and evaporated in vacuo. The residue was chromatographed on silica gel eluting with 10% ethyl acetate in hexane to give the title compound as a golden oil (3.59 g, 85%).

Mass spectrum (API$^+$): 374 (MH$^+$). $C_{21}H_{24}NO_4F$ requires 373.

Description 43: (RS)-2-(5-(4-Fluorophenyl)-furan-2-ylmethyl)-piperidine

To a solution of (RS)-1-(tert-butyloxycarbonyl)-2-((5-(4-fluorophenyl)-furan-2-yl)carbonyl)piperidine (2.0 g, 5.36 mmol) in diethylene glycol (20 g), was added hydrazine hydrate (0.31 ml, 5.36 mmol) and the resultant mixture heated at 100° C. for 30 min. After cooling to room temperature, potassium hydroxide (1.0 g, 17.8 mmol) was added and the mixture heated at 200° C. for 18 h. The reaction mixture was then poured into water (100 ml) and extracted with diethyl ether (3×75 ml). The combined organic extracts were dried (Na$_2$SO$_4$) and evaporated in vacuo to give the title compound as a brown oil (0.88 g, 63%).

Mass spectrum (API$^+$): 260 (MH$^+$). $C_{16}H_{18}FNO$ requires 259.

Description 44: (RS)-2-(2-Oxo-2-phenyl-ethoxycarbonylmethyl)-piperidine-1-carboxylic acid tert butyl ester 2-Carboxymethyl-piperidine-1-carboxylic acid tert butyl ester (2.86 g) and sodium carbonate (0.62 g) were dissolved in water (30 ml) using gentle warming. A solution of 2-bromoacetophenone (2.33 g) in ethanol (60 ml) was then added and the mixture boiled for 2 h. the mixture was cooled to room temperature and stood for 16 h. The mixture was again boiled for 2 h. solvent removed at reduced pressure and the residue partitioned between water and ethyl acetate. The organic phase was dried (MgSO$_4$) and solvent removed at reduced pressure. The residue was column chromatographed (silica gel, 1:1 ethyl acetate:pentane) to give the title compound (3.14 g).

Mass spectrum (API$^+$): 362 (MH$^+$). $C_{19}H_{27}NO_5$ requires 361.

Description 45 (RS)-Piperidin-2-yl-acetic acid 2-oxo-2-phenyl-ethyl ester

The title compound (0.68 g) was prepared from the compound of description 44 (0.80 g) according to the method of description 2.

Mass spectrum (API$^+$): 262 (MH$^+$). $C_{14}H_{18}NO_5$ requires 261.

Descriptions 46-49

The compounds of descriptions 46-49 were prepared from the compound of description 45 (1 mole) and the corresponding carboxylic acid (1 mole) according to the method of description 1

| Description | Ar$^2$ | yield % | Mass Spectrum (Electrospray LC/MS) |
|---|---|---|---|
| 46 | 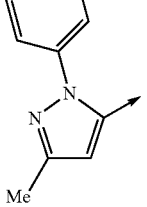 | 44 | Found 464(MH$^+$). $C_{26}H_{26}FN_3O_4$. requires 463 |
| 47 | 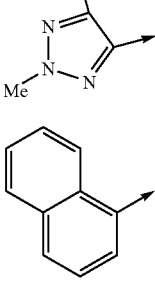 | 54 | Found 465(MH$^+$). $C_{25}H_{25}FN_4O_4$. requires 464 |
| 48 | 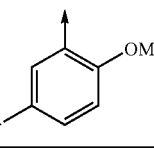 | 40 | Found 416(MH$^+$). $C_{26}H_{25}NO_4$. requires 415 |
| 49 |  | 53 | Found 474, 476(MH$^+$). $C_{23}H_{24}BrNO_5$. requires 473, 475 |

Description 50 (RS)-(1-{1-[5-(4-Fluoro-phenyl)-2-methyl-thiazol-4-yl]-methanoyl}-piperidin-2-yl)-acetic acid 2-phenyl-2-oxo-ethyl ester The title compound (0.89 g) was prepared from the acid of description 35 (0.72 g) and 2-bromoacetophenone (0.39 g) by boiling in water/ethanol (15 ml, 1:2) containing sodium carbonate (0.10 g) for 4 h, cooling removing solvent at reduced pressure and partitioning the residue between dichloromethane and water. The organic phase was separated, dried (MgSO$_4$) and solvent removed at reduced pressure.

Mass Spectrum (API$^+$): Found 481 (MH$^+$). $C_{26}H_{25}FN_2O_4S$ requires 480

Description 51 (RS-(4-{1-[5-(4-Fluoro-phenyl)-2-methyl-thiazol-4-yl]-methanoyl}-morpholin-3-yl)-acetic acid ethyl ester Morpholin-3-ylacetic acid ethyl ester *Chem Pharm Bull* 94, 31(1), 1983 (2.10 g) was dissolved in dichloromethane (50 ml) and treated with triethylamine (1.33 g). The mixture was cooled (ice bath) and 5-(4-fluoro-phenyl)-2-methyl-thiazole-4-carbonyl chloride (1.53 g) in dichloromethane (10 ml) added. The mixture was stirred for 16 h, diluted with water and the organic phase separated. The aqueous phase was extracted with dichloromethane (2×100 ml), the organic phases combined, dried (Na$_2$SO$_4$) and solvent removed at reduced pressure the residue was column chromatographed (silica gel, 40% ethyl acetate:pentane→60% ethyl acetate pentane eluant) to give the title compound (1.46 g).

Mass Spectrum (API$^+$): Found 393 (MH$^+$). $C_{19}H_{21}FN_2O_4S$ requires 392.

Description 52 (RS)-(4-{1-[5-(4-Fluoro-phenyl)-2-methyl-thiazol-4-yl]-methanoyl}-morpholin-3-yl)-acetic acid The title compound (1.33 g) was prepared from the compound of description 51 (1.46), according to the method of description 35.

Mass Spectrum (API$^-$): Found 363 [(M-H)$^-$]. $C_{17}H_{17}FN_2O_4S$ requires 364.

Description 53 (RS)-(4-{1-[5-(4-Fluoro-phenyl)-2-methyl-thiazol-4-yl]-methanoyl}-morpholin-3-yl)-acetic acid 2-oxo-2-phenyl-ethyl ester The title compound (0.57 g) was prepared from the compound of description 52 (0.6 g) and 2-bromoacetophenone (0.33 g) according to the method of description 50.

Mass Spectrum (API$^+$): Found 483 (MH$^+$). $C_{25}H_{23}FN_2O_5S$ requires 482.

Description 54 (RS)-2-{[2-(4-Fluoro-phenyl)-2-oxo-ethylcarbamoyl]-methyl}-piperidine-1-carboxylic acid tert butyl ester The title compound (0.77 g) was prepared from 2-carboxymethyl-piperidine-1-carboxylic acid tert butyl ester (0.80 g) and 2-amino-1-(4-fluoro-phenyl)-ethanone (0.63 g) according to the method of description 20.

Mass Spectrmm (API$^+$): Found 379 (MH$^+$). $C_{21}H_{27}FN_2O_4$ requires 378.

Description 55 (RS)-2-[5-(4Fluoro-phenyl)-oxazol-2-ylmethyl]-piperidine

The amide of description 54 (0.77 g) and polyphosphoric acid (10 h) were combined and heated together at 150° C. for 4 h. After cooling to room temperature the reaction mixture was poured onto ice/water and basified to pH 10 with potassium carbonate. The aqueous phase was extracted with dichloromethane, the combined extracts dried (MgSO$_4$) and solvent removed at reduced pressure to give the title compound (0.49 g)

Mass Spectrum (API$^+$): Found 261 (MH$^+$). $C_{15}H_{17}FN_2O$ requires 260.

Description 56 (RS)-2-{[2-phenyl-2-oxo-ethylcarbamoyl]-methyl}-piperidine-1-carboxylic acid tert butyl ester The title compound (0.63 g) was prepared from 2-carboxymethyl-piperidine-1-carboxylic acid tert butyl ester (0.50 g) and 2-amino-1-phenylethanone (0.35 g) according to the method of description 54.

Mass Spectrum (API$^+$): Found 273 (MH$^+$-C$_5$H$_9$O$_2$). $C_{21}H_{28}N_2O_4$ requires 372.

Description 57 (RS)-2-(5-phenyloxazol-2-ylmethyl)-piperidine

The title compound (0.28 g) was prepared from the amide of description 56 (0.40 g) according to the method of description 55.

Mass Spectrum (API$^+$): Found 243 (MH$^+$). $C_{15}H_{18}N_2O$ requires 242.

Description 58 (S)-2-[2-(4-Fluoro-phenyl)-2-oxo-ethoxycarbonylmethyl]-pyrrolidine-1-carboxylic tert butyl ester The title compound (3.2 g) was prepared from (S)-2-carboxymethyl-pyrrolidine-1-carboxylic acid tert butyl ester (2.02 g) and 2-bromo-4'-fluoroacetophenone (1.91 g) according to the method of description 36.

Mass Spectrum (API$^+$): Found 266 (MH$^+$-C$_5$H$_9$O$_2$). $C_{19}H_{24}FNO_5$ requires 365.

Description 59 (S)-2-[5-(4-Fluoro-phenyl)-1H-imidazol-2-ylmethyl]-pyrrolidine-1-carboxylic tert butyl ester The compound of description 58 (2.2 g) was combined with ammonium acetate (8 g) and warmed to 140° C. for 1.5 h. The reaction mixture was cooled, poured onto saturated potassium carbonate and extracted with dichloromethane (×2). The combined dichloromethane extracts were dried (MgSO$_4$) and solvent removed at reduced pressure. The residue was column chromatographed (silica gel, 20% ethyl acetate/pentane→ethyl acetate), the appropriate fractions were combined and solvent removed at reduced pressure to give the title compound (0.81 g).

Mass Spectrum (API$^+$): Found 346 (MH$^+$). $C_{19}H_{24}FN_3O_2$ requires 345.

Description 60 5-(4-Fluoro-phenyl)-2-(S)-1-pyrrolidin-2-ylmethyl-1H-imidazole hydrochloride The compound of description 59 (0.80 g) was dissolved in methanol (20 ml) Ind treated with 4M HCl in dioxane (6 ml). The mixture was stirred for 6 h and then solvent removed at reduced pressure to give the title compound (0.57 g) as a foam.

Mass Spectrum (API$^+$): Found 346 (MHt). $C_{14}H_{15}FN_3$ requires 345.

Description 61 (RS)-2-[2-(4-Fluoro-phenyl)-2-oxo-ethoxycarbonylmethyl]-piperidine-1-carboxylic tert butyl ester The title compound (3.83 g) was prepared from (RS)-2-carboxymethyl-piperidine-1-carboxylic acid tert butyl ester (2.54 g) and 2-bromo-4'-fluoroacetophenone (2.26 g) according to the method of description 36.

Mass Spectrum (API$^+$): Found 308 (MH$^+$-$C_5H_9O_2$). $C_{20}H_{26}FNO_5$ requires 307.

Description 62 (RS-2-[5-(4-Fluoro-phenyl)-1H-imidazol-2-ylmethyl]-piperidine-1-carboxylic tert butyl ester The title compound (0.80 g) was prepared from the compound of description 61 (1.40 g) according to the method of example 59.

Mass Spectrum (API$^+$): Found 360 (MH$^+$). $C_{20}H_{26}FN_3O_2$ requires 359.

Description 63 5-(4Fluoro-phenyl)-2-(RS)-1-piperidine-2-ylmethyl-1H-imidazole hydrochloride The title compound (0.65 g) was prepared from the compound of description 62 (0.70 g) according to the method of description 60.

Mass Spectrum (API$^+$): Found 346 (MH$^+$). $C_{15}H_{17}FN_3$ requires 345.

Description 64 (RS)-(1-{1-[5(4-Fluoro-phenyl)-2-methyl-thiazol-4-yl]-methanoyl}-piperidin-2-yl)-acetic acid 2-(2-bromophenyl)-2-oxo-ethyl ester The title compound (0.51 g) was prepared from the acid of description 35 (0.60 g) and 2-bromo-2'-bromoacetophenone (0.51 g) according to the method of description 36.

Mass Spectrum (API$^+$): Found 559, 561 (MH$^+$). $C_{26}H_{24}BrF_2N_2O_4S$ requires 558, 560

Description 65 (RS)-2-[2-(4-Fluoro-phenyl)-2-oxo-ethoxycarbonylmethyl]-piperidine-1-carboxylic acid tert butyl ester The title compound (3.70 g) was prepared from (RS)2-carboxymethyl-piperidine-1-carboxylic acid tert butyl ester (2.50 g) according to the method of example 36

Mass Spectrum (API$^+$): Found 380 (MH$^+$). $C_{20}H_{26}FNO_5$ requires 379

Description 66 (RS)-2-[5-(4-Fluoro-phenyl)-1H-imidazol-2-ylmethyl]-piperidine-1-carboxylic acid tert butyl ester The title compound (1.71 g) was prepared from the compound of description 65 (370 g) according to the method of description 59.

Mass Spectrum (API$^+$): Found 366 (MH$^+$). $C_{20}H_{26}FN_3O_2$ requires 365

Description 67 (RS)-2-[4Bromo-5-(4-fluoro-phenyl)-1H-imidazol-2-ylmethyl]-piperidine-1-carboxylic acid tert butyl ester The compound of description 66 (0.62 g) was dissolved in DMF (2 ml) containing potassium bicarbonate (0.29 g) and the mixture cooled (ice/salt bath). Bromine (0.15 ml) was added, the mixture stirred for 15 min, poured onto crushed ice and 20% ammonia added to destroy excess bromine. The mixture was extracted with diethyl ether (×3), the combined organic phase washed with water (×3, dried (MgSO$_4$) and solvent removed at reduced pressure to give after chromatography (silica gel, 0→20% ethyl acetate/pentane eluant), the title compound as a gum (0.25 g)

Mass Spectrum (API$^+$): Found 438, 440 (MH$^+$). $C_{20}H_{25}BrFN_3O_2$ requires 437, 439

Description 68 (RS)-2-[4-Bromo-5-(4-fluoro-phenyl)-1H-imidazol-2-ylmethyl]-piperidine hydrochloride The title compound (0.27 g) was prepared from the compound of description 67 (0.25 g) according to the procedure of description 60.

Mass Spectrum (API$^+$): Found 338, 340 (MH$^+$). $C_{15}H_{17}BrFN_3$ requires 337, 339

Description 69 (RS)-(1-{1-[4-(4-Fluoro-phenyl)-1-methyl-1H-pyrazol-3-yl]-methanoyl}-piperidin-2-yl)-acetic acid 2-(4-fluoro-phenyl)-2-oxo-ethyl ester The title compound (0.74 g) was prepared from piperidin-2-yl-acetic acid methyl ester (0.36 g) and {1-[4-(4-fluoro-phenyl)-1-methyl-1H-pyrazol-3-yl]carboxylic acid (0.5 g) according to the method of descriptions 34, 35 and 36.

Description 70 (RS)(1-{1-[4-(4-Fluoro-phenyl)-1H-pyrazol-3-yl]-methanoyl}-piperidin-2-yl)-acetic acid 2-(4-fluoro-phenyl)-2-oxo-ethyl ester The title compound (0.51 g) was prepared from piperidin-2-yl-acetic acid methyl ester (0.38 g) and {1-[4-(4-Fluoro-phenyl)-1H-pyrazol-3-yl]carboxylic acid (0.5 g) according to the method of descriptions 34, 35 and 36.

Description 71 (RS)-[1-Quinolin-2-yl-methanoyl)-piperidin-2-yl]-acetic acid 2-(4-fluoro-phenyl)-2-oxo-ethyl ester The title compound (0.48 g) was prepared from piperidin-2-yl-acetic acid methyl ester (0.38 g) and quinoline-2-carboxylic acid (0.5 g) according to the method of descriptions 34, 35 and 36.

Description 72 (RS)-2-[2-phenyl-2-oxo-ethoxycarbonylmethyl]-piperidine-1-carboxylic tert butyl ester The title compound (7.07 g) was prepared from (RS)-2-carboxymethyl-piperidine-1-carboxylic acid tert butyl ester (5.0 g) and 2-bromoacetophenone (4.18 g) according to the method of description 36.

Mass Spectrum (API$^+$): Found 262 (MH$^+$-$C_5H_9O_2$). $C_{20}H_{27}NO_5$ requires 361.

Description 73 (RS)-2-[5-Phenyl-1H-imidazol-2-ylmethyl]-piperidine-1-carboxylic tert butyl ester The title compound (3.78 g) was prepared from the compound of description 72 (7.07 g) according to the method of example 59.
Mass Spectrum (API$^+$): Found 242 (MH$^+$-C$_5$H$_9$O$_2$) C$_{20}$H$_{27}$N$_3$O$_2$ requires 341.

Description 74 5-Phenyl-2-(RS)-1-piperidine-2-ylmethyl-1H-imidazole

The title compound (0.65 g) was prepared from the compound of description 73 (0.70 g) according to the method of description 60. The hydrochloride salt generated during the reaction was neutralised by dissolving the product in water, neutralising with solid potassium carbonate, extracting with dichloromethane, drying the organic phase (Na$_2$SO$_4$) and removing the solvent at reduced pressure.
Mass Spectrum (API$^+$): Found 242 (MH$^+$). C$_{15}$H$_{18}$N$_3$ requires 241.

Description 75 (RS)-2-(2-Oxo-2-phenyl-ethoxycarbonylmethyl)piperidine-1-carboxylic acid benzyl ester The title compound (4.0 g) was prepared from 2-bromoacetophenone (2.20 g) and 2-carboxymethyl-piperidine-1-carboxylic acid benzyl ester according to the method of description 36
Mass Spectrum (API$^+$): Found 396 (MH$^+$). C$_{23}$H$_{25}$NO$_5$ requires 395.

Description 76 (RS)-2-(4-Phenyl-oxazol-2-ylmethyl)-piperidine-1-carboxylic acid benzyl ester The title compound (0.95 g) was prepared from the compound of description 75 (3.0 g) according to the method of Example 54.
Mass Spectrum (API$^+$): Found 377 (MH$^+$). C$_{23}$H$_{24}$N$_2$O$_3$ requires 376.

Description 77 (RS)-2-(4-Phenyl-oxazol-2-ylmethyl)-piperidine

The compound of description 76 (0.097 g) and 10% palladium/charcoal (0.05 g) in ethanol (5 ml) containing cyclohexene (0.5 ml) was heated at 75° C. for 1.5 h, cooled, filtered (kieselguhr) and solvent removed at reduced pressure to give the title compound (0.06 g).
Mass Spectrum (API$^+$): Found 243 (MH$^+$). C$_{15}$H$_{18}$N$_2$O requires 242.

Description 78 (RS)-(1-{1-[5-(4-Fluoro-phenyl)-2-methyl-thiazol-4-yl]-methanoyl}-piperidin-2-yl)-acetic acid hydrazide The ester of description 34 (1.06 g) in ethanol (25 ml) was treated with hydrazine hydrate (5 ml) and the mixture boiled for 24 h. Solvent was removed at reduced pressure and the residue column chromatographed (silica gel; 0→10% methanol/dichloromethane). The appropriate fractions were combined and solvent removed at reduced pressure to give the title compound (0.62 g).
Mass Spectrum (API$^+$): Found 377 (MH$^+$). C$_{18}$H$_{21}$N$_4$O$_2$S requires 376.

Description 79 (RS)-2-Hydrazinocarbonylmethyl-piperidine-1-carboxylic acid tert butyl ester The title compound (2.98 g) was prepared from 2-methoxycarbonylmethyl-piperidine-1-carboxylic acid tert butyl ester (3.08 g) according to the method of description 78.
Mass Spectrum (API$^+$): Found 258 (MH$^+$). C$_{12}$H$_{23}$N$_3$O$_3$ requires 257.

Description 80 (RS)-2-[5-(4-Fluoro-phenyl)-4H-[1,2,4]triazol-3-ylmethyl]-piperidine-1-carboxylic acid tert butyl ester The title compound (0.32 g) was prepared from the compound of description 79 (1.49 g) according to the method of example 105.
Mass Spectrum (API$^+$): Found 361 (MH$^+$). C$_{19}$H$_{25}$FN$_4$O$_2$ requires 360.

Description 81 (RS)-2-[5 (4-Fluoro-phenyl)-4H-[1,2,4]triazol-3-ylmethyl]-piperidine The title compound (0.31 g) was prepared from the compound of description 80 (0.32 g) according to the method of description 2.
Mass Spectrum (API$^+$): Found 261 (MH$^+$). C$_{14}$H$_{17}$FN$_4$ requires 260.

Description 82 (RS)-2-[2-(3-Methoxy-phenyl)-2-oxo-ethoxycarbonylmethyl]-piperidine-1-carboxylic tert butyl ester The title compound (3.06 g) was prepared from (RS)-2-carboxymethyl-piperidine-1-carboxylic acid tert butyl ester (2.0 g) and 2-bromo-3'-methoxyacetophenone (1.88 g) according to the method of description 36.
Mass Spectrum (API$^+$): Found 292 (MH$^+$-C$_5$H$_8$O$_2$). C$_{21}$H$_{29}$NO$_6$ requires 391.

Description 83 (RS)-2-[5-(3-Methoxy-phenyl)-1H-imidazol-2-ylmethyl]-piperidine-1-carboxylic tert butyl ester The title compound (3.78 g) was prepared from the compound of description 82 (3.0 g) according to the method of description 59.
Mass Spectrum (API$^+$): Found 272 (MH$^+$-C$_5$H$_9$O$_2$) C$_{21}$H$_{29}$N$_3$O$_3$ requires 371.

Description 84 5-(3-Methoxy-phenyl)-2-(RS)-1-piperidine-2-ylmethyl-1H-imidazole The title compound (1.06 g) was prepared from the compound of description 83 (1.33 g) according to the method of description 2.
Mass Spectrum (API$^+$): Found 242 (MH$^+$). C$_{15}$H$_{18}$N$_3$ requires 241.

Description 85 (RS)-2-[2-(3-Chloro-phenyl)-2-oxo-ethoxycarbonylmethyl]-piperidine-1-carboxylic tert butyl ester The title compound (2.65 g) was prepared from (RS)-2-carboxymethyl-piperidine-1-carboxylic acid tert butyl ester (2.0 g) and 2-bromo-3'-chloroacetophenone (1.92 g) according to the method of description 36.
Mass Spectrum (API$^+$): Found 396, 398 (MH$^+$). C$_{20}$H$_{26}$NO$_5$Cl requires 395, 397.

Description 86 (RS)-2-[5-(3-Chloro-phenyl)-1H-imidazol-2-ylmethyl]-piperidine-1-carboxylic tert butyl ester The title compound (1.61 g) was prepared from the compound of description 85 (2.65 g) according to the method of description 59.

Mass Spectrum (API$^+$): Found 375, 377 (MH$^+$) $C_{20}H_{25}ClN_3O_2$ requires 374, 376.

Description 87 5-(3-Chloro-phenyl)-2-(RS)-1-piperidine-2-ylmethyl-1H-imidazole The title compound (0.85 g) was prepared from the compound of description 86 (1.05 g) according to the method of description 2.

Mass Spectrum (API$^+$): Found 275, 277 (MH$^+$). $C_{15}H_{17}ClN_3$ requires 274, 276.

Description 88 (RS)-2-[2-(3-Cyano-phenyl)-2-oxo-ethoxycarbonylmethyl]-piperidine-1-carboxylic tert butyl ester The title compound (1.51 g) was prepared from (RS)-2-carboxymethyl-piperidine-1-carboxylic acid tert butyl ester (1.15 g) and 2-bromo-3'-cyanoacetophenone (1.06 g) according to the method of description 36.

Mass Spectrum (API$^+$): Found 387 (MH$^+$). $C_{21}H_{26}N_2O_5$ requires 386.

Description 89 (RS)-2-[5-(3-Cyano-phenyl)-1H-imidazol-2-ylmethyl]-piperidine-1-carboxylic tert butyl ester The title compound (1.25 g) was prepared from the compound of description 88 (1.50 g) according to the method of description 59.

Mass Spectrum (API$^+$): Found 366 (MH$^+$) $C_{21}H_{25}N_4O_2$ requires 365.

Description 90 5-(3-Cyano-phenyl)-2-(RS)-1-piperidine-2-ylmethyl-1H-imidazole The title compound (0.85 g) was prepared from the compound of description 89 (1.25 g) according to the method of description 2.

Mass Spectrum (API$^+$): Found 266 (MH$^+$). $C_{16}H_{17}N_4$ requires 265.

Description 91 (RS)-1-Benzyl-2-[5-(4fluoro-phenyl)tetrazol-2-ylmethyl]-piperidine N-Benzyl-2-bromomethylpiperidine (2.1 g), 5-(4-fluoro-phenyl)-2H-tetrazole (1.28 g) and potassium carbonate (6 g) were combined in xylene (100 ml) containing diisopropyl-ethylamine (7 ml) and boiled for 16 h. The reaction mixture was cooled to room temperature, filtered, solvent removed at reduced pressure and the residue column chromatographed (silica gel; diethyl ether/petroleum ether 40:60 eluant) to give after combining appropriate fractions and removing solvent at reduced pressure the title compound 1.44 g.

Mass Spectrum (API$^+$): Found 340 (MH$^+$). $C_{19}H_{22}N_5F$ requires 339.

Description 92 (RS)-2-[5-(Fluoro-phenyl)-tetrazol-2ylmethyl]-piperidine

The compound of description 91 (1.4 g) was dissolved in ethanol (100 ml), palladium hydroxide (0.40 g) added and the mixture hydrogenated at 50 psi and 50° C. for 3 h. The mixture was filtered through kieselguhr and solvent removed at reduced pressure and the residue triturated with diethyl ether/petroleum ether to give the title compound as a solid.

Mass Spectrum (API$^+$): Found 250 (MH$^+$). $C_{12}H_{16}N_5F$ requires 249.

Description 93 (RS)-1-Benzyl-2-(4-phenyl-imidazol-1-ylmethyl)-piperidine

4-Phenylimidazole (1.3 g) was treated with sodium hydride (0.6 g 50% in oil) in dry tetrahydrofuran (80 ml). When gas evolution had ceased, 2-bromomethyl-N-benzylpiperidine (2.5 g) in tetrahydrofuran (30 ml) was added. The mixture was stirred for 16 h, solvent removed at reduced pressure and treated with ice/water (1:1, 100 ml). The mixture was extracted with dichloromethane (2×), the combined organic phase washed with water, solvent removed at reduced pressure and the residue column chromatographed (silica gel, 0.5→9.5% dichloromethane/methanol). Appropriate fractions were combined to give the title compound 0.72 g.

Mass Spectrum (API$^+$): Found 332 (MH$^+$). $C_{22}H_{25}N_3$ requires 331.

Description 94 (RS)-2-(4-Phenyl-imidazol-1-ylmethyl)-piperidine

The title compound (0.50 g) was prepared from the compound of description 93 (0.70 g) according to the method of description 92.

Mass Spectrum (API$^+$): Found 241 (MH$^+$). $C_{15}H_{19}N_3$ requires 241.

Description 95 (RS)-1-Benzyl-2-[3-(4-fluoro-phenyl)-pyrazol-1-ylmethyl-piperidine The title compound (0.8 g) was prepared from 2-bromomethyl-N-benzylpiperidine (2.68 g) and 3-(4-fluoro-phenyl)-1H-pyrazole (1.62 g) according to the method of example 93.

Mass Spectrum (API$^+$): Found 350 (MH$^+$). $C_{22}H_{24}FN_3$ requires 349.

Description 96 (RS)-2-[3-(4-Fluoro-phenyl)-pyrazol-1-ylmethyl]-piperidine

The title compound (0.5 g) Was prepared form the compound of description 95 (0.8 g) according to the method of description 94.

Mass Spectrum (API$^+$): Found 260 (MH$^+$). $C_{15}H_{18}FN_3$ requires 259.

Description 97 (RS)-2 Carbamoylmethyl-piperidine-1-carboxylic acid tert butyl ester The title compound (0.92 g) wvas prepared from 2-(RS)-carboxymethyl-piperidine-1-carboxylic acid tert butyl ester (2.0 g) and ammonium chloride (0.86 g) according to the method of Example 97.

Mass Spectrum (API$^+$): Found 143 (MH$^+$-$C_5H_8O_2$). $C_{12}H_{22}N_2O_3$ requires 242.

Description 98
(RS)-2-Thiocarbamoylmethyl-piperidine-1-carboxylic acid tert butyl ester The compound of description 97 (0.90 g) and Lawesson's reagent (0.90 g) were combined in dry toluene (30 ml) and heated at 100° C. (oil bath temperature) for 6 h. Solvent was removed at reduced pressure and the residue column chromatographed (silica gel; dichloromethane eluant) to give after combining appropriate fractions the title compound (0.82 g) after tbiturationi with petroleum ether/diethyl ether.

Mass Spectrum (API$^+$): Found 159 (MH$^+$-C$_5$H$_8$O$_2$). C$_{12}$H$_{22}$N$_2$O$_2$S requires 258.

Description 99 (RS)-2-(4-Phenyl-thiazol-2-ylmethyl)-piperidine

The compound of description 98 (0.67 g) and 2-bromoacetophenone (0.52 g) were combined in ethanol (20 ml), stirred at room temperature for 8 h and then boiled for 48 h. Solvent was removed at reduced pressure and the residue column chromatographed (silica gel; ethyl acetate/n-pentane→1% ammonia/methanol/dichloromethane) to give the title compound (0.21 g)

Mass Spectrum (API$^+$): Found 259 (MH$^+$). C$_{15}$H$_{18}$N$_2$S requires 258.

Description 100 (RS)-(1-{1-[5-(4-Fluoro-phenyl)-2-methyl-thiazol-4-yl]-methanoyl}-piperidin-2-yl)-acetic acid hydrazide The title compound (0.24 g) was prepared from (1-{1-[5-(4-fluoro-phenyl)-2-methyl-thiazol-4-yl]-methanoyl}-piperidin-2-yl)-acetic acid methyl ester (0.25 g) according to the method of description 17.

Mass Spectrum (API$^+$): Found 377 (MH$^+$). C$_{18}$H$_{21}$N$_4$O$_2$FS requires 376.

Description 101 (RS-2,5-Dimethyl-2H-pyrazole-3-carboxylic acid N'-[2-(1-{1-[5-(4-fluoro-phenyl)-2-methyl-thiazol-4-yl]-methanoyl}-piperidin-2-yl)-ethanoyl]-hydrazide The title compound (0.36 g) was prepared from the compound of description 100 (0.23 g) and 1,3-dimethylpyrazole-5-carboxylic acid according to the method of description 20.

Mass Spectrum (API$^+$): Found 497 (MH$^+$). C$_{24}$H$_{27}$N$_6$O$_3$FS requires 498.

Description 102 (RS)-(1-{1-[5-(4-Fluoro-phenyl)-2-methyl-thiazol-4-yl]-methanoyl}-piperidin-2-yl)-acetic acid 2-oxo-1,2-diphenyl-ethyl The title compound (0.54 g) was prepared from the compound of description 35 (0.40 g) and desyl bromide (0.30 g) according to the method of example 36

Mass Spectrum (API$^+$): Found 557 (MH$^+$). C$_{32}$H$_{29}$FN$_2$O$_4$S requires 556.

Description 103 (RS)-2-{2-[N'-(1-Benzofuran-2-yl-methanoyl)-hydrazinol-2-oxo-ethyl}-piperidine-1-carboxylic acid tert butyl ester The title compound (2.4 g) was prepared from the compound of description 17 and benzofuran-2-carboxylic acid according to the method of description 20.

Mass Spectrum (API$^+$): Found 402 (MH$^+$). C$_{21}$H$_{27}$N$_3$O$_5$ requires 401.

Description 104 (RS)-2-(5-Benzofuran-2-yl-[1,3,4]oxadiazol-2-ylmethyl)-piperidine The title compound (0.77 g) was prepared from the compound of description. 103 according to the method of description 19.

Mass Spectrum (API$^+$): Found 284 (MH$^+$). C$_{16}$H$_{17}$N$_3$O$_2$ requires 283.

Description 105 (RS)-2-{1-[5-(4 Fluoro-phenyl)-2-methyl-thiazol4-yl]-methanoyl}-piperidin-2-yl)-acetamide The compound of description 34 (0.87 g) and formamide (0.3 ml) were combined in tetrahydrofuran and boiled while adding 3 portions of sodium methoxide (0.12 ml each addition, 20% in methanol) over 20 min. After the final addition the reaction was heated for a further 6 h at reflux. The reaction was cooled to room temperature diluted with dichloromethane and water and the aqueous phase separated. The organic phase was washed with water dried (MgSO$_4$) and solvent removed at reduced pressure to give the title compound (1.40 g)

Mass Spectrum (API$^+$): Found 362 (MH$^+$). C$_{18}$H$_{20}$FN$_3$O$_2$S requires 361.

Description 106 (RS)-(1-{1-[5-(3,4-Difluoro-phenyl)-2-methyl-thiazol-4-yl]-methanoyl}-piperidin-2-yl)-acetic acid 2-(4fluoro-phenyl)-2-oxo-ethyl ester The title compound (0.435 g) was prepared from the compound of description 35 (0.40 g) and 2-bromo-3',4'-difluoroacetophenone (0.26 g) according to the method of description 36.

Mass Spectrum (API$^+$): Found 517 (MH$^+$). C$_{24}$H$_{23}$F$_3$N$_2$O$_4$S requires 516.

Description 107 (RS)-(1-{[5-(3-Fluoro-pbenyl)-2-methyl-thiazol-4-yl]-methanoyl}-piperidin-2-yl)-acetic acid 2-(4-fluoro-phenyl)-2-oxo-ethyl ester The title compound (0.430 g) was prepared from the compound of description 35 (0.40 g) and 2-bromo-3'-fluoroacetophenone (0.240 g) according to the method of description 36

Mass Spectrum (API$^+$): Found 499 (MH$^+$). C$_{24}$H$_{24}$F$_2$N$_2$O$_4$S requires 498.

Description 108. (RS)1-(4-Fluorophenyl)-4-(1-{1-[5-(4 fluorophenyl)-2-methylthiazol-4-yl]methanoyl}-piperidin-2-yl)-butane-1,3-dione A. (1-{1-[5(4-fluorophenyl)-2-methylthiazol4-yl]-methanoyl}-piperidin-2-yl)-acetic acid (0.500 g) was dissolved in dry tetrahydrofuran (15 ml) and cooled to −20° C. under an atmosphere of argon. Triethylamine (0.231 ml) and isobutylchloroformate (0.215 ml) were added and the solution was stirred at −20° C. for 1 hour. The solution was then cooled to −78° C.

B. A solution of 4'-fluoroacetophenone (0.229 g) in THF (15 ml) was cooled to −20° C. under an atmosphere of argon. A solution of lithium diisopropylamide (0.830 ml; 2M solution in THF) was added and stirring continued at −20° C. for 30 minutes. The solution was then cooled to −78° C.

C. The solution from part B was added to the stirred solution of part A by way of a cannula. Stirring was continued at −78° C. under an atmosphere of argon for 2 hours before being quenched by the addition of saturated ammonium chloride solution. After reaching room temperature, the reaction solution was partitioned between ethyl acetate and water. The organic solution was washed with brine dried (MgSO$_4$) and evaporated. The residue was chromatographed over silica gel, eluting with a gradient of 10 to 75% ethyl acetate in hexane. The title compound was obtained as a colourless oil (0.560 g) mass spectrum (API$^+$) 483 [MH$^+$], (API$^-$) 481 [(M−H)$^-$] $C_{26}H_{24}F_2N_2O_3S$ requires 482.

Description 109. (RS)-2-Carboxymethylpiperazine-1,4-dicarboxylic acid 4-tert-butyl ester 1-(9H-fluoren-9-ylmethyl) ester 3-Methoxycarbonylmethylpiperazine-1-carboxylic acid tert-butyl ester (6.0 g) was dissolved in TBF (60 ml) and 1N sodium hydroxide solution (60 ml) and stirred at room temperature for 6 hours. The solution was then cooled to 5° C. and adjusted to pH 9-10 by the addition of 10% hydrochloric acid. Nα(9-Fluorenylmethoxycarbonyl chloride (6.05 g) was then added portionwise, maintaining the pH at 9-10 by the addition of 1N NaOH solution. The reaction mixture was stirred at 5° C. for 16 hours. The solution was then adjusted to pH 1 by the addition of 10% hydrochloric acid. The solution was extracted with ethyl acetate (×2), dried (MgSO$_4$) and evaporated. The title compound was obtained as a white foam (9.96 g), mass spectrum (API$^+$) 411 [(M−C$_4$H$_8$)H$^+$], $C_{26}H_{30}N_2O_6$ requires 466.

Description 110 (RS)-3-[2-(4-Fluorophenyl)-2-oxo-ethoxycarbonylmethyl]piperazine-1-carboxylic acid tert-butyl ester (RS)-2-Carboxymethylpiperazine-1,4-dicarboxylic acid 4-tert-butyl ester 1-(9H-fluoren-9-ylmethyl) ester from description 109 (2.0 g) was dissolved in DMF (25 ml) and stirred at room temperature under argon for 3 days in the presence of potassium carbonate (0.697 g) and 2-bromo-4'-fluoroacetophenone (0.930 g). The reaction solution was then partitioned between ethyl acetate and water the organic solution was washed with brine, dried (MgSO$_4$) and evaporated. The crude product was chromatographed over silica gel, eluting with 25 to 100% ethyl acetate in hexane, followed by 10% ethanol in ethyl acetate. The title compound was obtained as a pale yellow solid (0.887 g), mass spectrum (API$^+$) 381 [MH$^+$], $C_{19}H_{25}FN_2O_5$ requires 380.

Description 111. (RS)-4-{1-[5-(4-Fluorophenyl)-2-methylthiazol-4-yl]-methanoyl}-3-[2-(4-fluoro-phenyl)-2-oxo-ethoxycarbonylmethyl]-piperazine-1-carboxylic acid tert-butyl ester (RS)-3-[2-(4-Fluorophenyl)-2-oxo-ethoxycarbonylmethyl]-piperazine-1-carboxylic acid tert-butyl ester description 110 (0.887 g) was reacted with HATU (0.932 g), diisopropylethylamine (1.30 ml) and 5-(4-fluoro-phenyl)-2-methyl-thiazole-4-carboxylic acid (0.707 g) in dry DMF (8 ml) according to the method of description 20. Silica gel column chromatography, eluting with ethyl acetate-hexane mixtures provided the title compound as a white foam (1.168 g), mass spectrum (API$^+$) 600 [MH$^+$], $C_{30}H_{31}F_2N_3O_6S$ requires 599.

Description 112. (RS)-3-[4-(4-Fluorophenyl-1H-imidazol-2-ylmethyl]-4-{1-[5-(4-fluorophenyl)-2-methylthiazol-4-yl]-methanoyl}-piperazine-1-carboxylic acid tert-butyl ester (RS)-4-{1-[5-(4-Fluorophenyl)-2-methylthiazol-4-yl]-methanoyl}-3-[2-(4-fluoro-phenyl)-2-oxo-ethoxycarbonyl-methyl]-piperazine-1-carboxylic acid tert-butyl ester from description 111 (0.360 g) and anhydrous ammonium acetate were heated to 140° C. under argon for 1.5 hours with stirring. After cooling, the reaction mixture was partitioned between dichloromethane and saturated potassium carbonate solution. The organic solution was washed with brine, dried (MgSO$_4$) and evaporated. The residue was chromatographed over silica gel, eluting with 0 to 10% ethanol in ethyl acetate. The title compound was obtained as a white foam (0.125 g), mass spectrum (API$^+$) 580 [MH$^+$], $C_{30}H_{31}F_2N_5O_3S$ requires 579.

Description 113. (RS)-4-{1-[5-(4-Fluorophenyl)-2-methylthiazol-4-yl]-methanoyl}-3-[4-(4-fluoro-phenyl)-oxazol-2-ylmethyl]-piperazine-1-carboxylic acid tert-butyl ester (RS)-4-{1-[5(4-Fluorophenyl)-2-methylthiazol4-yl]-methanoyl}-3-[2-(4-fluoro-phenyl)-2-oxo-ethoxycarbonyl-methyl]-piperazine-1-carboxylic acid tert-butyl ester, description 111 (0.385 g), tert-butyl carbamate (0.376 g) and boron trifluoride etherate (4 drops) were dissolved in xylene (5 ml) and heated to 140° C., under argon and with stirring for 48 hours. After cooling, the reaction mixture was partitioned between ethyl acetate and saturated sodium hydrogen carbonate solution. The organic layer was dried (MgSO$_4$), evaporated and the residue chromatographed over silica gel. Elution with a gradient of 25 to 100% ethyl acetate in hexane provided the title compound as a pale yellow oil (0.130 g), mass spectrum (API$^+$) 581 [MH$^+$], $C_{30}H_{30}F_2N_4O_4S$ requires 580.

Description 114. (S)-2-Methoxycarbonylmethyl-pyrrolidine-1-carboxylic acid tert-butyl ester A solution of (S)-2-carboxymethyl-pyrrolidine-1-carboxylic acid tert-butyl ester (2.00 g) in methanol (1.32 ml)/acetonitrile (40 ml) was treated with N,N-diisopropylethylamine (1.78 ml). Trimethylsilyldiazomethane, (2M, 8.73 ml) was added dropwise and the resulting mixture was stirred at room temperature, under argon for 24 h. The mixture was diluted with ethyl acetate, washed with 2M HCl, saturated aqueous sodium hydrodgen carbonate, brine then dried (magnesium sulfate). The solvent was removed under reduced pressure to afford the title compound (2.10 g)

Mass Spectrum (API$^+$): 144 (MH$^+$-$^t$BOC). $C_{12}H_{21}NO_4$ requires 243.

Description 115. (S)-2-Hydrazinocarbonylmethyl-pyrrolidine-1-carboxylic acid tert-butyl ester The ester of description 114 (2.10 g) was treated with hydrazine hydrate (16.3 ml) as described in description 78 to afford the title compound (1.60 g).

Mass Spectrum (API$^+$): 144 (MH$^+$-$^t$BOC). $C_{11}H_{21}N_3O_3$ requires 243.

Description 116. (S)-2-(5-Phenyl-4H-[1,2,4]triazol-3-ylmethyl)-pyrrolidine-1-carboxylic acid tert-butyl ester Benzamidine.hydrochloride (0.84 g) in ethanol (20 ml) was treated with 25% sodium methoxide solution in methanol (2.44 ml) and stirred for 45 min. at room temperature under argon. The hydrazide of description 115 (1.3 g) was added and the mixture was heated at reflux for 24 h. After cooling the solvent was removed under reduced pressure then the residue was partitioned between dichloromethane and water. The organic phase was dried (MgSO$_4$) and the solvent removed under reduced pressure. The residue was column chromatographed (silica gel; 0→50% ethyl acetate-pentane) to afford the title compound (0.26 g).
Mass Spectrum (API$^+$): 329 (MH$^+$). $C_{18}H_{24}N_4O_2$ requires 328.

Description 117. 3-Phenyl-5-(S)-1-pyrrolidin-2-ylmethyl-4H-[1,2,4]triazole

The compound of description 116 (0.13 g) was treated with trifluoroacetic acid (2.5 ml) according to a method similar to that of description 2 to afford the title compound (0.09 g).
Mass Spectrum (API$^+$): 229 (MH$^+$). $C_{13}H_{16}N_4$ requires 228.

Description 118. (S)-2-(2-Oxo-2-phenyl-ethoxycarbonylmethyl)-pyrrolidine-1-carboxylic acid benzyl ester The title compound (0.700 g) was prepared from (S)-2-carboxymethyl-pyrrolidine-1-carboxylic acid benzyl ester (1.00 g, Aoyama et al, Chem. Pharm. Bull., 3249, 29,11, 1981) and 2-bromoacetophenone (0.760 g) according to the method of description 36.
Mass Spectrum (API$^+$): 382 (MH$^+$). $C_{22}H_{23}NO_5$ requires 381.

Description 119. (S)-2(4-Phenyl-oxazol-2-ylmethyl)-pyrrolidine-1-carboxylic acid benzyl ester The title compound (0.290 g) was prepared from the compound of description 118 (0.700 g) according to the method of example 54 using xylene as solvent.
Mass Spectrum (API$^+$): 363 (MH$^+$). $C_{22}H_{22}N_2O_3$ requires 362.

Description 120. 4-Phenyl-2-(S)-1-pyrrolidin-2-ylmethyl-oxazole

The title compound (0.065 g) was prepared by treating the compound of description 119 (0.280 g) with 10% palladium/charcoal (0.150 g, 50% paste) according to the method of description 77. The product was purified by column chromatography (silica gel, 0→4% (10% 0.880 ammonia-methanol)-dichloromethane).
Mass Spectrum (API$^+$): 229 (MH$^+$). $C_{14}H_{16}N_2O$ requires 228.

Description 121. (RS)-(1-{1-[5-(4-Fluoro-phenyl)-2-methyl-thiazol-4-yl]-methanoyl}-piperidin-2-yl)-acetic acid 2-(2-bromo-phenyl)-2-oxo-ethyl ester The title compound (3.0 g) was prepared as a brown oil from the acid of description 35 (2.5 g) and (2-bromo-phenyl)-acetyl bromide (1.92 g) according to the method of description 36.

Mass Spectrum (API$^+$): Found 559,561 (MH$^+$). $C_{26}H_{24}BrFN_2O_4S$ requires 558,560.

Description 122. (RS)-2-[4-(2-Fluoro-phenyl)-thiazol-2-ylmethyl]-piperidine

The title compound (0.335 g) was prepared as an oil from the compound of description 98 (0.750 g) and 2-bromo-1-(2-fluoro-phenyl)ethanone (0.631 g) according to the method of description 99.
Mass Spectrum (API$^+$): Found 277. (MH$^+$). $C_{15}H_{17}FN_2S$ requires 276.

Description 123. (RS)-2-[4-(3-Fluoro-phenyl)-thiazol-2-ylmethyl]-piperidine

The title compound (0.310 g) was prepared as an oil from the compound of description 98 (0.750 g) and 2-bromo-1-(3-fluoro-phenyl)-ethanone (0.631 g) according to the method of description 99.
Mass Sprectrun (API$^+$): Found 277. (MH$^+$). $C_{15}H_{17}FN_2S$ requires 276.

EXAMPLE 1

(RS)-1-[5-(4 Fluoro-phenyl)-2-methyl-thiazol-4-yl]-1-[2-(5-phenyl-[1,3,4]oxadiazol-2-ylwethyl)-piperidin-1-yl]-methanone 2-Methyl-5-(4-fluorophenyl)-thiazole-4-carboxylic acid (0.07 g), [O-(7-azabenzotriazol-1-yl)-1,1,3,3-tetramethyluronium hexafluorophosphate] (0.12 g) and diisopropylaethylamine (0.17 ml) in dimethylformamide (5 ml) was stirred for 15 min. The amine of D2 (0.075 g) was added and the mixture stirred for 16 h. Solvent was removed at reduced pressure, the residue dissolved in ethyl acetate and washed with water. The organic phase was separated dried (MgSO$_4$) and solvent removed at reduced pressure. The residue was column chromatographed (silica get, 0-100% ethyl acetate/pentane) to give the title compound (0.095 g).
Mass Spectrum (API$^+$): Found 463 (MH$^+$). $C_{25}H_{23}FN_4O_2S$ requires 462.

EXAMPLE 2

(RS)-1-[5-(4-Fluoro-phenyl)-2-methyl-2H-[1,2,3]triazol-4-yl]-1-[2-(5-phenyl-[1,3,4]oxadiazol-2-ylmethyl)-piperidin-1-yl]-methanone A mixture of 5-(4-Fluoro-phenyl)-2-methyl-2H-[1,2,3]triazole-4-carbonyl chloride (0.11 5 g) and the amine D2 were combined in dichloromethane (10 ml) containing triethyl amine (0.2 ml). The mixture was stirred for 16 h, washed with water, the organic phase dried (MgSO$_4$) and solvent removed at reduced pressure. The residue was column chromatographed (silica get, 40-60% ethyl acetate/pentane eluant) to give the title compound (0.154 g).
Mass Spectrum (API$^+$): Found 447 (MH$^+$). $C_{24}H_{23}FN_6O_2$ requires 446.

The compounds of the examples of Table 1 were prepared by analogous procedures to those used to prepare the compounds of Example 1 and Example 2 from the corresponding amine and carboxylic acid (Method 1) or from the corresponding amine and acid chloride Method 2).

TABLE 1

5-Aryl-[1,3,4]oxadiazol-2-ylpiperidines

| Example | Amine | Method | Ar² | R² | yield % | Mass Spectrum (Electrospray LC/MS) |
|---|---|---|---|---|---|---|
| 3 | D2 | 1 | 3-methyl-5-(2-...)-1,2,4-oxadiazole | phenyl | 56 | Found 430(MH⁺). $C_{24}H_{23}N_5O_3$. requires 429 |
| 4 | D2 | 2 | 1-naphthyl | phenyl | 86 | Found 398(MH⁺). $C_{25}H_{23}N_3O_2$. requires 397 |
| 5 | D2 | 2 | 1-(4-fluorophenyl)-3-methyl-pyrazol-5-yl | phenyl | 79 | Found 446(MH⁺). $C_{25}H_{24}FN_5O_2$. requires 445 |
| 6 | D2 | 2 | 4-(4-fluorophenyl)-1-methyl-pyrazol-3-yl | phenyl | 64 | Found 446(MH⁺). $C_{25}H_{24}FN_5O_2$. requires 445 |

TABLE 1-continued
5-Aryl-[1,3,4]oxadiazol-2-ylpiperidines
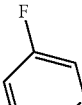
| Example | Amine | Method | Ar² | R² | yield % | Mass Spectrum (Electrospray LC/MS) |
|---|---|---|---|---|---|---|
| 7 | D2 | 2 | 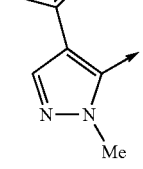 | 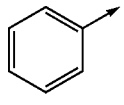 | 42 | Found 446(MH⁺). $C_{25}H_{24}FN_5O_2$. requires 445 |
| 8 | D2 | 2 | 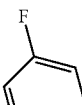 | 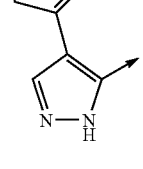 | 53 | Found 432(MH⁺). $C_{24}H_{22}FN_5O_2$. requires 431 |
| 9 | D4 | 1 | 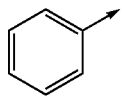 | 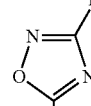 | 56 | Found 448(MH⁺). $C_{24}H_{22}FN_5O_2$. requires 447 |
| 10 | D4 | 1 | 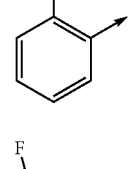 | 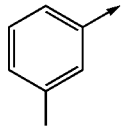 | 77 | Found 481(MH⁺). $C_{25}H_{22}F_2N_4O_2S$. requires 480 |

TABLE 1-continued
5-Aryl-[1,3,4]oxadiazol-2-ylpiperidines
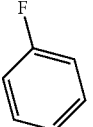
| Example | Amine | Method | Ar² | R² | yield % | Mass Spectrum (Electrospray LC/MS) |
|---------|-------|--------|-----|-----|---------|-------------------------------------|
| 11 | D6 | 1 | 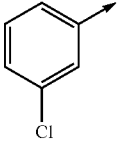 | 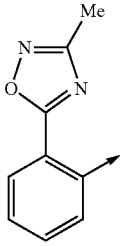 | 54 | Found 497, 499 (MH⁺). $C_{25}H_{22}ClFN_4O_2S$. requires 496, 498 |
| 12 | D6 | 1 | 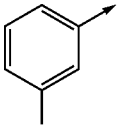 | 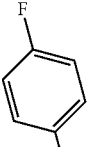 | 57 | Found 464, 466 (MH⁺). $C_{24}H_{22}ClN_5O_3$. requires 463, 465 |
| 13 | D8 | 1 | 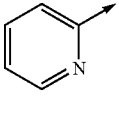 | 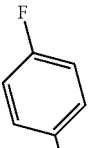 | 59 | Found 464(MH⁺). $C_{24}H_{22}FN_5O_2S$. requires 463 |
| 14 | D10 | 1 | 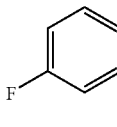 | | 64 | Found 481(MH⁺). $C_{25}H_{22}F_2N_4O_2S$. requires 480 |

TABLE 1-continued
5-Aryl-[1,3,4]oxadiazol-2-ylpiperidines
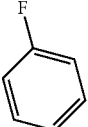
| Example | Amine | Method | Ar² | R² | yield % | Mass Spectrum (Electrospray LC/MS) |
|---|---|---|---|---|---|---|
| 15 | D12 | 1 | 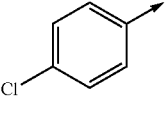 | 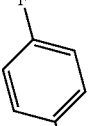 | 71 | Found 497, 499 (MH⁺). $C_{25}H_{22}ClFN_4O_2S$. requires 496, 498 |
| 16 | D14 | 2 | 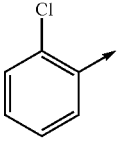 | 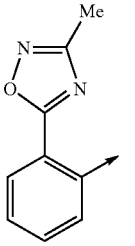 | 79 | Found 497, 499 (MH⁺). $C_{25}H_{22}ClFN_4O_2S$. requires 496, 498 |
| 17 | D14 | 2 | 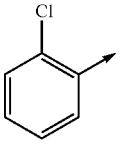 | 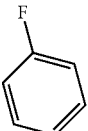 | 7 | Found 464, 466 (MH⁺). $C_{24}H_{22}ClN_5O_3$. requires 463, 465 |
| 18 | D16 | 2 | 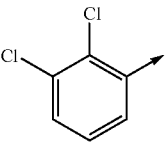 | | 62 | Found 532, 534, 466(MH⁺). $C_{25}H_{21}Cl_2FN_4O_2S$. requires 531, 533 |

TABLE 1-continued
5-Aryl-[1,3,4]oxadiazol-2-ylpiperidines
| Example | Amine | Method | Ar² | R² | yield % | Mass Spectrum (Electrospray LC/MS) |
|---|---|---|---|---|---|---|
| 19 | D19 | 1 |  |  | 63 | Found 481(MH⁺). $C_{25}H_{22}F_2N_4O_2S$. requires 480 |
| 20 | D21 | 1 | 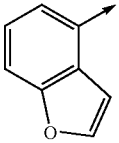 |  | 6 | Found 503(MH⁺). $C_{27}H_{23}FN_4O_3S$. requires 502 |
| 21 | D19 | 1 |  |  | 52 | Found 464(MH⁺). $C_{25}H_{23}F_2N_5O_2$. requires 463 |
| 22 | D19 | 1 | 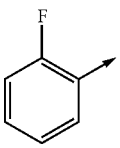 | | 44 | Found 465(MH⁺). $C_{24}H_{22}F_2N_6O_2$. requires 464 |

TABLE 1-continued
5-Aryl-[1,3,4]oxadiazol-2-ylpiperidines
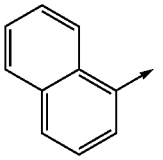
| Example | Amine | Method | Ar² | R² | yield % | Mass Spectrum (Electrospray LC/MS) |
|---------|-------|--------|-----|-----|---------|-----------------------------------|
| 23 | D19 | 1 | 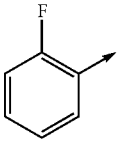 | 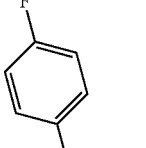 | 50 | Found 416(MH⁺). $C_{25}H_{22}FN_3O_2$. requires 415 |
| 24 | D23 | 1 | 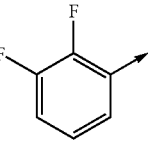 | 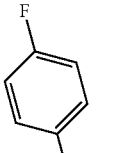 | 69 | Found 499(MH⁺). $C_{25}H_{21}F_3N_4O_2S$. requires 498 |
| 25 | D2 | 1 | 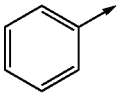 | 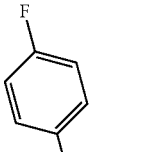 | 54 | Found 446(MH⁺). $C_{25}H_{24}FN_5O_2$. requires 445 |
| 26 | D25 | 1 | 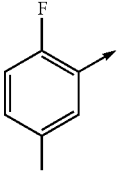 |  | 56 | Found 499(MH⁺). $C_{25}H_{21}F_3N_4O_2S$. requires 498 |

TABLE 1-continued

5-Aryl-[1,3,4]oxadiazol-2-ylpiperidines

| Example | Amine | Method | Ar² | R² | yield % | Mass Spectrum (Electrospray LC/MS) |
|---------|-------|--------|-----|-----|---------|-------------------------------------|
| 27 | D25 | 1 | 4-F-phenyl-pyrazol-3-yl (NH) | 2,5-difluorophenyl | 50 | Found 468(MH⁺). C₂₄H₂₀F₃N₅O₂. requires 467 |
| 28 | D25 | 1 | 4-F-phenyl-N-methyl-pyrazol-3-yl | 2,5-difluorophenyl | 44 | Found 482(MH⁺). C₂₅H₂₂F₃N₅O₂. requires 481 |
| 29 | D27 | 1 | 5-(4-F-phenyl)-2-methyl-thiazol-4-yl | 3,5-difluorophenyl | 69 | Found 499(MH⁺). C₂₅H₂₁F₃N₄O₂S. requires 498 |
| 30 | D27 | 1 | 5-(4-F-phenyl)-thiazol-4-yl | 3,5-difluorophenyl | 65 | Found 485(MH⁺). C₂₄H₁₉F₃N₄O₂S. requires 484 |

TABLE 1-continued
5-Aryl-[1,3,4]oxadiazol-2-ylpiperidines
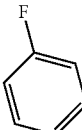
| Example | Amine | Method | Ar² | R² | yield % | Mass Spectrum (Electrospray LC/MS) |
|---------|-------|--------|-----|-----|---------|-----------------------------------|
| 31 | D27 | 1 | 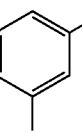 | 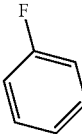 | 56 | Found 468(MH⁺). $C_{24}H_{20}F_3N_5O_2$. requires 467 |
| 32 | D27 | 1 | 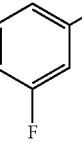 | 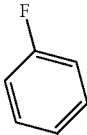 | 44 | Found 482(MH⁺). $C_{25}H_{22}F_3N_5O_2$. requires 481 |
| 33 | D29 | 2 |  | 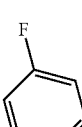 | 44 | Found 478(MH⁺). $C_{25}H_{24}FN_5O_2S$. requires 477 |
| 34 | D29 | 2 |  | Me-pyridyl | 23 | Found 447(MH⁺). $C_{24}H_{23}FN_6O_2$. requires 446 |

TABLE 1-continued
5-Aryl-[1,3,4]oxadiazol-2-ylpiperidines
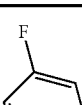
| Example | Amine | Method | Ar² | R² | yield % | Mass Spectrum (Electrospray LC/MS) |
|---------|-------|--------|-----|-----|---------|-----------------------------------|
| 35 | D29 | 2 | 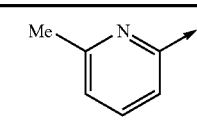 | 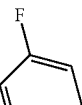 | 29 | Found 461(MH⁺). $C_{25}H_{25}FN_6O_2$. requires 460 |
| 36 | D4 | 2 | 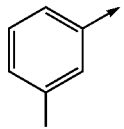 | 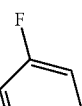 | 77 | Found 467(MH⁺). $C_{24}H_{20}F_2N_4O_2S$. requires 466 |
| 37 | D31 | 2 | 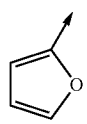 | 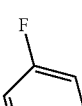 | 40 | Found 453(MH⁺). $C_{23}H_{21}FN_4O_3S$. requires 452 |
| 38 | D31 | 2 | 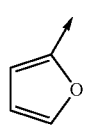 | | 45 | Found 422(MH⁺). $C_{22}H_{20}FN_5O_3$. requires 421 |

TABLE 1-continued
5-Aryl-[1,3,4]oxadiazol-2-ylpiperidines
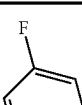
| Example | Amine | Method | Ar² | R² | yield % | Mass Spectrum (Electrospray LC/MS) |
|---|---|---|---|---|---|---|
| 39 | D31 | 2 | 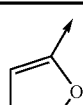 | 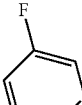 | 50 | Found 436(MH⁺). C$_{23}$H$_{22}$FN$_5$O$_3$. requires 435 |
| 40 | D31 | 2 | 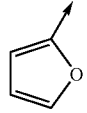 | 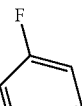 | 53 | Found 437(MH⁺). C$_{22}$H$_{21}$FN$_6$O$_3$. requires 436 |
| 41 | D4 | 2 | 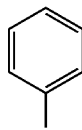 | 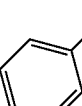 | 77 | Found 467(MH⁺). C$_{24}$H$_{20}$F$_2$N$_4$O$_2$S. requires 466 |
| 42 | D4 | 1 | 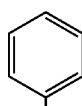 | | 69 | Found 481(MH⁺). C$_{25}$H$_{22}$F$_2$N$_4$O$_2$S. requires 480 |

TABLE 1-continued
5-Aryl-[1,3,4]oxadiazol-2-ylpiperidines
| Example | Amine | Method | Ar² | R² | yield % | Mass Spectrum (Electrospray LC/MS) |
|---------|-------|--------|-----|-----|---------|------------------------------------|
| 43 | D4 | 2 | 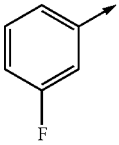 | 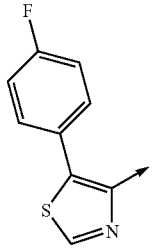 | 85 | Found 481(MH⁺). C$_{25}$H$_{22}$F$_2$N$_4$O$_2$S. requires 480 |
| 44 | D2 | 2 | 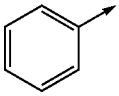 | 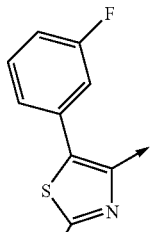 | 76 | Found 449(MH⁺). C$_{24}$H$_{21}$FN$_4$O$_2$S. requires 448 |
| 45 | D2 | 1 | 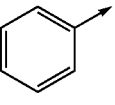 | 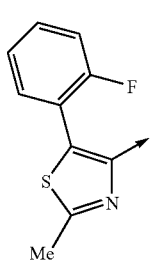 | 69 | Found 463(MH⁺). C$_{25}$H$_{23}$FN$_4$O$_2$S. requires 462 |
| 46 | D2 | 2 | 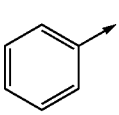 | | 80 | Found 463(MH⁺). C$_{25}$H$_{23}$FN$_4$O$_2$S. requires 462 |

TABLE 1-continued
5-Aryl-[1,3,4]oxadiazol-2-ylpiperidines
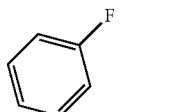
| Example | Amine | Method | Ar² | R² | yield % | Mass Spectrum (Electrospray LC/MS) |
|---------|-------|--------|-----|----|---------|-----------------------------------|
| 47 | D29 | 1 | 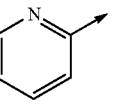 | 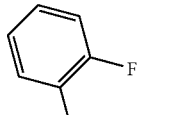 | 27 | Found 478(MH⁺). C$_{25}$H$_{24}$FN$_5$O$_2$S. requires 477 |
| 48 | D29 | 2 | 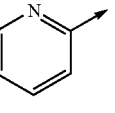 | 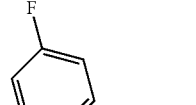 | 80 | Found 478(MH⁺). C$_{25}$H$_{24}$FN$_5$O$_2$S. requires 477 |
| 49 | D23 | 1 | 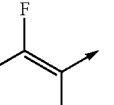 |  | 69 | Found 468(MH⁺). C$_{24}$H$_{20}$F$_3$N$_5$O$_2$. requires 467 |
| 50 | D23 | 1 | 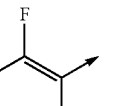 | | 72 | Found 482(MH⁺). C$_{25}$H$_{22}$F$_3$N$_5$O$_2$. requires 481 |

TABLE 1-continued
5-Aryl-[1,3,4]oxadiazol-2-ylpiperidines
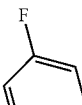
| Example | Amine | Method | Ar² | R² | yield % | Mass Spectrum (Electrospray LC/MS) |
|---|---|---|---|---|---|---|
| 181 | D23 | 1 | 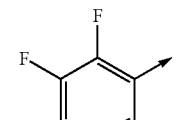 | 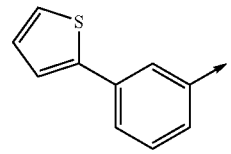 | 64 | Found 483(MH⁺). $C_{24}H_{21}F_3N_6O_2$. requires 482 |
| 125 | D4 | 1 | 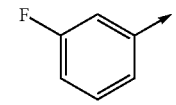 | 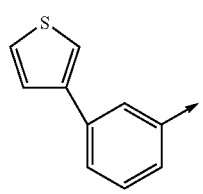 | | Found 448 (MH⁺). $C_{25}H_{22}FN_3O_2S$. requires 447 |
| 126 | D4 | 1 | 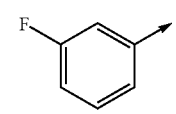 | 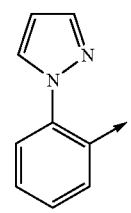 | | Found 448 (MH⁺). $C_{25}H_{22}FN_3O_2S$. requires 447 |
| 127 | D4 | 1 | 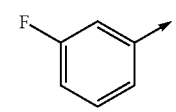 | 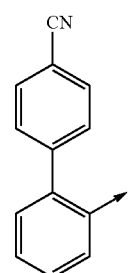 | | Found 432 (MH⁺). $C_{24}H_{22}FN_5O_2$. requires 431 |
| 128 | D4 | 1 | 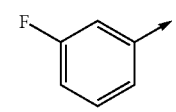 | | | Found 467 (MH⁺). $C_{28}H_{23}FN_4O_2$. requires 466 |

TABLE 1-continued
5-Aryl-[1,3,4]oxadiazol-2-ylpiperidines
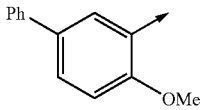
| Example | Amine | Method | Ar² | R² | yield % | Mass Spectrum (Electrospray LC/MS) |
|---------|-------|--------|-----|----|---------|--------------------------------------|
| 129 | D4 | 1 | 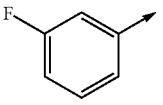 | 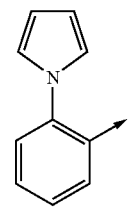 | | Found 472 (MH⁺). $C_{28}H_{26}FN_3O_3$. requires 471 |
| 130 | D4 | 1 | 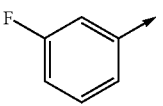 | 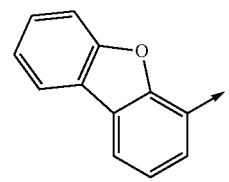 | | Found 431 (MH⁺). $C_{25}H_{23}FN_4O_2$. requires 430 |
| 131 | D4 | 1 | 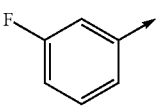 | 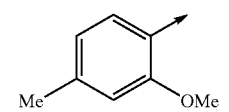 | | Found 456 (MH⁺). $C_{27}H_{22}FN_3O_3$. requires 455 |
| 132 | D4 | 1 | 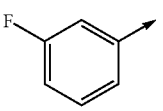 | 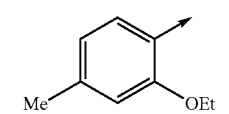 | | Found 410 (MH⁺). $C_{23}H_{24}FN_3O_3$. requires 409 |
| 133 | D4 | 1 | 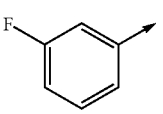 | 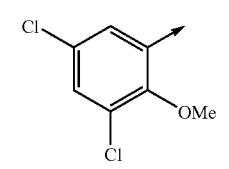 | | Found 424 (MH⁺). $C_{24}H_{26}FN_3O_3$. requires 423 |
| 134 | D4 | 1 | 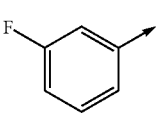 | | | Found 465 (MH⁺). $C_{22}H_{20}Cl_2FN_3O_3$. requires 464 |

TABLE 1-continued

5-Aryl-[1,3,4]oxadiazol-2-ylpiperidines

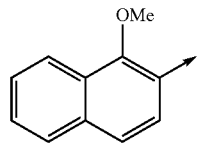

| Example | Amine | Method | Ar² | R² | yield % | Mass Spectrum (Electrospray LC/MS) |
|---|---|---|---|---|---|---|
| 135 | D4 | 1 | 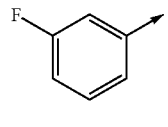 1-OMe naphthyl | 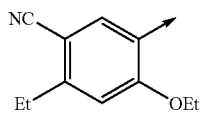 3-F phenyl | | Found 446 (MH⁺). $C_{26}H_{24}FN_3O_3$. requires 445 |
| 136 | D4 | 1 | 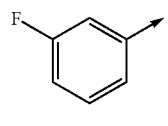 NC, Et, OEt substituted phenyl | 3-F phenyl | | Found 463 (MH⁺). $C_{26}H_{27}FN_4O_3$. requires 462 |
| 137 | D4 | 1 | 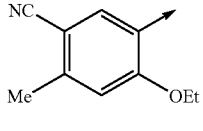 NC, Me, OEt substituted phenyl | 3-F phenyl | | Found 449(MH⁺). $C_{25}H_{25}FN_4O_3$. requires 448 |
| 138 | D4 | 1 | 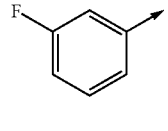 4'-OMe, 4-NO₂ biphenyl | 3-F phenyl | | Found 517(MH⁺). $C_{28}H_{25}FN_4O_5$. requires 516 |
| 139 | D4 | 1 | 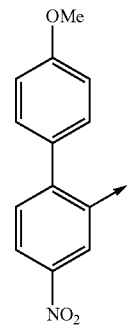 2'-Me, 4-NO₂ biphenyl | 3-F phenyl | | Found 501 (MH⁺). $C_{28}H_{25}FN_4O_4$. requires 500 |

TABLE 1-continued
5-Aryl-[1,3,4]oxadiazol-2-ylpiperidines
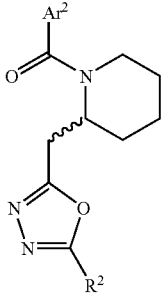
| Example | Amine | Method | Ar² | R² | yield % | Mass Spectrum (Electrospray LC/MS) |
|---|---|---|---|---|---|---|
| 140 | D4 | 1 | 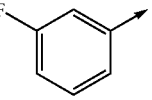 | 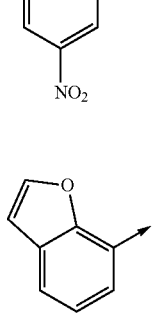 | | Found 487 (MH⁺). $C_{27}H_{23}FN_4O_4$. requires 486 |
| 141 | D4 | 1 | 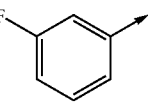 | 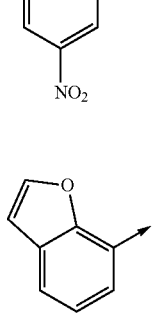 | | Found 406 (MH⁺). $C_{23}H_{20}FN_3O_3$. requires 405 |
| 142 | D4 | 1 | 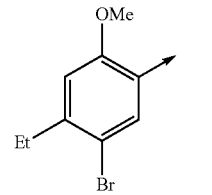 | 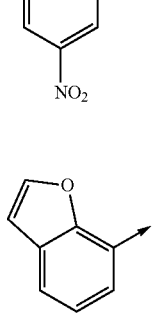 | | Found 502, 504 (MH⁺). $C_{24}H_{25}BrFN_3O_3$. requires 501, 503 |
| 143 | D2 | 1 | 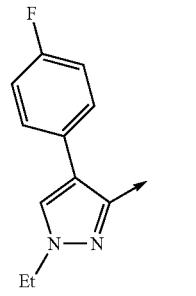 | 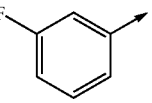 | 85% | Found 460 (MH⁺). $C_{26}H_{26}FN_5O_2$. requires 459 |

EXAMPLE 51

1-[5-(4-Fluoro-phenyl)-2-methyl-thiazol-4-yl]-1-[(S)-2-(5-phenyl-[1,3,4]oxadiazol-2-ylmethyl)-pyrrolidin-1-yl]-methanone The title compound (0.01 g) was prepared from the amine of description 33 (0.069 g) and 2-methyl-5-(4-fluorophenyl)-thiazole-4-carboxylic acid (0.07 g) according to the method of example 1.

Mass Spectrum (API$^+$):.

The compounds of the examples of Table 2 were prepared by analogous procedures to those used to prepare the compounds of example 51

TABLE 2

Pyrrolidine Aryl oxadiazoles

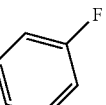

| Example | Amine | Ar$^2$ | R$^2$ | yield % | Mass Spectrum (Electrospray LC/MS) |
|---|---|---|---|---|---|
| 52 | D33 | 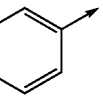 | 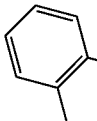 | 46 | Found 449(MH$^+$). C$_{24}$H$_{21}$FN$_4$O$_2$S requires 448 |

TABLE 2-continued

Pyrrolidine Aryl oxadiazoles

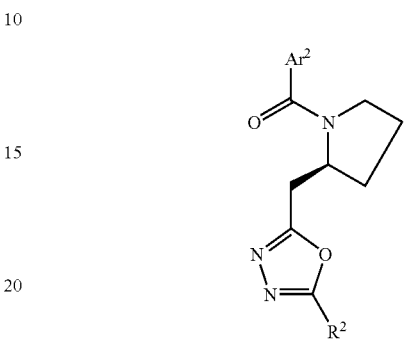

| Example | Amine | Ar$^2$ | R$^2$ | yield % | Mass Spectrum (Electrospray LC/MS) |
|---|---|---|---|---|---|
| 53 | D33 | 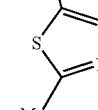 |  | 24 | Found 449(MH$^1$). C$_{24}$H$_{21}$FN$_4$O$_2$S requires 448 |

EXAMPLE 54

(RS)-R-[5-(4 Fluoro-phenyl)-2-methyl-thiazol-4-yl]-1-{2-[4-(4-fluoro-phenyl)-oxazol-2-ylmethyl]-piperidin-1-yl}-methanone Boron trifluoride diethyl etherate (4 drops) was added to a mixture of the ester of description 36 (0.264 g) and acetamide (0.156 g) in diethyl ether (2 ml). Xylene (1 ml) was added and the mixture heated to 140° C. for 22 h. The reaction mixture was cooled to room temperature, diluted with ethyl acetate and washed with water and brine. The organic phase was dried (MgSO$_4$) and solvent removed at reduced pressure the residue was column chromatographed (silica gel, 0→60% ethyl acetate/pentane eluant) to give the title compound (0.145 g)

Mass Spectrum (API$^+$): Found 480 (MH$^+$). C$_{26}$H$_{23}$F$_2$N$_3$O$_2$S requires 479

The compounds of the examples of Table 3 were prepared by analogous procedures to those used to prepare the compound of example 54

TABLE 3
Piperidine 2-(4-aryloxazoles)
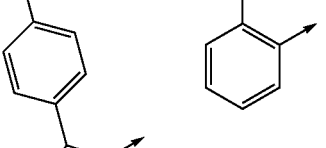
| Example | Ester | Ar² | R² | yield % | Mass Spectrum (Electrospray LC/MS) |
|---|---|---|---|---|---|
| 55 | D37 | 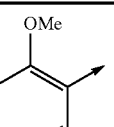 | OMe 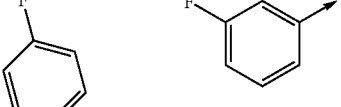 | 67 | Found 492(MH⁺). C$_{27}$H$_{26}$FN$_3$O$_3$S requires 491 |
| 56 | D38 | 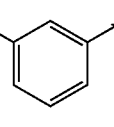 | 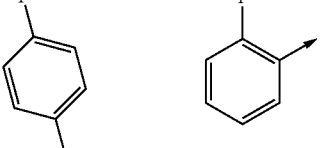 | 15 | Found 480(MH⁺). C$_{26}$H$_{23}$F$_2$N$_3$O$_2$S requires 479 |
| 57 | D39 | 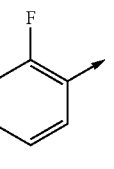 | 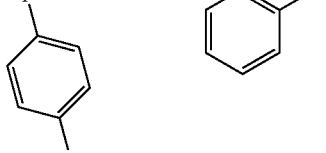 | 46 | Found 480(MH⁺). C$_{26}$H$_{23}$F$_2$N$_3$O$_2$S requires 479 |
| 60 | D46 | 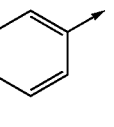 |  | 43 | Found 445(MH⁺). C$_{26}$H$_{25}$FN$_4$O$_2$ requires 444 |

TABLE 3-continued
Piperidine 2-(4-aryloxazoles)
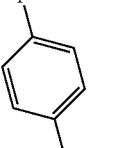
| Example | Ester | Ar² | R² | yield % | Mass Spectrum (Electrospray LC/MS) |
|---|---|---|---|---|---|
| 61 | D47 |  | 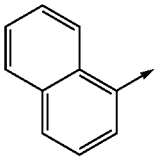 | 16 | Found 446(MH⁺). $C_{25}H_{24}FN_5O_2$ requires 445 |
| 62 | D48 |  | 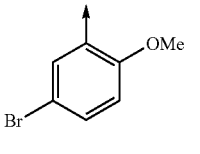 | 22 | Found 397(MH⁺). $C_{26}H_{24}N_2O_2$ requires 396 |
| 63 | D49 |  | 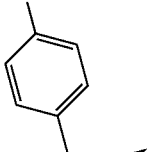 | 39 | Found 455, 457 (MH⁺). $C_{23}H_{23}BrN_2O_3$ requires 454, 456 |
| 70 | D50 |  | 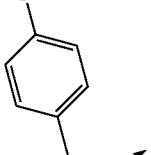 | 85 | Found 462(MH⁺). $C_{26}H_{24}FN_3O_2S$ requires 461 |
| 99 | D69 |  |  | 46 | Found 463 (MH⁺). $C_{26}H_{24}F_2N_4O_2$ requires 462 |

TABLE 3-continued

Piperidine 2-(4-aryloxazoles)

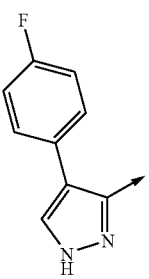

| Example | Ester | Ar² | R² | yield % | Mass Spectrum (Electrospray LC/MS) |
|---|---|---|---|---|---|
| 100 | D70 | 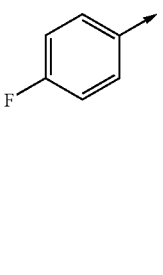 | 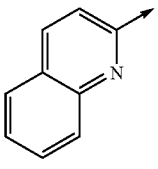 | 30 | Found 416 (MH⁺). $C_{25}H_{22}F_2N_4O_2$ requires 415 |
| 101 | D71 | 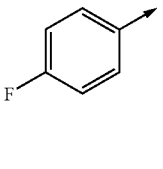 | 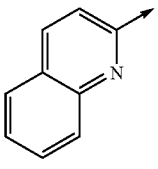 | 30 | Found 416 (MH⁺). $C_{25}H_{22}FN_3O_2$ requires 415 |

EXAMPLE 58

(RS)-1-[5(4-Fluoro-phenyl)-2-methyl-thiazol-4-yl]-1-[2-(5-methyl-4-phenyl-oxazol-2-ylmethyl)-piperidin-1-yl]-methanone The title compound (0.28 g) was prepared from the ester of description 40 (0.30 g) according to the method of example 54.

Mass Spectrum (API⁺): Found 476 (MH⁺). $C_{27}H_{26}FN_3O_2S$ requires 475

EXAMPLE 59

(RS)-2-(5-(4-Fluorophenyl)-furan-2-ylmethyl)-1-((5-(4-fluorophenyl)-2-methyl-thiazol-4-yl)carbonyl-piperidine 5-(4-Fluorophenyl)-2-methyl-thiazole-4-carbonyl chloride (115 mg, 0.425 mmol) in dichloromethane (1 ml) was added to a solution of (RS)-2-(5-(4-fluorophenyl)-furan-2-ylmethyl)-piperidine (100 mg, 0.386 mmol) and triethylamine (0.16 ml, 1.16 mmol) in dichloromethane (4 ml) and the mixture shaken at ambient temperature for 30 min. The reaction mixture was then washed with saturated aqueous sodium hydrogen carbonate (8 ml) and the organic layer applied directly onto a pre-packed silica gel column and chromatographed eluting with an ethyl acetate-hexane gradient to give the title compound as a yellow solid (78.0 mg, 42%).

Mass spectrum (API⁺): 479 (MH⁺): $C_{27}H_{24}F_2N_2O_2S$ requires 478.

EXAMPLE 64

(RS)-1-[5-(4-Fluoro-phenyl)-2-methyl-thiazol-4-yl]-1-[2-(5-phenyl-1H-imidazol-2-ylmethyl)-piperidin-1-yl]-methanone The compound of description 50 (0.30 g), ammonium acetate (0.38 g) and n-butanol (5 ml) were combined and boiled for 1 h. Solvent was removed at reduced pressure and the residue column chromatographed (silica gel, ethyl acetate then 3% methanol/ethyl acetate) to give the title compound (0.13 g).

Mass Spectrum (API⁺): Found 461 (MH⁺). $C_{26}H_{25}FN_4OS$ requires 460.

EXAMPLE 65

(RS)-1-[5-(4-Fluoro-phenyl)-2methyl-thiazol-4-yl]-1-{2-[3-(4-fluoro-phenyl)-[1,2,4]oxadiazol-5-ylmethyl]-piperidin-1-yl}-methanone The acid of description 35 (0.14 g) was dissolved in dichloromethane (10 ml) containing dimethylformamide (1 drop).

Oxalyl chloride (0.04 g) was added and the mixture stirred for 3 h. Solvent was removed at reduced pressure, the residue redissolved in dichloromethane (10 ml) and added to a solution of 4-fluorobenzanidoximo (0.06 g) in pyridine (0.3 ml). The mixture was stirred at room temperature for 10 min and boiled for 5 h. Solvent was removed at reduced pressure and the residue column chromatographied (silica gel, 20% ether in pentane→dichloromethane eluant) to give the title compound (0.03 g).

Mass Spectrum (API$^+$): Found 481 (MH$^+$). $C_{25}H_{22}F_2N_4O_2S$ requires 480.

EXAMPLE 66

(RS)-1-[5-(4-Fluoro-phenyl)-2-methyl-thiazol-4-yl]-1-[3-(5-phenyl-[1,3,4]oxadiazol-2-ylmethyl)-morpholin-4-yl]-methanone The title compound (0.29 g) was prepared from the compound of description 52 and 5-phenyltetrazole (0.10 g) according to the method of description 1.

Mass Spectrum (API$^+$): Found 465 (MH$^+$). $C_{24}H_{21}FN_4O_3S$ requires 464.

EXAMPLE 67

(RS)-1-[5-(4-Fluoro-phenyl)-2-methyl-thiazol-4-yl]-1-[3-phenyl-oxazol-2-ylmethyl)-morpholin-4-yl]-methanone The title compound (0.131 g) was prepared from the compound of description 53 (0.2 g) according to the method of example 54.

Mass Spectrum (API$^+$): Found 464 (MH$^+$). $C_{25}H_{22}FN_3O_3S$ requires 463.

EXAMPLE 68

(RS)-1-[5-(4-Fluoro-phenyl)-2-methyl-thiazol-4-yl]-1-[3-(4-phenyl-1H-imidazol-2-ylmethyl)-morpholin-4yl]-methanone The title compound (0.09 g) was prepared from the compound of description 53 (0.20 g) according to the method of example 64.

Mass Spectrum (API$^+$): Found 463 (MH$^+$). $C_{25}H_{23}FN_4O_2S$ requires 462.

EXAMPLE 69

1-[5-(4-Fluoro-plenyl)-2-methyl-thiazol-4-yl]-1-{2-[5-(4-fluoro-phenyl)-oxazol-2-ylmethyl]-piperidin-1-yl}-methanone The title compound (0.11 g) was prepared from the amine of description 55 (0.08 g) and 2-methyl-5-(4-fluorophenyl)-thiazole-4-carboxylic acid (0.07 g) according to the method of description 20.

Mass Spectrum (API$^+$): Found 480 (MH$^+$). $C_{26}H_{23}F_2N_3O_2S$ requires 479.

The compounds of the examples of Table 4 were prepared by analogous procedures to those used to prepare the compound of example 69.

TABLE 4

Piperidine 2-(5-aryloxazoles)

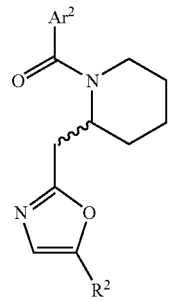

| Example | Amine | Ar$^2$ | R$^2$ | yield % | Mass Spectrum (Electrospray LC/MS) |
|---|---|---|---|---|---|
| 71 | D55 | naphthalen-1-yl | phenyl | 62 | Found 415 (MH$^+$). $C_{26}H_{23}FN_2O_2$ requires 414 |
| 72 | D55 | 3,5-dimethoxyphenyl | 4-fluorophenyl | 58 | Found 425 (MH$^+$). $C_{24}H_{25}FN_2O_4$ requires 424 |

TABLE 4-continued
Piperidine 2-(5-aryloxazoles)
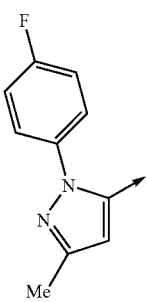
| Example | Amine | Ar² | R² | yield % | Mass Spectrum (Electrospray LC/MS) |
|---------|-------|-----|-----|---------|-------------------------------------|
| 73 | D55 | 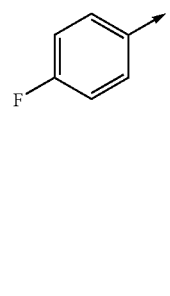 | 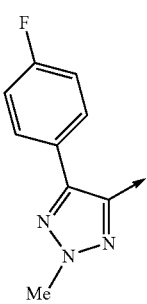 | 60 | Found 463 (MH⁺). $C_{26}H_{24}F_2N_4O_2$ requires 462 |
| 74 | D55 | 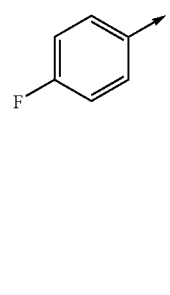 | 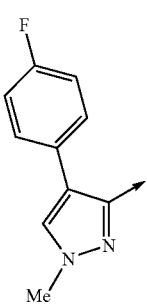 | 58 | Found 462 (MH⁺). $C_{25}H_{23}F_2N_5O_2$ requires 461 |
| 75 | D55 | 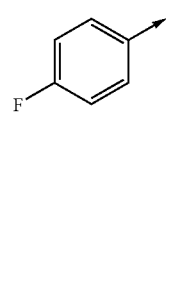 | | 63 | Found 463 (MH⁺). $C_{26}H_{24}F_2N_4O_2$ requires 462 |

TABLE 4-continued

Piperidine 2-(5-aryloxazoles)

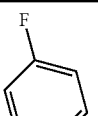

| Example | Amine | Ar² | R² | yield % | Mass Spectrum (Electrospray LC/MS) |
|---|---|---|---|---|---|
| 77 | D57 |  | 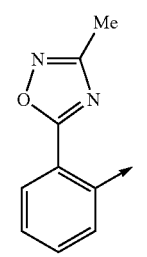 | 56 | Found 462 (MH⁺). $C_{26}H_{24}FN_3O_2S$ requires 461 |
| 78 | D57 |  | 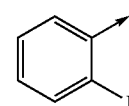 | 44 | Found 429 (MH⁺). $C_{25}H_{24}N_4O_3$ requires 428 |
| 79 | D57 |  | 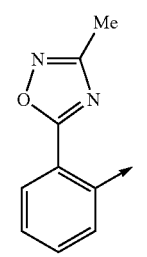 | 42 | Found 473 (MH⁺). $C_{22}H_{21}IN_2O_2$ requires 472 |

EXAMPLE 76

(RS)-1-{2-[5-(4-Fluoro-phenyl)-oxazol-2-ylmethyl]-piperidin-1-yl}-1-[5-(4-fluoro-phenyl)-thiazol-4-yl]-methanone The title compound was prepared from the compound of description 55 (0.07 g) and 5-(4-fluorophenyl)-thiazole-4-carboxylic acid chloride (0.06 g) according to the method of example 2.

Found 466 (MH⁺). $C_{25}H_{21}F_2N_3O_2S$ requires 465.

EXAMPLE 80

1-{(S)-2-[5-(4-Fluoro-phenyl)-1H-imidazol-2-ylmethyl]-pyrrolidin-1-yl}-1-[5-(4-fluoro-phenyl)-2-methyl-thiazol-4-yl]-methanone The title compound (0.09 g)-was prepared from the amine of description 60 (0.092 g) (0.08 g) and 2-methyl-5-(4-fluorophenyl)-thiazole-4-carboxylic acid (0.07 g) according to the method of description 20.

Mass Spectrum (API⁺): Found 465 (MH⁺). $C_{25}H_{22}F_2N_4OS$ requires 464.

The compounds of the examples of Table 5 were prepared by analogous procedures to those used to prepare the compound of example 80.

TABLE 5
Piperidine and pyrrolidine 2-(4-arylimidazoles)
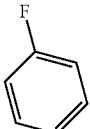
| Example | Amine | n | Ar² | R² | yield % | Mass Spectrum (Electrospray LC/MS) API⁺ |
|---|---|---|---|---|---|---|
| 81 (S)* | 60 | bond | 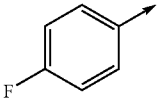 | 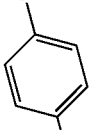 | 72 | Found 448 (MH⁺). $C_{25}H_{23}F_2N_5OS$ requires 447 |
| 82 (S)* | 60 | bond | 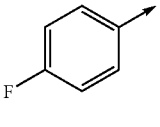 | 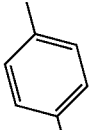 | 75 | Found 434 (MH⁺). $C_{24}H_{21}F_2N_5OS$ requires 433 |
| 83 | 63 | 1 | 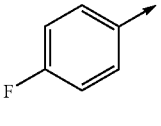 | 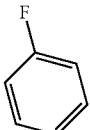 | 42 | Found 479 (MH⁺). $C_{26}H_{24}F_2N_4OS$ requires 478 |
| 84 | 63 | 1 | 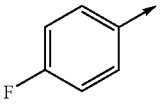 | | 59 | Found 462 (MH⁺). $C_{26}H_{25}F_2N_5O$ requires 461 |

TABLE 5-continued
Piperidine and pyrrolidine 2-(4-arylimidazoles)
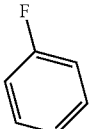
| Example | Amine | n | Ar² | R² | yield % | Mass Spectrum (Electrospray LC/MS) API⁺ |
|---|---|---|---|---|---|---|
| 85 | 63 | 1 | 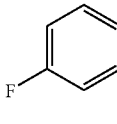 | 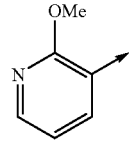 | 45 | Found 448 (MH⁺). $C_{25}H_{23}F_2N_5O$ requires 447 |
| 86 | 63 | 1 | 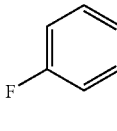 | 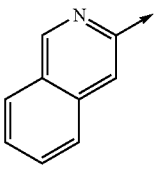 | 72 | Found 395 (MH⁺). $C_{22}H_{23}FN_4O_2$ requires 394 |
| 87 | 63 | 1 | 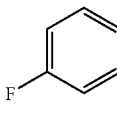 | 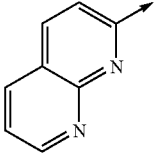 | 28 | Found 415 (MH⁺). $C_{25}H_{23}FN_4O$ requires 414 |
| 88 | 63 | 1 | 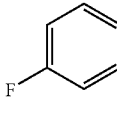 | 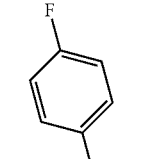 | 24 | Found 416 (MH⁺). $C_{24}H_{22}FN_5O$ requires 415 |
| 89 | 63 | 1 | 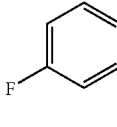 | | | Found 519 (MH⁺). $C_{29}H_{32}F_2N_6O$ requires 518 |

TABLE 5-continued
Piperidine and pyrrolidine 2-(4-arylimidazoles)
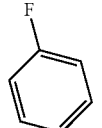
| Example | Amine | n | Ar² | R² | yield % | Mass Spectrum (Electrospray LC/MS) API⁺ |
|---------|-------|---|-----|----|---------|------------------------------------------|
| 90 | 63 | 1 | 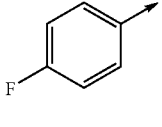 | 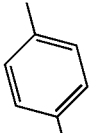 | | Found 495 (MH⁺). $C_{26}H_{24}F_2N_4O_2S$ requires 494 |
| 91 | 63 | 1 | 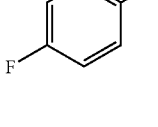 | 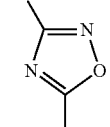 | | Found 463 (MH⁺). $C_{25}H_{24}F_2N_6O$ requires 462 |
| 92 | 63 | 1 | 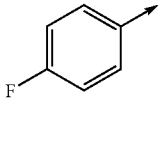 | 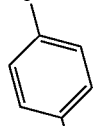 | | Found 446 (MH⁺). $C_{25}H_{24}FN_5O_2$ requires 445 |
| 104 | 74 | 1 | 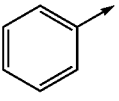 | | 18 | Found 477 (MH⁺). $C_{26}H_{25}FN_4O_2S$ requires 476 |

TABLE 5-continued
Piperidine and pyrrolidine 2-(4-arylimidazoles)
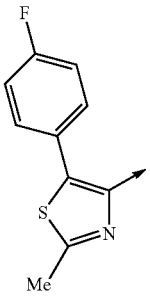
| Example | Amine | n | Ar² | R² | yield % | Mass Spectrum (Electrospray LC/MS) API⁺ |
|---|---|---|---|---|---|---|
| 108 | 84 | 1 | 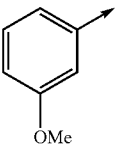 | 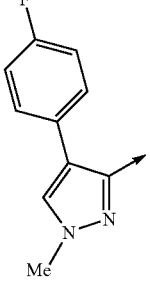 | 53 | Found 491 (MH⁺). $C_{27}H_{27}FN_4O_2S$ requires 490. Isolated as the HCl salt |
| 109 | 84 | 1 | 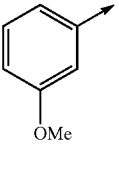 | 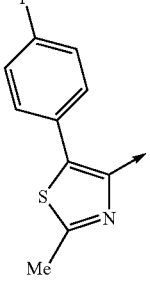 | 35 | Found 474 (MH⁺). $C_{27}H_{28}FN_5O_2$ requires 473 Isolated as the HCl salt |
| 110 | 87 | 1 | 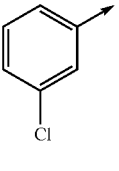 | 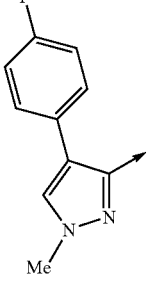 | 60 | Found 496(MH⁺). $C_{26}H_{24}{}^{37}ClFN_4OS$ requires 495 Isolated as the HCl salt |
| 111 | 87 | 1 | 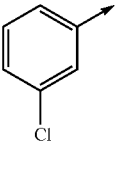 | | 55 | Found 480 (MH⁺). $C_{26}H_{25}{}^{37}ClFN_5O$ requires 479 Isolated as the HCl salt |

TABLE 5-continued
Piperidine and pyrrolidine 2-(4-arylimidazoles)
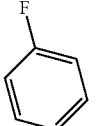
| Example | Amine | n | Ar² | R² | yield % | Mass Spectrum (Electrospray LC/MS) API⁺ |
|---------|-------|---|-----|-----|---------|------------------------------------------|
| 112 | 90 | 1 | 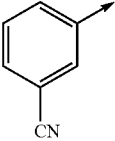 | 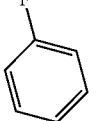 | 25 | Found 486 (MH⁺). $C_{27}H_{24}FN_5OS$ requires 485 Isolated as the HCl salt |
| 113 | 90 | 1 | 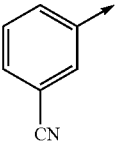 | 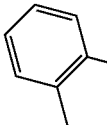 | 25 | Found 469 (MH⁺). $C_{27}H_{25}FN_6O$ requires 468 Isolated as the HCl salt |
| 114 | 74 | 1 | 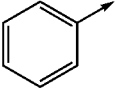 | 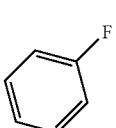 | | Mass Spectrum Found 461 (MH⁺). $C_{26}H_{25}FN_4OS$ requires 460. |
| 115 | 74 | 1 | 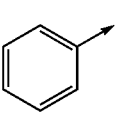 | | | Mass Spectrum Found 461 (MH⁺). $C_{26}H_{25}FN_4OS$ requires 460. |

TABLE 5-continued

Piperidine and pyrrolidine 2-(4-arylimidazoles)

| Example | Amine | n | Ar² | R² | yield % | Mass Spectrum (Electrospray LC/MS) API⁺ |
|---|---|---|---|---|---|---|
| 116 | 74 | 1 | 5-phenyl-2-methylthiazol-4-yl | phenyl | | Mass Spectrum Found 433 (MH⁺). $C_{26}H_{26}N_4OS$ requires 432. |
| 117 | 74 | 1 | 5-[3-(3-dimethylaminopropoxy)phenyl]-2-methylthiazol-4-yl | phenyl | | Mass Spectrum Found 544 (MH⁺). $C_{31}H_{37}N_5O_2S$ requires 543. |
| 118 | 74 | 1 | 5-[3-(4-dimethylaminobutoxy)phenyl]-2-methylthiazol-4-yl | phenyl | | Mass Spectrum Found 558 (MH⁺). $C_{32}H_{39}N_5O_2S$ requires 557. |
| 119 | 74 | 1 | 5-[3-(2-dimethylaminoethoxy)phenyl]-2-methylthiazol-4-yl | phenyl | | Mass Spectrum Found 530 (MH⁺). $C_{30}H_{35}N_5O_2S$ requires 529. |

TABLE 5-continued

Piperidine and pyrrolidine 2-(4-arylimidazoles)

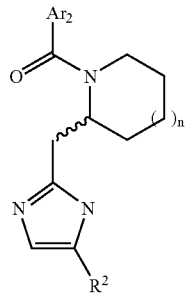

| Example | Amine | n | Ar² | R² | yield % | Mass Spectrum (Electrospray LC/MS) API⁺ |
|---------|-------|---|-----|----|---------|------------------------------------------|
| 159 | 106 | 1 | 5-(4-fluorophenyl)-2-methyl-thiazol-4-yl | 3,4-difluorophenyl | 34% | Mass Spectrum Found 497 (MH⁺). $C_{26}H_{23}F_3N_4OS$ requires 496. |
| 160 | 107 | 1 | 5-(4-fluorophenyl)-2-methyl-thiazol-4-yl | 3-fluorophenyl | 34% | Mass Spectrum Found 479 (MH⁺). $C_{26}H_{24}F_2N_4OS$ requires 478. |

(S)* against the Example number indicates that the Example was prepared as the (S) enantiomer.

EXAMPLE 93

(RS)-1-[5-(4Fluoro-phenyl)-2-methyl-thiazol-4-yl]-1-{2-[5-(2-methoxyphenyl)-1H-imidazol-2-ylm-ethyl]-piperidin-1-yl}-methanone The title compound (0.17 g) was prepared from the compound of description 37 (0.50 g) according to the method of description 59.

Found 491 (MH⁺). $C_{27}H_{27}FN_4O_2S$ requires 490.

EXAMPLE 94

(RS)-1-[5-(4-Fluoro-phenyl)-2-methyl-thiazol-4-yl]-1-{2-[5-(2-fluorophenyl)-1H-imidazol-2-ylmethyl]-piperidin-1-yl}-methanone The title compound (0.035 g) was prepared from the compound of description 39 (0.21 g) according to the method of description 59.

Found 479 (MH⁺). $C_{26}H_{24}F_2N_4OS$ requires 478.

EXAMPLE 95

(RS)-1-[5-(4-Fluoro-phenyl)-2-methyl-thiazol-4-yl]-1-{2-[5-(2-bromophenyl)-1H-imidazol-2-ylmethyl]-piperidin-1-yl}-methanone The title compound (0.18 g) was prepared from the compound of description 64 (0.50 g) according to the method of description 59.

Found 539, 541 (MH⁺) $C_{26}H_{24}BrFN_4OS$ requires 538, 540

EXAMPLE 96

(RS)-2-[2-(1-{1-[5-(4-Fluoro-phenyl)-2-methyl-thiazol-4-yl]-methanoyl}-piperidin-2-ylmethyl)-3H-imidazol-4-yl]-benzonitrile The compound of example 95 (0.11 g) and copper(I) cyanide (0.03 g) were combined in N-methylpyrrolidinone (5 ml) and the mixture boiled for 6 h. After cooling to room temperature the reaction mixture was stood overnight, diluted with ethyl acetate, passed through silica gel eluting with ethyl acetate/water. The organic phase was separated washed with water dried (MgSO$_4$) and solvent removed at reduced pressure. The residue was column chromatographed (silica gel, 20→100% ethyl acetate/pentane), the appropriate fractions combined and solvent removed at reduced pressure to give the title compound (0.03 g) as a gum Found 485 (MH$^+$) C$_{27}$H$_{24}$FN$_5$OS requires 486.

EXAMPLE 97

(RS)-1-{2-[4-Bromo-5(4-fluoro-phenyl)-1H-imidazol-2-ylmethyl]-piperidin-1-yl}-1-[5-(4-fluoro-phenyl)-2-methyl-thiazol4-yl]-methanone The title compound (0.17 g) was prepared by treating the compound of description 68 (0.27 g), 5-(4-fluoro-phenyl)-2-methyl-thiazole-4-carboxylic acid (0.19 g), 1-hydroxybenzotriazole (0.05 g) and diisopropylethylamine ((0.35 ml) in dimethylformamide (5 ml) with EDC.HCl. The mixture was stirred for 20 h, diluted with diethyl ether and washed with sodium carbonate and water (×3), dried (MgSO$_4$) and solvent removed at reduced pressure. The residue was column chromatographed (silica gel, 0→2% methanol/dichloromethane), the appropriate fractions combined and solvent removed at reduced pressure to give the title compound (0.17 g) as a gum Found 557, 559 (MH$^+$) C$_{26}$H$_{23}$BrF$_2$N$_4$OS requires 556, 558.

EXAMPLE 98

(RS)-5-(4-Fluoro-phenyl)-2-(1-{1-[5-(4-fluoro-phenyl)-2-methyl-thiazol-4-yl]-methanoyl}-piperidin-2-ylmethyl)-3H-imidazol-4-carbonitrile The title compound (0.038 g) was prepared from the compound of example 97 (0.22 g) according to the method of example 96.

Found 504 (MH$^+$) C$_{27}$H$_{23}$F$_2$N$_5$OS requires 503.

EXAMPLE 102

(RS)-1-(2-Ethoxy-phenyl)-1-[2-(4-phenyl-oxazol-2-ylmethyl)-piperidin-1-yl]-methanone The title compound (0.065 g) was prepared from the compound of description 77 (0.060 g) and 2-ethoxybenzoic acid (0.042 g) according to the method of example 1

Found 391 (MH$^+$) C$_{24}$H$_{26}$N$_2$O$_3$ requires 390.

EXAMPLE 103

(RS)-1-[5-(4-Fluoro-phenyl)-2-hydroxymethyl-thiazol-4-yl]-1-[2-(4-phenyl-oxazol-2-ylmethyl)-piperidin-1-yl]-methanone The title compound (0.055 g) was prepared from the compound of description 77 (0.15 g) and 5-(4-fluoro-phenyl)-2-hydroxymethyl-thiazole4-carboxylic acid (0.042 g) according to the method of example 97

Found 478 (MH$^+$) C$_{26}$H$_{24}$FN$_3$O$_3$S requires 477.

EXAMPLE 105

(RS)-1-[5-(4-Fluoro-phenyl)-2-methyl-thiazol-4-yl]-1-{2-[5-(4-fluoro-phenyl)-4H-[1,2,4]triazol-3-ylmethyl]-piperidin-1-yl}-methanone A solution of the compound of description 78 (0.20 g) and 4-fluorobenzamidine (0.11 g) in ethanol (5 ml) was treated with a 25% sodium methoxide in methanol solution (0.24 ml) and the mixture refluxed for 60 h. Solvent was removed at reduced pressure, the residue partitioned between dichloromethane/water, the organic phase separaeted, dried (MgSO$_4$) and solvent removed at reduced pressure to give the title compound (0.04 g)

Found 480 (MH$^+$) C$_{25}$H$_{23}$F$_2$N$_5$OS requires 479.

EXAMPLE 106

(RS)-1-{2-[5(4-Fluoro-phenyl)-4H-[1,2,4]triazol-3-ylmethyl]-piperidin-1-yl}-1-isoquinolin-3-yl-methanone The title compound (0.006 g) was prepared from the compound of description 81 (0.08 g) and isoquinoline-3-carboxylic acid (0.06 g) according to the method of description 20.

Found 416 (MH$^+$) C$_{24}$H$_{22}$FN$_5$O requires 415.

EXAMPLE 107

(RS)-1-{2-[3(3-Dimethylamino-propoxy)-phenyl]-thiophen-3-yl}-1-{2-[4-(4-fluoro-phenyl)-1H-imidazol-2-ylmethyl]-piperidin-1-yl}-methanone The title compound (0.006 g) was prepared from the compound of description 63 (0.071 g) and 2-[3-(3-Dimethylamino-propoxy)-phenyl]-thiophene-3-carbonyl chloride Found 547 (MH$^+$) C$_{31}$H$_{35}$FN$_4$O$_2$S requires 546.

EXAMPLE 120

(RS)-1-[5-(4-Fluoro-phenyl)-2-methyl-thiazol-4-yl]-1-{2-[5-(4-fluoro-phenyl)-tetrazol-2-ylmethyl]-piperidin-1-yl}-methanone The title compound (0.14 g) was prepared from the compound of description 92 (0.09 g) and 5-(4-fluoro-phenyl)-2-methyl-thiazole-4-carboxylic acid (0.08 g) according to the method of Description 20.

Found 481(MH$^+$) C$_{24}$H$_{22}$F$_2$N$_6$OS requires 480.

EXAMPLE 121

(RS)-1-{2-[5-(4-Fluoro-phenyl)-tetrazol-2-ylmethyl]-piperidin-1-yl}-1-[5-(4-fluoro-phenyl)-thiazol-4-yl]-methanone The title compound (0.13 g) was prepared from the compound of description 92 (0.09 g) and 5-(4-fluoro-phenyl)-thiazole-4-carboxylic acid (0.074 g) according to the method of Description 20.

Found 467(MH$^+$) C$_{23}$H$_{20}$F$_2$N$_6$OS requires 466.

EXAMPLE 122

(RS)-1-[4-(4-Fluoro-phenyl)-1H-pyrazol-3-yl]-1-{2-[5-(4-fluoro-phenyl)-tetrazol-2-ylmethyl]-piperidin-1-yl}-methanone The title compound (0.10 g) was prepared from the compound of description 92 (0.09 g) and 4-(4-Fluoro-phenyl)-1H-pyrazole-3-carboxylic acid (0.070 g) according to the method of Description 20.

Found 450 (MH$^+$) C$_{23}$H$_{21}$F$_2$N$_7$O requires 449.

EXAMPLE 123

(RS)-1-[4-(4-Fluoro-phenyl)-1-methyl-1H-pyrazol-3-yl]-1-{2-[5-(4-fluoro-phenyl)-tetrazol-2-ylmethyl]-piperidin-1-yl}-methanone The title compound (0.13 g) was prepared from the compound of description 92 (0.09 g) and 4-(4-Fluoro-phenyl-1-methyl-1H-pyrazole-3-carboxylic acid (0.070 g) according to the method of Description 20.
Found 464(MH$^+$) $C_{24}H_{23}F_2N_7O$ requires 463.

EXAMPLE 124

(RS)-1-[4-(4-Fluoro-phenyl)-2-methyl-2H-pyrazol-3-yl]-1-{2-[5-(4-fluoro-phenyl)-tetrazol-2-ylmethyl]-piperidin-1-yl}-methanone The title compound (0.03 g) was prepared from the compound of description 92 (0.09 g) and 4-(4-fluoro-phenyl)-2-methyl-2H-pyrazole-3-carboxylic acid (0.070 g) according to the method of Description 20.
Found 464 (MH$^+$) $C_{24}H_{23}F_2N_7O$ requires 463.

EXAMPLE 144

(RS)-1-[5-(4-Fluoro-phenyl)-2-methyl-thiazol-4-yl]-1-[2-(4-phenyl-imidazol-1-ylmethyl)-piperidin-1-yl]-methanone The title compound (0.065 g) was prepared from the compound of description 94 (0.07 g) and 5-(4-fluoro-phenyl)-2-methyl-thiazole-4-carboxylic acid (0.069 g) according to the method of Description 20.
Found 461 (MH$^+$) $C_{26}H_{25}FN_4OS$ requires 460.

EXAMPLE 145

(RS)-1-[5-(4-Fluoro-phenyl)-thiazol-4-yl]-1-[2-(4-phenyl-imidazol-1-ylmethyl)-piperidin-1-yl]-methanone The title compound (010 g) was prepared from the compound of description 94 (0.07 g) and 5-(4-Fluoro-phenyl)-thiazole-4-carboxylic acid (0.065 g) according to the method of Description 20.
Found 447(MH$^+$) $C_{25}H_{23}FN_4OS$ requires 446.

EXAMPLE 146

(RS)-1-[4-(4-Fluoro-phenyl)-1-methyl-1]-pyrazol-3-yl]-1-[2-(4-phenyl-imidazol -1-ylmethyl)-piperidin-1-yl]methanone The title compound (0.135 g) was prepared from the compound of description 94 (0.07 g) and 4-(4-fluoro-phenyl)-1-methyl-1H-pyrazole-3-carboxylic acid (0.064 g) according to the method of Description 20.
Found 444 (MH$^+$) $C_{26}H_{26}FN_5O$ requires 443.

EXAMPLE 147

(RS)-1-[5-(4-Fluoro-phenyl-2-methyl-thiazol-4-yl]-1-{2-[3-(4-fluoro-phenyl) -pyrazol-1-ylmethyl]-piperidin-1-yl}-methanone The title compound (0.10 g) was prepared from the compound of description 96 (0.086 g) and 5-(4-fluoro-phenyl)-2-methyl-thiazole-4-carboxylic acid (0.075 g) according to the method of Description 20.
Found 479 (MH$^+$) $C_{26}H_{24}F_2N_4OS$ requires 478.

EXAMPLE 148

(RS)-1-(5-Bromo-2-methoxy-phenyl)-1-{2-[3-(4-fluoro-phenyl)-pyrazol-1-ylmethyl]-piperidin-1-yl}-methanone The title compound (0.125 g) was prepared from the compound of description 96 (0.086 g) and 5-bromo-2-methoxy-benzoic acid (0.08 g) according to the method of Description 20.

EXAMPLE 149

(RS)-1-[5-(4-Fluoro-phenyl)-2-methyl-2H-[1,2,3]triazol-4-yl]-1-{2-[3-(4-fluoro-phenyl)-pyrazol-1-ylmethyl]-piperidin-1-yl}-methanone The title compound (0.09 g) was prepared from the compound of description 96 (0.086 g) and 5-(4-fluoro-phenyl)-2-methyl-2H-[1,2,3]triazole-4-carboxylic acid (0.078 g) according to the method of Description 20.
Found (MH$^+$) 463 $C_{25}H_{24}F_2N_6O$ requires 462.

EXAMPLE 150

(RS)-1-[5-(4-Fluoro-phenyl)-2-methyl-oxazol-4-yl]-1-{2-[3-(4-fluoro-phenyl)-pyrazol-1-ylmethyl]-piperidin-1-yl}-methanone The title compound (0.11 g) was prepared from the compound of description 96 (0.086 g) and 5-(4-fluoro-phenyl)-2-methyl-oxazole-4-carboxylic acid (0.078 g) according to the method of Description 20.
Found 463 (MH$^+$) $C_{26}H_{24}F_2N_4O_2$ requires 462.

EXAMPLE 151

1-{2-[3-(4-Fluoro-phenyl)-pyrazol-1-ylmethyl]-piperidin-1-yl}-1-[2-(3-methyl-[1,2,4]oxadiazol-5-yl)-phenyl]-methanone The title compound (0.05 g) was prepared from the compound of description 96 (0.086 g) and 2-(3-Methyl-[1,2,4]oxadiazol-5-yl)-benzoic acid (0.070 g) according to the method of Description 20.
Found 446 (MH$^+$) $C_{25}H_{24}FN_5O_2$ requires 445.

EXAMPLE 152

(RS)-1-[5-(4-luoro-phenyl)-2-methyl-thiazol-4-yl]-1-[2-(4-phenyl-thiazol-2-ylmethyl)-piperidin-1-yl]-methanone The title compound (0.133 g) was prepared from the compound of description 99 (0.184 g) according to the method of description 20.
Found 478 (MH$^+$) $C_{26}H_{24}FN_3OS_2$ requires 477.

EXAMPLE 153

(R)-1-[5-(4-Fluoro-phenyl)-2-methyl-thiazol-4-yl]-1-[3-(4-phenyl-oxazol-2-ylmethyl)-morpholin-4-yl]-methanone and (S)-(R)-1-[5-(4-Fluoro-phenyl)-2-methyl-thiazol-4-yl]-1-[3-(4-phenyl-oxazol-2-ylmethyl)-morpholin-4-yl]-methanone The title compounds were isolated by chiral HPLC on a Chiralcel OD; 250 mm×19 mm i.d.; 10 micron particle size column, with a mobile phase of n-Hexane, Ethanol (80:20 v/v) with a flow rate of 17 ml/min-1, a runtime of 20 min with detection by UV absorbance at 215 nM. The racemic compound of example 67 was injected in ethanol (2 ml) at 4 mg/ml. The two enantiomers were isolated as the faster and slower running components with ee's of 99.4% and 96.6%.

Faster running component Mass Spectrum (API$^+$): Found 464 (MH$^+$). $C_{25}H_{22}FN_3O_3S$ requires 463.

Slower running component Mass Spectrum (API$^+$): Found 464 (MH$^+$). $C_{25}H_{22}FN_3O_3S$ requires 463.

EXAMPLE 154

(RS)-1-{2-[5-(2,5-Dimethyl-2H-pyrazol-3-yl)-[1,3,4]oxadiazol-2-ylmethyl]-piperidin-1-yl}-1-[5-(4-fluoro-phenyl)-2-methyl-thiazol-4 yl]-methanone The compound of description 101 (0.35 g) and polyphosphoric acid (0.70 g) were combined and warmed at 140° C. for 4 h. The reaction was cooled to room temperature, potassium carbonate and iced water added the basic solution was extracted with dichloromethane (×2), the combined organic phase washed with water, dried and solvent removed at reduced pressure. The residue was column chromatographed (silica gel; 20% ethyl acetate in pentane eluant) to give the title compound (0.073 g)

Mass Spectrum (API$^+$): Found 481 (MH$^+$). $C_{24}H_{25}FN_6O_2S$ requires 480.

EXAMPLE 155

(RS)-1-[2-(4,5-Dipheny)-1H-imidazol-2-ylmethyl)-piperidia-1-yl]-1-[5-(4-fluoro-phenyl)-2-methyl-thiazol-4-yl]-methanone The title compound (0.34 g) was prepared from the compound of description 102 (0.53 g) according to the method of example 64.

Mass Spectrum (API$^+$): Found 537 (MH$^+$). $C_{32}H_{29}FN_4OS$ requires 536.

EXAMPLE 156

(RS)-1-{2-[4(4-Fluoro-phenyl)-1-methyl-1H-imidazol-2-ylmethyl]-piperidin-1-yl}-1-[5-(4 fluoro-phenyl)-2-methyl-thiazol-4-yl]-methanone The compound of example 83 (0.25 g) was added to sodium hydride (60% in oil, 0.042 g) in dimethylformaide (5 ml) and stirred until gas evolution had ceased. Iodomethane 0.163 g) was added, stirring continued for 16 h, diluted carefully with water and extracted with ethyl acetate (×4). The combined organic phase was washed with water and brine, dried (MgSO$_4$) and solvent removed at reduced pressure. The residue was column chromatographed (silica gel, 50% ethyl acetate:pentane eluant) to give after combining appropriate fractions the title compound (0.06 g).

Mass Spectrum (API$^+$): Found 493 (MH$^+$). $C_{27}H_{26}F_2N_4OS$ requires 492.

EXAMPLE 157

(RS)-1-[2-(5-Benzofuran-2-yl-[1,3,4]oxadiazol-2-ylmethyl)-piperidin-1-yl]-1-[5-(3-fluoro-phenyl)-2-methyl-thiazol-4-yl]-methanone The title compound (0.038 g) was prepared from the compound of description 104 and 5-(3-Fluoro-phenyl)-2-methyl-thiazole-4-carboxylic acid (0.068 g) according to the method of description 20.

Mass Spectrum (API$^+$): Found 503 (MH$^+$). $C_{27}H_{23}FN_4O_3S$ requires 502.

EXAMPLE 158

(RS)-1-[5-(4-Fluoro-phenyl)-2-methyl-thiazol-4-yl]-1-[2-(4-pyridin-2-yl-oxazol-2-ylmethyl)-piperidin-1-yl]-methanone The compound of description 105 (0.56 g) and 2-bromo-1-pyridin-2-yl-ethanone (0.44 g) were combined in dichloromethane (2 ml). The mixture was heated to 100° C. until the dichloromethane had evaporated and then heating continued at 140° C. for 6 h. The reaction was cooled to room temperature, and the residue dissolved in sodium hydroxide/dichloromethane, the organic phase separated, dried, solvent removed at reduced pressure and the residue column chromatographed (silica gel; 0→8% methanol/dichloromethane) to give after combining the appropriate fractions the title compound (0.05 g)

Mass Spectrum (API$^+$): Found 463 (MH$^+$). $C_{25}H_{23}FN_4O_2S$ requires 462.

EXAMPLE 161

(RS)-1-[5-(4-Fluorophenyl)-2-methylthiazol-4-yl]-1-{2-[5-(4-fluorophenyl)-1H-pyrazol-3-ylmethyl]-piperidin-1-yl}-methanone The compound of description 108 (0.430 g) was dissolved in ethanol (20 ml) and stirred at room temperature for 16 hours with hydrazine hydrate (0.087 ml). The solution was then evaporated at reduced pressure and chromatographed over silica gel, eluting with a gradient of 0 to 10% [9:1 methanol/conc. ammonia solution] in dichloromethane. The title compound was obtained as a white foam (0.034 g), mass spectrum (API$^+$) 479 [MH$^+$], (API$^-$) 477 [(M-H)$^-$] $C_{26}H_{24}F_2N_4OS$ requires 478

EXAMPLE 162

(RS)-1-{2-[4(4-Fluorophenyl)-1H-imidazol-2-ylmethyl]-piperazin-1-yl}-[5-(4-fluorophenyl)-2-methylthiazol-4-yl]-methanone 3-[4-4-Fluorophenyl)-1H-imidazol-2-ylmethyl]-4-{-[5-(4-fluorophenyl)-2-methylthiazol-4-yl]-methanoyl}-piperazine-1-carboxylic acid tert-butyl ester description 112 (0.130 g) was dissolved in TFA and stirred under argon at room temperature for 3 hours. The TFA was evaporated and the residue chromatographed over silica gel, eluting with a gradient of 0 to 10% [9:1 methanol/conc. ammonia solution] in dichloromethane. The title compound was obtained as a white foam (0.095 g), mass spectrum (API$^+$) 480 [MH$^+$], $C_{25}H_{23}F_2N_5OS$ requires 479.

EXAMPLE 163

1-[5-(4-Fluorophenyl)-2-methyl-thiazol-4-yl]-1-{2-[4-(4-fluorophenyl)-oxazol-2-ylmethyl]-piperazin-1-yl}-methanone 4-{1-[5-(4-Fluorophenyl)-2-methyl-tliiazol-4-yl]-methanoyl}-3-[4-(4-fluoro-pbenyl)-oxazol-2-ylmethyl]-piperazine-1-carboxylic acid tert-butyl ester (0.130 g) was dissolved in trifluoroacetic acid (10 ml) and stirred at rdom temperature for 2 hours. The reaction mixture was then evaporated to dryness at reduced pressure and the residue was chromatographed over silica gel. Elution with a gradient of 0 to 10% [9:1 methanol/conc. ammonia solution] in dichloromethane provided the title compound as a pale yellow gum (0.013 g), mass spectrum (API$^+$) 481 [MH$^+$], $C_{25}H_{22}F_2N_4O_2S$ requires 480.

EXAMPLE 164

(RS)-1-[3-(5-bromo-4-phenyl-oxazol-2-ylmethyl)-morpholin-4-yl]-1-[5-(4-fluoro-phenyl)-2-methyl-thiazol-4-yl]-methanone The compound of example 67 (0.152 g) was dissolved in carbon tetrachloride (10 ml) and was then treated with N-bromosuccinimide (0.058 g) and stirred under argon at room temperature for 24 h. A further quantity of N-bromosuccinimide (0.006 g) was added and the mixture stirred for a further 1 h. The mixture was filtered through a cotton wool plug and the filtrate was evaporated to dryness under reduced pressure. The residue was column chromatographed (silica gel, 0→40% ethyl acetate-pentane) to give the title compound (0.117 g).
Mass Spectrum (API$^+$ LC/MS): Found 542, 544. $C_{25}H_{21}BrFN_3O_3S$ requires 541,543.

EXAMPLE 165

(RS)-1-[2-(5-Chloro-4-phenyl-oxazol-2-ylmiethyl) piperidin-1-yl]-1-[5-(4-fluoro-phenyl)-2-methyl-thiazol-4-yl]-methanone The oxazole of example 70 (0.06 g) in carbon tetrachloride (10 ml) was treated with N-chlorosuccinimide (0.018 g) and stirred at room temperature, under argon, for 6 h. A further quantity of N-chlorosuccinimide (0.009 g) was added and the mixture heated at 80° C., under argon for 16 h. The solvent was removed under reduced pressure. The residue was partitioned between ethyl acetate and water. The organic layer was dried (magnesium sulfate) and the solvent removed under reduced pressure. The residue was column chromatographed (silica gel; 0→40% ethyl acetate-pentane) to afford the title compound (0.024 g).
Mass Spectrum (Electrospray LC/MS); 496,498 (MH$^+$). $C_{26}H_{23}ClFN_3O_2S$ requires 495,497.

EXAMPLE 166

1-[5-(4-Fluoro-phenyl)-2-methyl-thiazol-4-yl]-1-[(S)-2-(5-phenyl-4H-[1,2,4]triazol-3-ylmethyl)-pyrrolidin-1-yl]-methanone The title compound (0.077 g) was prepared from the amine of description 117 (0.072 g) and 5-(4-fluoro-phenyl)-2-methyl-thiazole-4-carboxylic acid (0.075 g) according to the method of example 1.

Mass Spectrum (API$^+$ LC/MS): 448 (MH$^+$). $C_{24}H_{22}FN_5OS$ requires 447.

EXAMPLE 167

(RS)-1-[2-(5-Bromo-4-phenyl-oxazol-2-ylmethyl)-piperidin-1-yl]-1-[5-(4-fluoro-phenyl)-2-methyl-thiazol-4-yl]-methanone The title compound (0.412 g) was prepared by treating the compound of example 70 with N-bromosuccinimide (0.190 g) according to the method of example 164.
Mass Spectrum (Electrospray LC/MS): 540, 542 (MH$^+$). $C_{26}H_{23}BrFN_3O_2S$ requires 539, 541.

EXAMPLE 168

(RS)-1-(2-Methyl-5-phenyl-thiazol-4-yl)-1-[2-(4-phenyl-oxazol-2-ylmethyl)-piperidin-1-yl]-methanone The title compound (0.165 g) was prepared from the amine of description 77 (0.116 g) and 2-Methyl-5-phenyl-thiazole-4-carboxylic acid (0.105 g) according to the method of example 1.
Mass Spectrum (Electrospray LC/MS): 444 (MH$^+$). $C_{26}H_{25}N_3O_2S$ requires 443.

EXAMPLE 169

(RS)-1-[1-(2-Dimethylamino-ethyl)-4(4 fluoro-phenyl)-1H-pyrazol-3-yl]-1-[2(4-phenyl-oxazol-2-ylmethyl)-piperidin-1-yl]-methanone The title compound (0.169 g) was prepared from the amine of description 77 (0.116 g) and 1-(2-Dimethylamino-ethyl)-4-(4-fluoro-phenyl)-1H-pyrazole-3-carboxylic acid (0.132 g) according to the method of example 1.
Mass Spectrum (Electrospray LC/MS): 502 (MH$^+$). $C_{29}H_{32}FN_5O_2$ requires 501.

EXAMPLE 170

(RS)-2-(1-{1-[5-(4-Fluoro-phenyl)-2-methyl-thiazol-4-yl]-methanoyl}-piperidin-2-ylmethyl)-4-phenyl-oxazole-5-carbonitrile The title compound (50 mg) was prepared by treating the compound of example 167 (0.410 g) with copper(I)cyanide (0.103 g) according to the method of example 96. Following column chromatography, further purification by HPLC was required (Supercosil ABZ+, 5-95% acetonitrile containing 0.1% trifluoroacetic acid-water containing 0.1% trifluoroacetic acid).
Mass Spectrum (Electrospray LC/MS): 487 (MH$^+$). $C_{27}H_{23}FN_4O_2S$ requires 486.

EXAMPLE 171

(RS)-1-[2-(5-Bromo-4-phenyl-oxazol-2-ylmethyl)-piperidin-1-yl]-1-(2-methyl-5-phenyl-thiazol-4-yl)-methanone The title compound (0.075 g) was prepared by treating the compound of example 168 (0.093 g) with N-bromosuccinimide (0.037 g) according to the method of example 164.

Mass Spectrum (Electrospray LC/MS): 522,524 (MH⁺). $C_{26}H_{24}BrFN_3O_2S$ requires 521,523.

EXAMPLE 172

1-[5-(4-Fluoro-phenyl)-2-methyl-thiazol-4-yl]-1-[(S)-2-(4-phenyl-oxazol-2-ylmethyl)-pyrrolidin-1-yl]-methanone The title compound (0.103 g) was prepared from the amine of description 120 (0.061 g) and 5-(4-fluoro-phenyl)-2-methyl-thiazole-4-carboxylic acid (0.064 g) according to the method of example 1.

Mass Spectrum (Electrospray LC/MS): 448 (MH⁺). $C_{25}H_{22}FN_3O_2S$ requires 447.

EXAMPLE 173

1-[(S)-2-(5-Bromo-4-phenyl-oxazol-2-ylmethyl)-pyrrolidin-1-yl]-1-[5-(4-fluoro-phenyl)-2-methyl-thiazol-4-yl]-methanone The title compound (0.066 g) was prepared by treating the compound of example 172 (0.075 g) with N-bromosuccinimide (0.030 g) according to the method of example 164.

Mass Spectrum (Electrospray LC/MS): 526,528 (MH⁺). $C_{25}H_{21}BrFN_3O_2S$ requires 525,527.

EXAMPLE 174

(RS)-1-[5-(4-Chloro-phenyl)-2-methyl-thiazol-4-yl]-[2-(4-pbenyl-oxazol-2-ylmethyl)-piperidin-1-yl]-methanone The title compound (0.106 g) was prepared from the amine of description 77 (0.072 g) and 5-(4-chloro-phenyl)-2-methyl-thiazole-4-carboxylic acid (0.076 g) according to the method of example 1.

Mass Spectrum (API⁺ LC/MS): 478,480 (MH⁺). $C_{26}H_{24}ClN_3O_2S$ requires 477, 479.

EXAMPLE 175

(RS)-1-[4-(4-Fluoro-phenyl)-1-methyl-1H-pyrazol-3-yl]-1-[2-(4-phenyl-thiazol-2-ylmethyl)-piperidin-1-yl]-methanone The title compound (0.022 g) was prepared from the compound of description 99 (0.060 g) and 4-(4-Fluoro-phenyl)-1-methyl-1H-pyrazole-3-carboxylic acid (0.044 g) according to the method of example 1.

Mass Spectrum (Electrospray LC/MS): Found 461 (MH⁺). $C_{26}H_{25}FN_4OS$ requires 460.

EXAMPLE 176

(RS)-1-{2-[4(2-Bromo-phenyl)-oxazol-2-ylmethyl]-piperidin-1-yl}-1-[5-(4-fluoro-phenyl)-2-methyl-thiazol-4yl]-methanone The title compound (0.50 g) was prepared from the compound of description 121 (2.00 g), acetamide (1.05 g) and boron trifluoride.diethyl etherate (0.7 ml) in xylene according to the method of example 54.

Mass Spectrum (Electrospray LC/MS): Found 540,542 (MH⁺). $C_{26}H_{23}BrFN_3O_2S$ requires 539,541.

EXAMPLE 177

(RS)-2-[2-(1-{1-[5-(4-Fluoro-phenyl)-2-methyl-thiazol-4-yl]-methanoyl}-piperidin-2-ylmethyl)-oxazol-4-yl]-benzonitrile A mixture of the bromide (0.240 g) of example 176, Cu(I)CN (0.060 g) and N-Methyl pyrrolidinone (5 ml) was heated at 180° C. for 16 h. The cooled reaction mixture was diluted with ethyl acetate and passed through kiesselguhr, washing with ethyl acetate. The filtrate was washed with water, dried (sodium sulfate) and solvent removed at reduced pressure. The residue was column chromatographed (silica gel, 20-50% ethyl acetate-pentane) to give the title compound as a pale yellow gum (0.101 g Mass Spectrum (API⁺ LC/MS): Found 487 (MH⁺). $C_{27}H_{23}FN_4O_2S$ requires 486.

EXAMPLE 178

(RS)-1-[5-(4-Fluoro-phenyl)-2-methyl-thiazol-4-yl]-1-{2-[4-(2-fluoro-phenyl)-thiazol-2-ylmethyl]-piperidin-1-yl}-methanone The title compound (0.235 g) was prepared as a solid from the amine of description 122 (0.330 g) and 2-methyl-5-(4-fluoro-phenyl)-thiazole-4-carboxylic acid (0.283 g) according to the method of example 1.

Mass Spectrum (Electrospray LC/MS): Found 496 (MH⁺). $C_{26}H_{23}F_2N_3OS_2$ requires 495.

EXAMPLE 179

(RS)-1-[5-(4-Fluoro-phenyl)-2-methyl-thiazol-4-yl]-1-{2-[4-(3-fluoro-phenyl)-thiazol-2-ylmethyl]-pipendin-1-yl}-methanone The title compound (0.047 g) was prepared as a solid from the amine of description 123 (0.100 g) and 2-methyl-5-(4-fluoro-phenyl)-thiazole-4-carboxylic acid (0.086 g) according to the method of example 1.

Mass Spectrum (Electrospray LC/MS): Found 496 (MH⁺). $C_{26}H_{23}F_2N_3OS_2$ requires 495.

EXAMPLE 180

(RS)-1-{2-[4-(3-Fluoro-phenyl)-thiazol-2-ylmethyl]-piperidin-1-yl}-1-(2-methyl-5-phenyl-thiazol-4-yl)-methanone The title compound (0.031 g) was prepared as a solid from the amine of description 123 (0.100 g) and 2-methyl-5-phenyl-thiazole-4-carboxylic acid (0.079 g) according to the method of example 1.

Mass Spectrum (Electrospray LC/MS): Found 478 (MH⁺). $C_{26}H_{24}FN_3OS_2$ requires 477.

It is understood that the present invention covers all combinations of particular and preferred groups described herein above.

Determination of Orexin-1 Receptor Antagonist Activity

The orexin-1 receptor antagonist activity of the compounds of formula (I) was determined in accordance with the following experimental method.

Experimental Method

CHO-DG44 cells expressing the human orexin-1 receptor were grown in cell medium (MEM medium with Earl's salts) containing 2 mM L-Glutamine, 0.4 mg/mL G418 Sulphate from GIBCO⁻ BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 60 min at 37 C in 5% CO2. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37 C in 5% $CO_2$ for 30 minutes. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 seconds (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS*, 1995, 16, 413-417) to generate a concentration effect value. Antagonist Kb values were calculated using the equation:

$$Kb=IC50/(1+([3/EC50])$$

where EC50 was the potency of human orexin-A determined in the assay (in nM terms) and IC50 is expressed in molar terms.

Compounds of Examples tested according to this method had pKb values in the range 6.7-9.5 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 60 min at 37 C in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37 C in 5% $CO_2$ for 30 minutes. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 seconds (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS*, 1995, 16, 413-417) to generate a concentration effect value. Antagonist Kb values were calculated using the equation:

$$Kb=IC50/(1+([3/EC50])$$

where EC50 was the potency of human orexin-A determined in the assay (in nM terms) and IC50 is expressed in molar terms.

Compounds of Examples tested according to this method had pKb values in the range <6.3-8.2 at the human cloned orexin-2 receptor.

The application or which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (I):

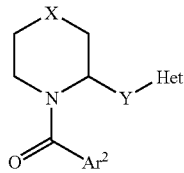

(I)

wherein:
X is (CH$_2$),
Y is CH$_2$, CHOH, or —CH$_2$CH(OH)—;
Het is an optionally substituted 1,3,4-oxadiazolyl substituted by R$^2$, wherein R$^2$ is an optionally substituted aryl;
Ar$^2$ is an optionally substituted thiazolyl, pyrazolyl, thienyl, benzofuranyl, or triazolyl, wherein said thiazolyl, pyrazolyl, thienyl, benzofuranyl, or triazolyl is substituted by R$^1$ and is further optionally substituted;
R$^1$ is hydrogen, an optionally substituted (C$_{1-4}$)alkoxy, halo, cyano, optionally substituted(C$_{1-6}$)alkyl, or optionally substituted phenyl;
wherein said optionally substituted oxadiazolyl, aryl, thiazolyl, pyrazolyl, thienyl, benzofuranyl, triazolyl, (C$_{1-4}$)alkoxy, (C$_{1-6}$)alkyl, or phenyl is optionally substituted by halogen, hydroxy, oxo, cyano, nitro, (C$_{1-4}$)alkyl, (C$_{1-4}$)alkoxy, hydroxy(C$_{1-4}$)alkyl, hydroxy(C$_{1-4}$)alkoxy, halo(C$_{1-4}$)alkyl, halo(C$_{1-4}$)alkoxy, aryl(C$_{1-4}$)alkoxy, (C$_{1-4}$)alkylthio, hydroxy(C$_{1-4}$)alkyl, (C$_{1-4}$)alkoxy(C$_{1-4}$)alkyl, (C$_{3-6}$)cycloalkyl(C$_{1-4}$)alkoxy, (C$_{1-4}$)alkanoyl, (C$_{1-4}$)alkoxycarbonyl, (C$_{1-4}$)alkylsulfonyl, (C$_{1-4}$)alkylsulfonyloxy, (C$_{1-4}$)alkylsulfonyl(C$_{1-4}$)alkyl, arylsulfonyl, arylsulfonyloxy, arylsulfonyl(C$_{1-4}$)alkyl, (C$_{1-4}$)alkylsulfonamido, (C$_{1-4}$)alkylamido, (C$_{1-4}$)alkylsulfonamido(C$_{1-4}$)alkyl, (C$_{1-4}$)alkylamido(C$_{14}$)alkyl, arylsulfonamido, arylcarboxamido, arylsulfonamido (C$_{1-4}$)alkyl, arylcarboxamido(C$_{1-4}$)alkyl, aroyl, aroyl (C$_{1-4}$)alkyl, aryl(C$_{1-4}$)alkanoyl, (C$_{1-4}$) acyl, aryl, aryl (C$_{1-4}$)alkyl, (C$_{1-4}$)alkylamino(C$_{1-4}$)alkyl, R$^a$R$^b$N—, R$^a$OCO(CH$_2$)$_r$, R$^a$CON(R$^a$)(CH$_2$)$_r$, R$^a$R$^b$NCO(CH$_2$)$_r$, R$^a$R$^b$NSO$_2$(CH$_2$)$_r$ or R$^a$SO$_2$NR$^b$(CH$_2$)$_r$, wherein r represents zero or an integer from 1 to 4, or R$^a$R$^b$N(CH$_2$)n- or R$^a$R$^b$N(CH$_2$)nO—, wherein n represents an integer from 1 to 4, wherein each of R$^a$ and R$^b$ independently represents a hydrogen atom or a (C$_{1-4}$)alkyl group;
or a pharmaceutically acceptable salt thereof.

2. A compound according to claim 1 wherein R$^1$ represents an optionally substituted phenyl group.

3. A compound according to claim 1 wherein Y is CH$_2$.

4. A compound according to claim 1 wherein optional substituents for said optionally substituted (C$_{1-4}$)alkoxy, (C$_{1-6}$)alkyl or phenyl of R$^1$ are halogen, (C$_{1-4}$)alkoxy(C$_{1-4}$) alkyl, R$^a$R$^b$N, R$^a$R$^b$N(CH$_2$)n, R$^a$R$^b$N(CH$_2$)nO, (C$_{1-4}$)alkoxy, (C$_{1-4}$)alkanoyl and (C$_{1-4}$)alkyl.

5. A compound of formula (I) according to claim 1 selected from:

(RS)-1-[5-(4-Fluoro-phenyl)-2-methyl-thiazol-4-yl]-1-[2-(5-phenyl-[1,3,4]oxadiazol-2-ylmethyl)-piperidin-1-yl]-methanone;

(RS)-1-[5-(4-Fluoro-phenyl)-2-methyl-2H-[1,2,3]triazol-4-yl]-1-[2-(5-phenyl-[1,3,4]oxadiazol-2-ylmethyl)-piperidin-1-yl]-methanone;

(RS)-1-{2-[5-(2,5-Dimethyl-2H-pyrazol-3-yl)-[1,3,4] oxadiazol-2-ylmethyl]-piperidin-1-yl}-1-[5-(4-fluoro-phenyl)-2-methyl-thiazol-4-yl]-methanone;

(RS)-1-[2-(5-Benzofuran-2-yl-[1,3,4]oxadiazol-2-ylmethyl)-piperidin-1-yl]-1-[5-(3-fluoro-phenyl)-2-methyl-thiazol-4-yl]-methanone;

and a pharmaceutically acceptable salt thereof.

6. A compound according to claim 1, having the formula:

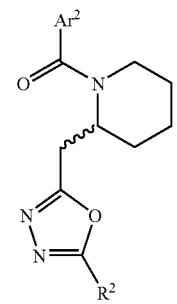

wherein Ar$^2$ and R$^2$ are selected from:

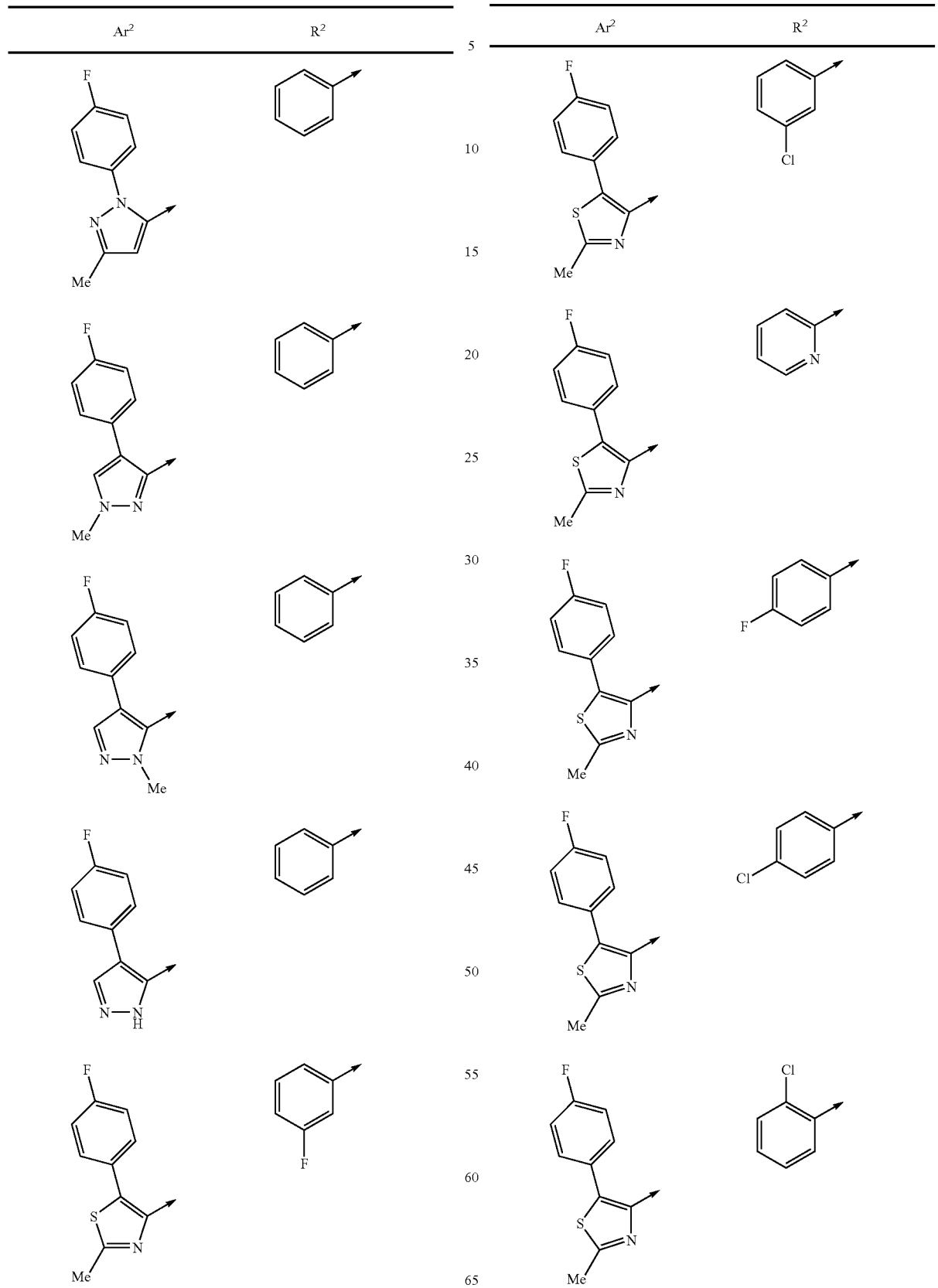

| Ar² | R² |
|---|---|
| 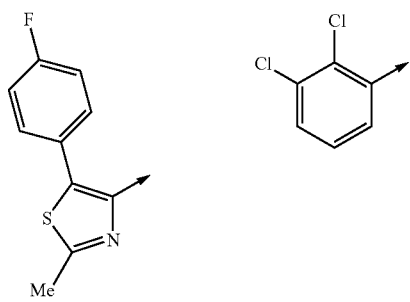 | 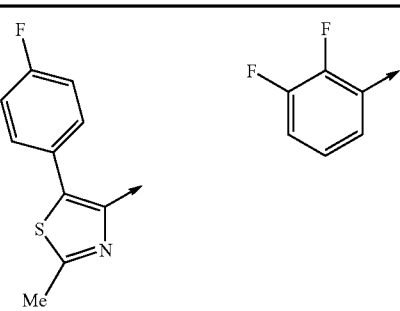 |
| 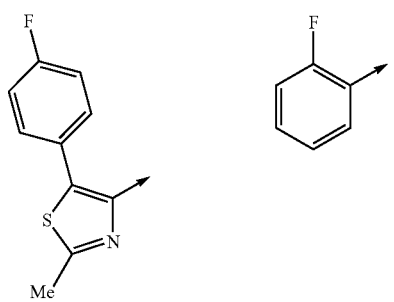 | 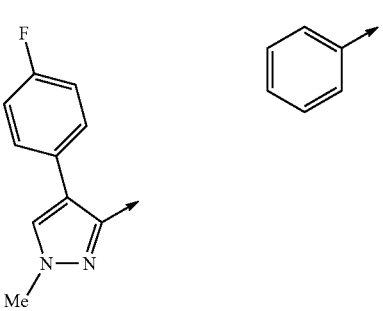 |
|  | 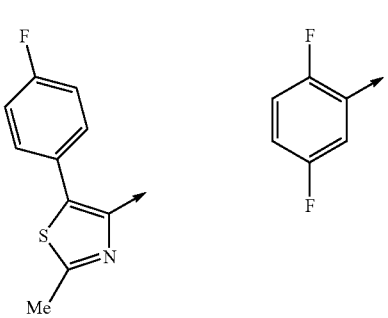 |
|  |  |
| 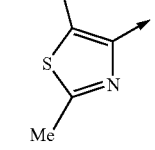 |  |
|  |  |
| 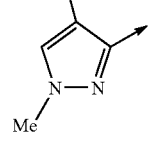 |  |
| 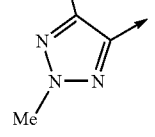 | |

-continued
| Ar² | R² |
|---|---|
| 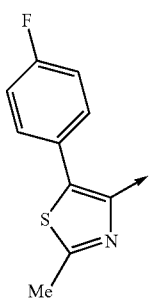 | 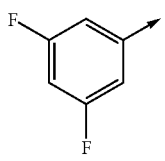 |
| 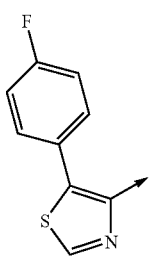 | 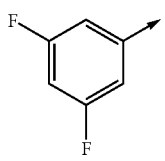 |
| 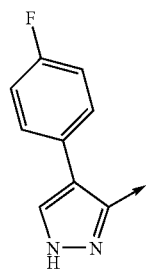 | 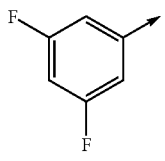 |
| 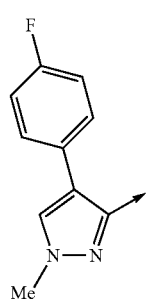 | 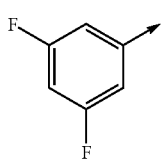 |
| 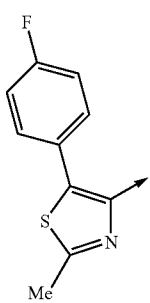 | 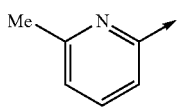 |
-continued
| Ar² | R² |
|---|---|
| 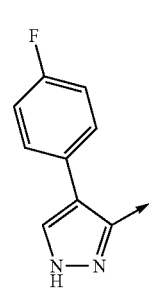 | 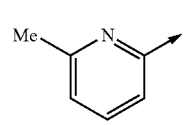 |
| 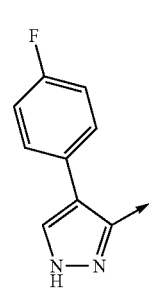 | 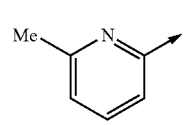 |
| 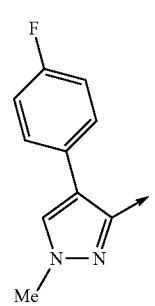 | 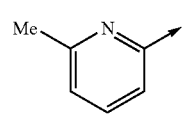 |
| 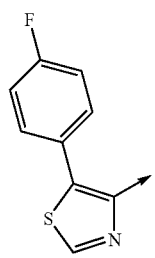 | 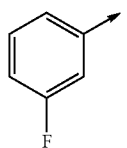 |
| 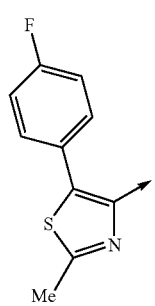 | 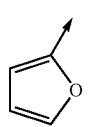 |
| 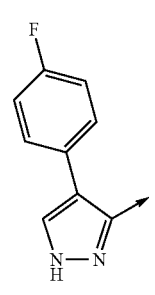 | 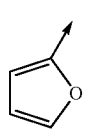 |

| -continued | | | -continued | |
|---|---|---|---|---|
| Ar² | R² | | Ar² | R² |
| 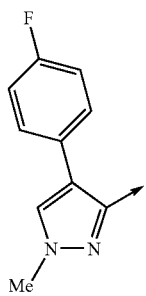 | 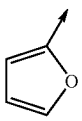 | | 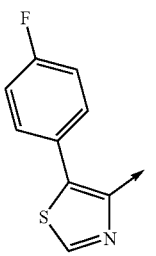 | 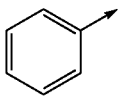 |
| 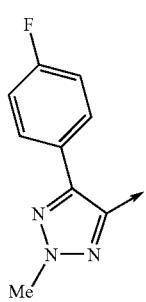 | 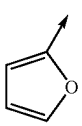 | | 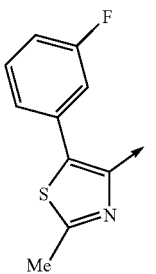 | 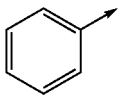 |
| 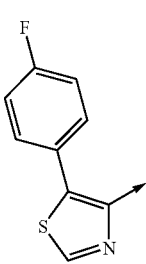 | 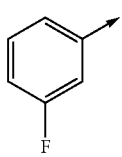 | |  | 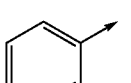 |
| 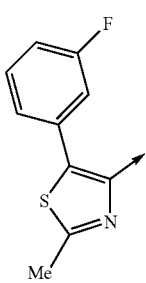 | 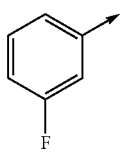 | | 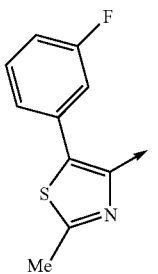 | 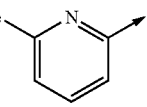 |
| 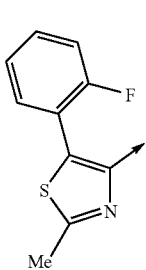 | 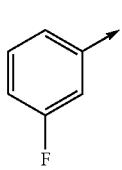 | | 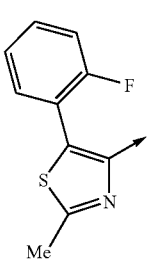 | 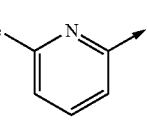 |

-continued

| Ar² | R² |
|---|---|

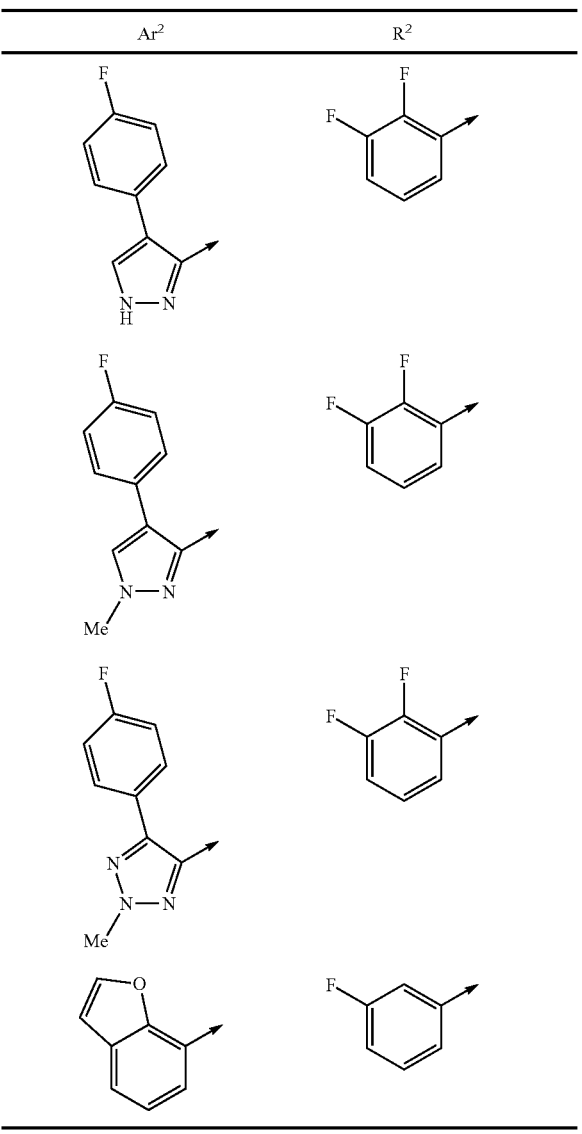

and a pharmaceutically acceptable salt thereof.

7. A pharmaceutical composition comprising the compound of formula (I), or the pharmaceutically acceptable salt thereof, according to claim 1, and a pharmaceutically acceptable carrier.

8. A compound which is (RS)-1-Dibenzofuran-4-yl-1-{2-[5-(3-fluoro-phenyl)-[1,3,4]oxadiazol-2-ylmethyl]-piperidin-1-yl}-methanone or a pharmaceutically acceptable salt thereof.

9. A pharmaceutical composition comprising the compound or the pharmaceutically acceptable salt thereof according to claim 8, and a pharmaceutically acceptable carrier.

10. A method of treating a disease or disorder where an antagonist of a human orexin receptor is required, which comprises administering to a subject in need thereof an effective amount of the compound, or the pharmaceutically acceptable salt thereof, according to claim 1, wherein said disease or disorder is selected from insomnia, parasomnia and jet-lag syndrome.

11. A method of treating a disease or disorder where an antagonist of a human orexin receptor is required, which comprises administering to a subject in need thereof an effective amount of the compound, or the pharmaceutically acceptable salt thereof, according to claim 8, wherein said disease or disorder is selected from insomnia, parasomnia and jet-lag syndrome.

12. A method according to claim 10, wherein said disease or disorder is insomnia.

13. A method according to claim 11, wherein said disease or disorder is insomnia.

14. A method of treating a disease or disorder where an antagonist of a human orexin receptor is required, which comprises administering to a subject in need thereof an effective amount of the compound, or the pharmaceutically acceptable salt thereof, according to claim 1, wherein said disease or disorder is selected from obesity and obesity associated with Type II diabetes.

15. A method of treating a disease or disorder where an antagonist of a human orexin receptor is required, which comprises administering to a subject in need thereof an effective amount of the compound, or the pharmaceutically acceptable salt thereof, according to claim 8, wherein said disease or disorder is selected from obesity and obesity associated with Type II diabetes.

* * * * *